(12) United States Patent
Schatz

(10) Patent No.: US 7,745,129 B1
(45) Date of Patent: Jun. 29, 2010

(54) METHODS FOR SEQUENCING OF A NECLEIC ACID

(76) Inventor: Kenneth David Schatz, 1325 Montclaire Way, Los Altos, CA (US) 94024

( * ) Notice: Subject to any disclaimer, the term of this patent is extended or adjusted under 35 U.S.C. 154(b) by 0 days.

(21) Appl. No.: 11/827,588

(22) Filed: Jul. 11, 2007

Related U.S. Application Data

(60) Provisional application No. 60/830,417, filed on Jul. 12, 2006.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search .................... 435/6; 536/22.1, 23.1, 24.3
See application file for complete search history.

(56) References Cited

U.S. PATENT DOCUMENTS

| | | | | |
|---|---|---|---|---|
| 5,356,776 | A * | 10/1994 | Kambara et al. | 435/6 |
| 5,451,503 | A * | 9/1995 | Hogan et al. | 435/6 |
| 5,525,464 | A * | 6/1996 | Drmanac et al. | 435/6 |
| 5,714,330 | A | 2/1998 | Brenner | |
| 5,720,928 | A * | 2/1998 | Schwartz | 422/186 |
| 5,851,769 | A * | 12/1998 | Gray et al. | 435/6 |
| 6,147,198 | A * | 11/2000 | Schwartz | 536/23.1 |
| 6,150,089 | A * | 11/2000 | Schwartz | 435/6 |
| 6,322,968 | B1 | 11/2001 | Head | |
| 6,448,012 | B1 * | 9/2002 | Schwartz | 435/6 |
| 6,696,022 | B1 * | 2/2004 | Chan et al. | 422/99 |
| 7,151,598 | B2 * | 12/2006 | Poponin | 356/301 |
| 7,163,658 | B2 * | 1/2007 | Bension | 422/68.1 |
| 7,198,900 | B2 * | 4/2007 | Woudenberg et al. | 435/6 |
| 2002/0081744 | A1 * | 6/2002 | Chan et al. | 436/94 |
| 2005/0100893 | A1 * | 5/2005 | Gunderson et al. | 435/6 |
| 2007/0111303 | A1 * | 5/2007 | Inoue et al. | 435/287.2 |
| 2007/0184446 | A1 * | 8/2007 | Matsumoto et al. | 435/6 |
| 2008/0213912 | A1 * | 9/2008 | Randall et al. | 436/94 |
| 2009/0246834 | A1 * | 10/2009 | Goel | 435/91.2 |
| 2009/0305287 | A1 * | 12/2009 | Nordman et al. | 435/6 |

OTHER PUBLICATIONS

Chan et al. DNA mapping using microfluidic stretching and single-molecule detection of fluorescent site-specific tags. Genome Research 14: 1137-1146 (2004).*

Sanger, F., Nicklen, S., Coulson, A.R., DNA sequencing with chain-terminating inhibitors, Proc. Natl. Acad. Sci. USA, Dec. 1977, pp. 5463-5467, vol. 74, No. 12.

Hyman, E.D., A new method of sequencing DNA, Analytical Biochemistry, Nov. 1, 1988, pp. 423-436, vol. 174, No. 2, Academic Press Inc., San Diego.

Ronaghi, M., Uhlen, M., Nyren, P., A sequencing method based on real-time pyrophosphate, Science, Jul. 17, 1998, pp. 363-365, vol. 281, AAAS, Washington DC.

Strezoska, Z., et al., DNA sequencing by hybridization: 100 bases read by a non-gel-based method, Proc. Natl. Acad. Sci. USA, Nov. 1991, pp. 10089-10093, vol. 88.

Chee, M., et al., Accessing genetic information with high-density DNA arrays, Science, Oct. 25, 1996, pp. 610-614, vol. 274, AAAS, Washington DC.

Hansma, H.G., et al., Reproducible imaaging and dissection of plasmid DNA under liquid with the atomic force microscope, Science, May 22, 1992, pp. 1180-1184, vol. 256.

Fried, M.G., et al., Role of hydration in the binding of lac repressor to DNA, Journal of Biological Chemistry, Dec. 27, 2002, pp. 50676-50682, vol. 277, No. 52.

Parra, I., Windle, B., High resolution visual mapping of stretched DNA by fluorescent hybridization, Nature Genetics, Sep. 1993, pp. 17-21, vol. 5, No. 1.

Weier, H-U.G., et al., Quantitative DNA fiber mapping, Human Molecular Genetics, 1995, pp. 1903-1910, vol. 4, No. 10, Oxford University Press, Oxford, England.

Chu, B.C.F., Wahl, G.M., Orgel, L.E., Derivatization of unprotected polynucleotides, Nucleic Acids Research, 1983, pp. 6513-6529, vol. 11, No. 18, IRL Press Ltd, Oxford, England.

Inman, R.B., Schnos, M., Partial Denaturation of Thymine- and 5-Bromouracil-containing DNA in alkali, Journal of Molecular Biology, 1970, pp. 93-98, vol. 49, Elsevier Ltd, UK.

Bensimon, A., et al., Alignment and sensitive detection of DNA by a moving interface, Science, Sep. 30, 1994, pp. 2096-2098, vol. 265, AAAS, Washington DC.

* cited by examiner

*Primary Examiner*—Ethan Whisenant

(57) ABSTRACT

Improved labeled molecule probes for use in biomedical applications including the sequencing of nucleic acid molecules and methods and apparatuses for their use are detailed. Labeled-probe-assemblies, comprising a probe element, for binding to a target molecule, attached to a label-assembly further comprising a linear series of information encoded structures and means for spatially separating these structures, are presented together with methods for extending the label assemblies such that the information encoded structures can be individually resolved, substantially simultaneously, by a readout device.

17 Claims, 50 Drawing Sheets

Figure 1:
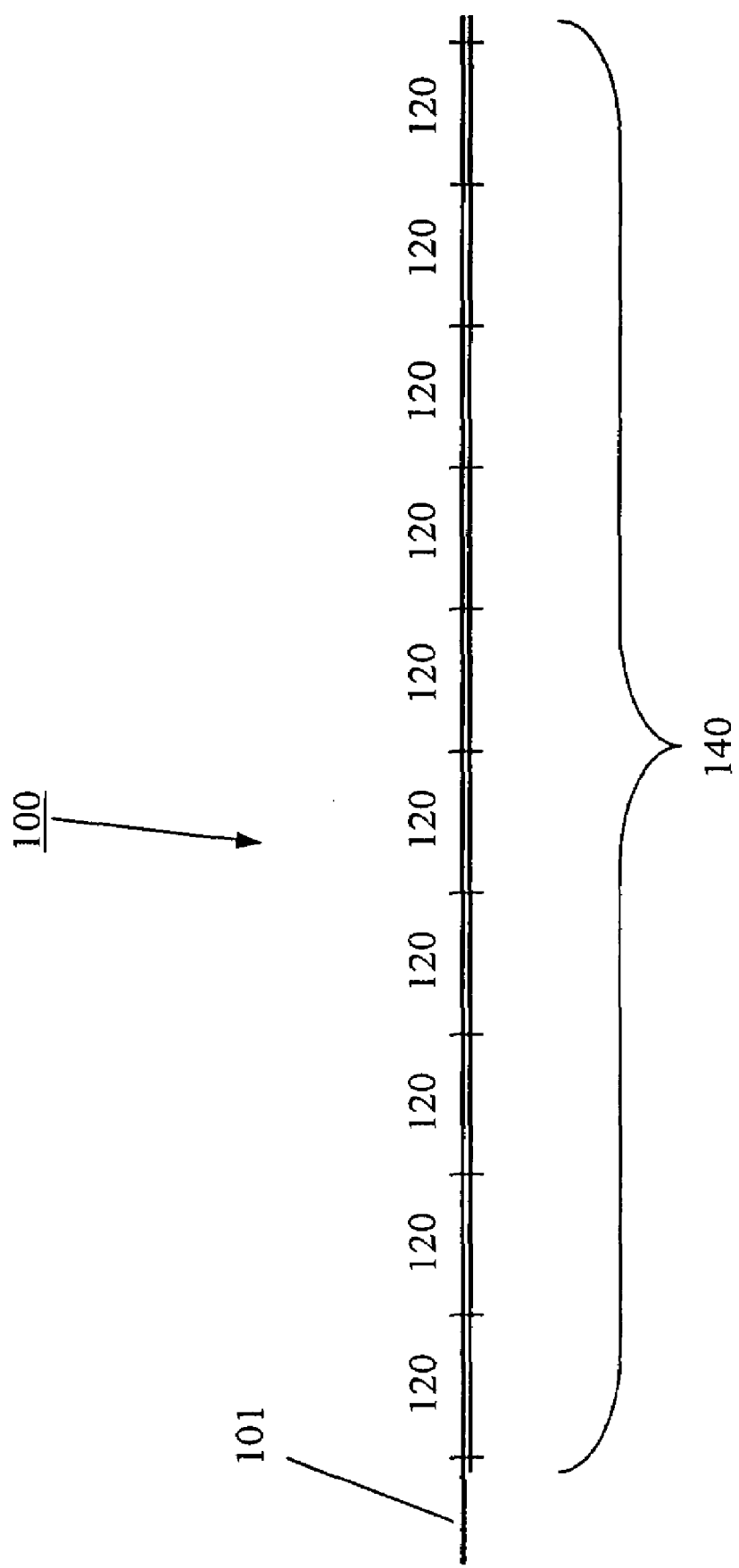

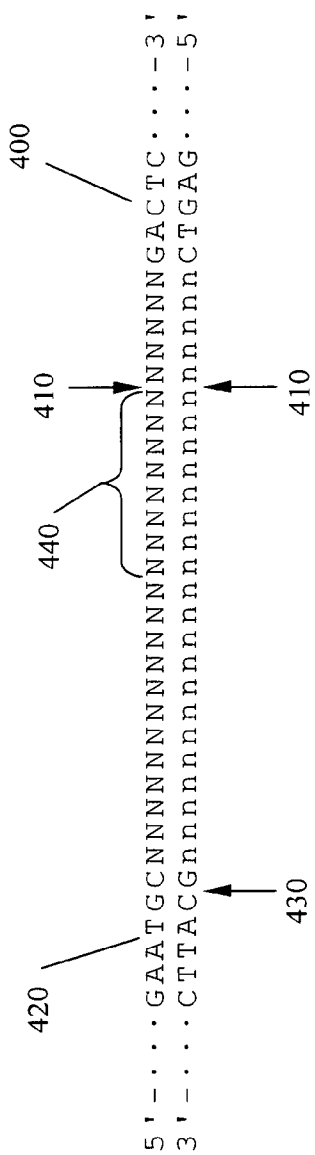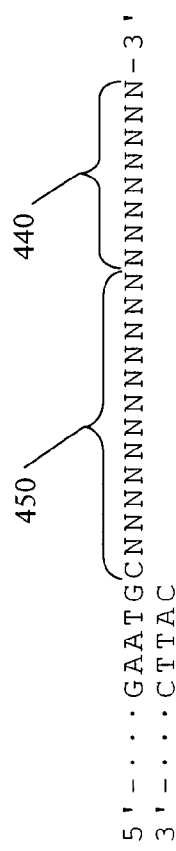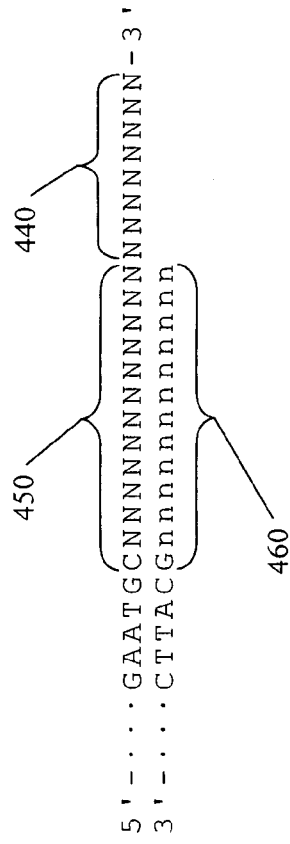
Figure 4a
Figure 4b
Figure 4c

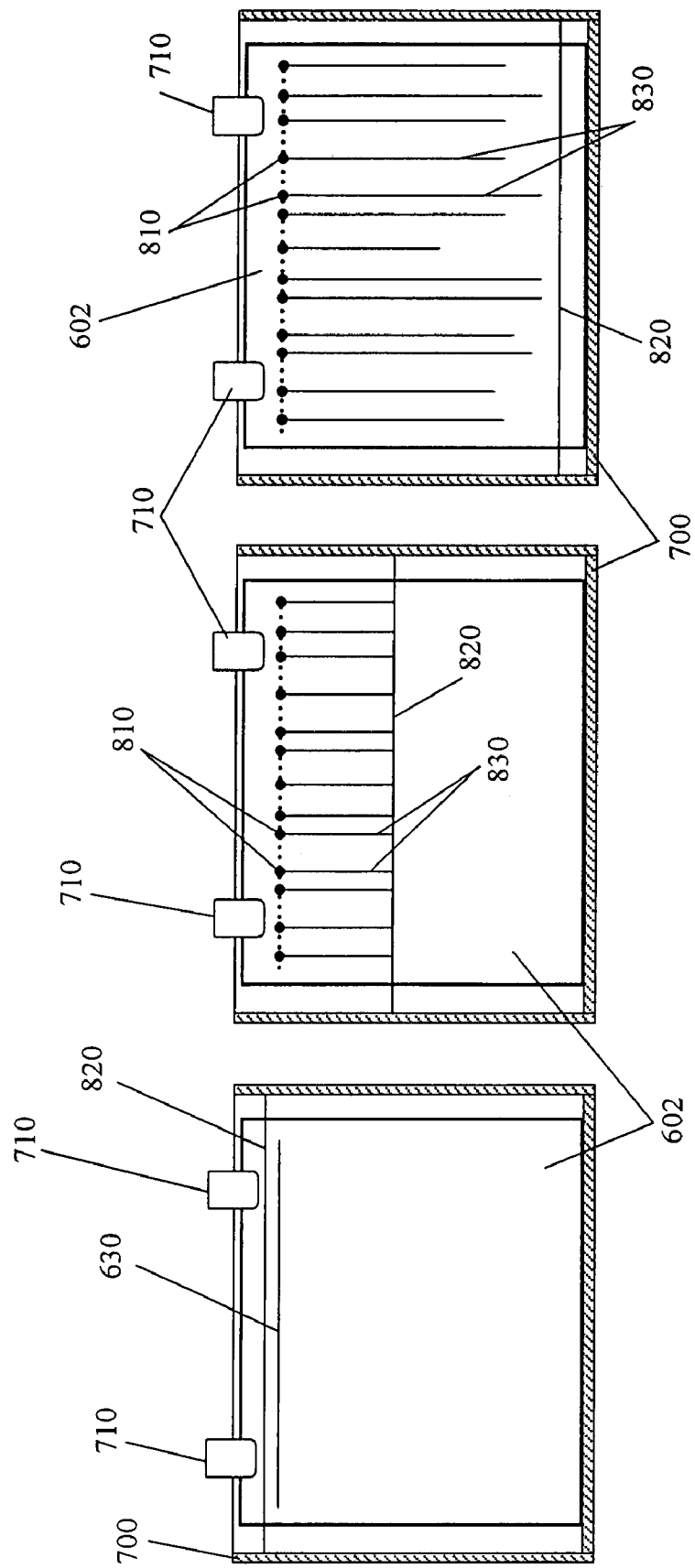

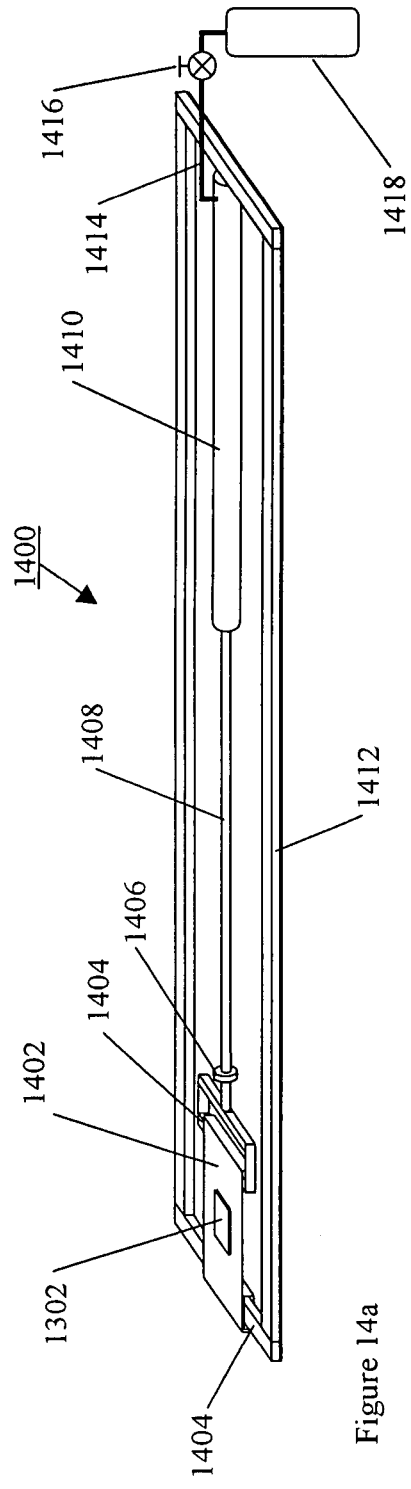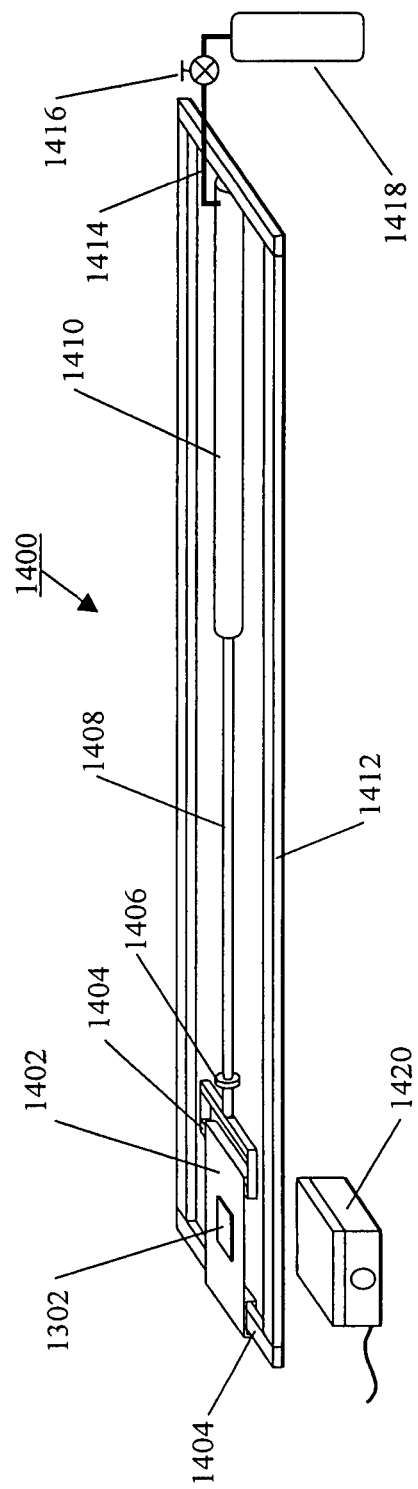
Figure 14a
Figure 14b

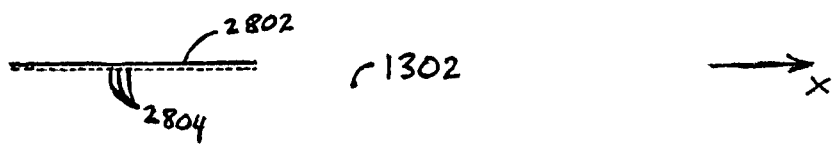
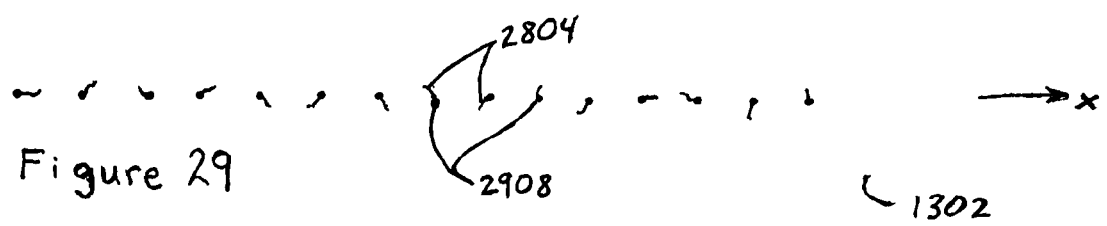
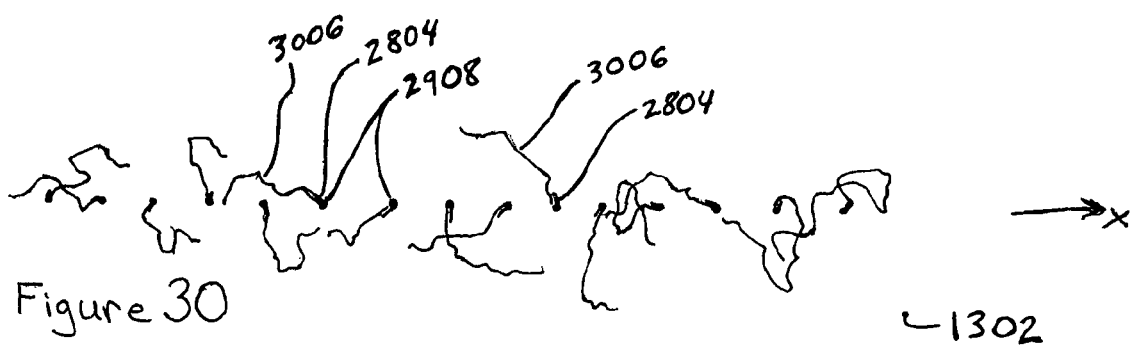
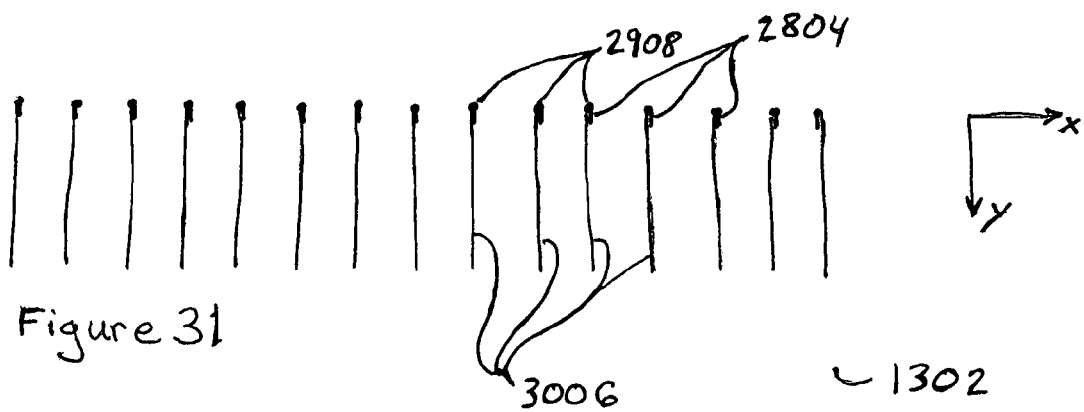

Figure 51

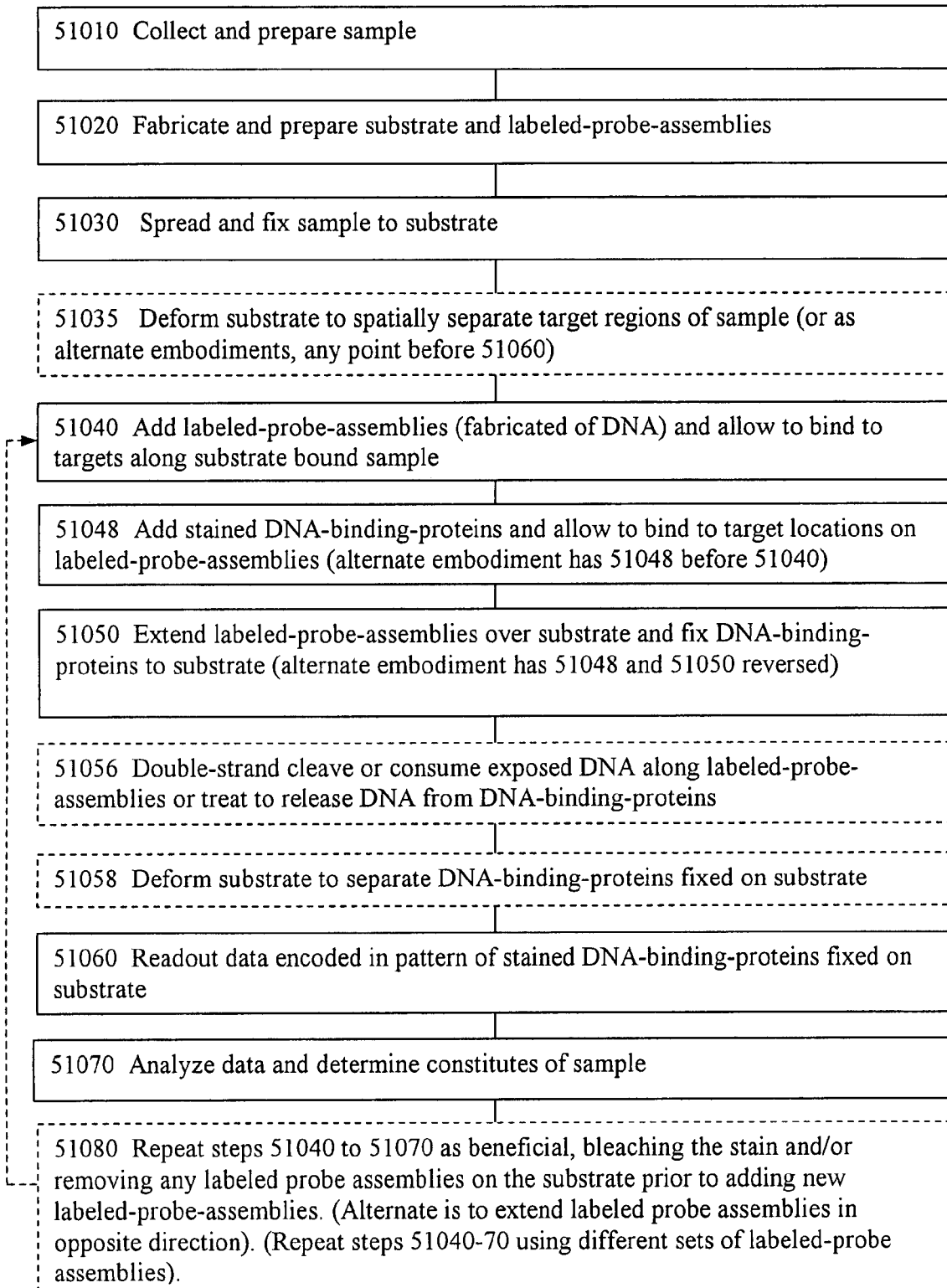

51010 Collect and prepare sample

51020 Fabricate and prepare substrate and labeled-probe-assemblies

51030 Spread and fix sample to substrate

51035 Deform substrate to spatially separate target regions of sample (or as alternate embodiments, any point before 51060)

51040 Add labeled-probe-assemblies (fabricated of DNA) and allow to bind to targets along substrate bound sample 51048 Add stained DNA-binding-proteins and allow to bind to target locations on labeled-probe-assemblies (alternate embodiment has 51048 before 51040)

51050 Extend labeled-probe-assemblies over substrate and fix DNA-binding-proteins to substrate (alternate embodiment has 51048 and 51050 reversed)

51056 Double-strand cleave or consume exposed DNA along labeled-probe-assemblies or treat to release DNA from DNA-binding-proteins 51058 Deform substrate to separate DNA-binding-proteins fixed on substrate 51060 Readout data encoded in pattern of stained DNA-binding-proteins fixed on substrate 51070 Analyze data and determine constitutes of sample 51080 Repeat steps 51040 to 51070 as beneficial, bleaching the stain and/or removing any labeled probe assemblies on the substrate prior to adding new labeled-probe-assemblies. (Alternate is to extend labeled probe assemblies in opposite direction). (Repeat steps 51040-70 using different sets of labeled-probe assemblies).

SEQUENCE LISTING

```
<160> NUMBER OF SEQ ID NOS: 6

<210> SEQ ID NO 1
<211> LENGTH: 35
<212> TYPE: DNA
<213> ORGANISM: Escherichia coli
<220> FEATURE:
<223> OTHER INFORMATION: Portion of lac operator from wild-type E. coli
```

```
-continued

<400> SEQUENCE: 1
tgtgtggaat tgtgagcgga taacaatttc acaca                              35

<210> SEQ ID NO 2
<211> LENGTH: 35
<212> TYPE: DNA
<213> ORGANISM: Escherichia coli
<220> FEATURE:
<223> OTHER INFORMATION: Portion of lac operator from wild-type E. coli

<400> SEQUENCE: 2
tgtgtgaaat tgttatccgc tcacaattcc acaca                              35

<210> SEQ ID NO 3
<211> LENGTH: 36
<212> TYPE: DNA
<213> ORGANISM: Artificial Sequence
<220> FEATURE:
<221> NAME/KEY: unsure
<222> LOCATION: 7..31
<223> OTHER INFORMATION: Synthetic polynucleotide sequence

<400> SEQUENCE: 3
gaatgcnnnn nnnnnnnnn nnnnnnnnnn ngactc                              36

<210> SEQ ID NO 4
<211> LENGTH: 36
<212> TYPE: DNA
<213> ORGANISM: Artificial Sequence
<220> FEATURE:
<221> NAME/KEY: unsure
<222> LOCATION: 6..30
<223> OTHER INFORMATION: Synthetic polynucleotide sequence

<400> SEQUENCE: 4
gagtcnnnnn nnnnnnnnnn nnnnnnnnnn gcattc                             36

<210> SEQ ID NO 5
<211> LENGTH: 27
<212> TYPE: DNA
<213> ORGANISM: Artificial Sequence
<220> FEATURE:
<221> NAME/KEY: unsure
<222> LOCATION: 6..22
<223> OTHER INFORMATION: Synthetic polynucleotide sequence

<400> SEQUENCE: 5
ggatcnnnnn nnnnnnnnnn nngactc                                       27

<210> SEQ ID NO 6
<211> LENGTH: 27
<212> TYPE: DNA
<213> ORGANISM: Artificial Sequence
<220> FEATURE:
<221> NAME/KEY: unsure
<222> LOCATION: 6..22
<223> OTHER INFORMATION: Synthetic polynucleotide sequence

<400> SEQUENCE: 6
gagtcnnnnn nnnnnnnnnn nngatcc                                       27
```

METHODS FOR SEQUENCING OF A NECLEIC ACID

CROSS-REFERENCE TO RELATED APPLICATIONS

This application claims the benefit of provisional patent application No. 60/830,417, filed 2006 Jul. 12 by the present inventor.

FEDERALLY SPONSORED RESEARCH

Not Applicable

SEQUENCE LISTING OR PROGRAM

A Sequence Listing of nucleic acid base sequences is included as an appendix.

BACKGROUND OF THE INVENTION

1. Field of Invention

The invention generally relates to methods and apparatuses for investigating bio-molecules, and specifically relates to methods and apparatuses for determining the sequence of a nucleic acid.

2. Prior Art

The quest for low-cost methods of sequencing nucleic acids has been driven by its recognized importance to biological and medical research, and ultimately by its potential to impact the practice of medicine. Consequently, many techniques have been explored and reviewed, including variations on the classic chain-termination strategy of Sanger et al. PNAS 74:5463 5467 (1977), pyrosequencing, see for example Hyman E. D. Analytical Biochem 174:423 436 (1988), and other sequencing by synthesis or sequencing by incorporation methods, see for example Ronaghi et al. Science 281:363 365 (1998), sequencing by hybridization techniques, for example Strezoska et al. PNAS 88:10089 10093 (1991), including micro-array techniques, for example Chee et al., Science 274:610 614 (1996), and direct imaging of bases by micro-probes, for example Hansma et al. Science 256:1180 1184 (1992). A hybrid sequencing by hybridization and chain-termination technique is presented by Head et al. in U.S. Pat. No. 6,322,968 that employs probes having a short spacer arm. In their method, probes are lengthened by the polymerase and a chain-terminating and labeled nucleotide. The method is an array technique with the added complexity of an enzymatic process. In general, all these sequencing methods suffer from one or more of the following issues: short read lengths on un-correlated fragments, time-consuming cyclic processes conducted in expensive equipment, excessive consumption of expensive reagents, difficult and costly to analyze data sets, and reliance on alternate means for generating a sequence scaffold or map. The present invention is designed to circumvent these issues.

SUMMARY

Labeled-Probe-Assemblies

Labeled-probe-assemblies, methods for their manufacture, and their uses are disclosed in this document. The labeled-probe-assemblies disclosed here are distinct from existing labeled-probes in that multiple bits of information are encoded along the length of the assembly, and in use, the individual bits can be spatially resolved from each other, allowing them to be readout in order and substantially simultaneously. The labeled-probe-assemblies described include a probe connected to a label-assembly, along which multiple information encoded structures are located, one after another in a linear fashion like words along a sentence. Information can be encoded along the label-assembly in the order, spatial separation between, and length of individual information encoded structures. Additional information can be encoded into the individual information encoded structures by label structures, for example fluorescent dye molecules, or target structures that in use are indirectly-labeled with fluorescent dye molecules. Recovery of the information encoded along the label-assembly is accomplished by extending and spatially separating, while maintaining the correct ordering of, the individual information encoded structures such that they can be detected and resolved by suitable information readout hardware.

As information along the label-assembly can be spatially resolved, a great deal of information can be encoded in a very compact structure. For example, where four distinct dye types are incorporated along the label-assembly, and where, for adequate spatial resolution, each information encoded structure is separated by, for example, one micron, to uniquely label an N-mer probe (where N is the number of bases) would require a label-assembly approximately N microns in length. In this example, four dye types suffice to label $4^N$ unique labeled-probe-assemblies, each having a different N-mer probe sequence. By constructing the label-assembly backbone from double-stranded DNA (dsDNA), or other high aspect ratio and high molecular weight polymer, it becomes relatively easy to store the base sequence information of a random 10-mer, for example, or shorter or longer sequence. Furthermore, by constructing the label-assembly backbone of a cleavable molecule, and after extending, fixing to a substrate, and cleaving, the substrate can be stretched to separate the individual bits of data so that their order and identity can be resolved. By this method, a great deal of information can be stored and recovered from a relatively shorter label-assembly. By these methods, the practical limit on the amount of information that can be stored and recovered from a single labeled-probe-assembly extends into the tens and hundreds of bits. Where these methods are used to label complete sets of N-mer probes, forming labeled-probe-assemblies, the practical limits on the size N are driven more by the combinometrics of the manufacturing process than the information capacity of the label-assemblies.

Labeled-probe-assemblies can be used for sequencing of deoxyribonucleic acid (DNA) by hybridization, wherein the probes are a complete set of N-mers, such as 10-mers, that hybridize to complementary sequences along the sample DNA. In addition, labeled-probe-assemblies can be used to detect and identify many types of targets, including proteins, antigens, antibodies, receptors, single stranded RNA (ssRNA), sequences, single stranded DNA (ssDNA), double stranded RNA (dsRNA), dsDNA, complementary DNA (cDNA), single nucleotide polymorphisms (SNPs), and other target of interest.

Sequencing of DNA with Labeled-Probe-Assemblies

Sample DNA molecules can be sequenced using labeled-probe-assemblies, including very long sample DNA molecules, and these same methods can also be applied to sequence RNA and peptide nucleic acid or protein nucleic acid (PNA) molecules. For sequencing application, labeled-probe-assemblies are typically fabricated with ssDNA probes, and for each labeled-probe-assembly, the information encoded along its label-assembly is the identity and orientation of the base sequence complementary to the base sequence of its probe. The probes are designed to hybridize to complementary regions along the sample DNA. A complete, spanning, set of labeled-probe-assemblies is used. The complete set includes labeled-probe-assemblies with all possible probe sequences for the given probe length.

In an example sequencing process, multiple molecules of sample DNA are extended over and fixed to the surface of a substrate. During this step, the sample DNA molecules are extended in primarily a single predetermined direction, such that the extended and fixed sample DNA molecules form approximately straight lines on the substrate, with the axes of the various sample DNA molecules approximately parallel to each other.

The substrate is then added to a hybridization solution containing multiple copies of the complete set of labeled-probe-assemblies. Each complete set including all possible probe sequences for the given probe length, or otherwise, including all probe sequences necessary to sequence the sample DNA. Labeled-probe-assemblies are allowed to hybridize to complementary sequences along the sample DNA molecules. Those labeled-probe-assemblies that are hybridized to the sample DNA molecules are thereby anchored to the substrate substantially by their probes. The anchored labeled-probe-assemblies are then extended in a direction approximately perpendicular to the direction in which the sample DNA molecules where extended, and are fixed to the substrate. The resulting structure of each sample DNA molecule and hybridized labeled-probe-assemblies is like that of a comb, with the sample DNA molecule forming the spine, or backbone, of the comb and the labeled-probe-assemblies forming the individual twines, or teeth. The labeled-probe-assemblies are all oriented approximately parallel to each other, and approximately perpendicular to the sample DNA molecule.

The substrate is then loaded onto a data readout device. The readout device includes a means for visualizing, imaging, the information encoded along the labeled-probe-assemblies, such as a microscope setup for fluorescence microscopy when the information is encoded with fluorescent stain. The readout apparatus also includes means for recording and analyzing images of the data encoded along the labeled-probe-assemblies, such as a CCD camera on the microscope and connected computer with image analysis software.

The information generated by the image analysis software is the base sequence and orientation of the sample DNA at the location of each labeled-probe-assembly hybridized along the sample DNA, the order of these probe-length sequence fragments along the sample DNA, and the distance between each of these sequence fragments. The information generated from multiple sample DNA molecules can be combined, by for example existing multiple sequence alignment software packages, to generate the sequence for the entire length of the sample DNA molecule.

This sequencing method is compatible with very long sample DNA molecules, millions of base pairs long and longer. The upper limit on length being set by ones ability to isolate unbroken molecules, rather than an issue with this method. Furthermore, this method allows simultaneous processing of mixed sets of sample DNA molecules. These properties provide substantial benefit over existing sequencing methods, as sample preparation is minimal and the large amount of sequence data collected along each long sample DNA molecule greatly facilitates the multiple sequence alignment process.

Key to this sequencing method is the extension over the surface of the substrate the sample DNA molecules and the hybridized labeled-probe-assemblies, along perpendicular axes. Both the sample DNA molecules and the labeled-probe-assemblies hybridized to them are extended and fixed to the surface of the substrate, such that each molecule forms an approximately straight line. However, the labeled-probe-assemblies are extended in a direction approximately perpendicular to that of the long axis of the sample DNA molecules. For a given substrate condition, the amount of data that can be recovered from a length of one sample DNA molecule is maximized when the hybridized labeled-probe-assemblies lie at right angles to the sample DNA molecule.

The number of sample DNA molecules that must be analyzed in order to recover sufficient data to piece together the entire sequence of the sample is set by the allowable maximum coverage of probe on a single sample DNA molecule. This allowable maximum coverage is limited by the spatial resolution of the readout apparatus and stain employed, as the information in adjacent labeled-probe-assemblies must be resolved.

This invention includes alternate embodiments in which the allowable maximum coverage is increased by deforming, stretching, expanding, or otherwise elongating the substrate along the same direction in which the sample DNA molecules where extended. In these alternate embodiments, the substrate deformation step is performed after the sample DNA molecules have been extended and fixed to the substrate, and typically entails breaking each sample DNA molecule into a large number of short pieces, fragments. The pieces remain fixed to the substrate, and the order of the pieces along the substrate remains the same as in the original sample DNA molecule. One labeled-probe-assembly can then be hybridized to each short piece of the sample DNA, and the allowable maximum coverage of probe is increased by approximately the same factor by which the substrate was elongated. Fewer sample DNA molecules need be processed and analyzed, and the final multiple sequence alignment analysis is greatly simplified, as the proportion of each sample DNA molecule hybridized with probe is increased. Hence, significant benefit can be derived from the substrate deformation method. Methods and hardware for elongating a substrate while maintaining the ordering of fixed fragments are also disclosed herein.

DRAWINGS

In the drawings, closely related figures have the same number but different alphabetic suffixes.

FIG. 1. Illustration of main components of generic Labeled-probe-assembly.

Figure 2:
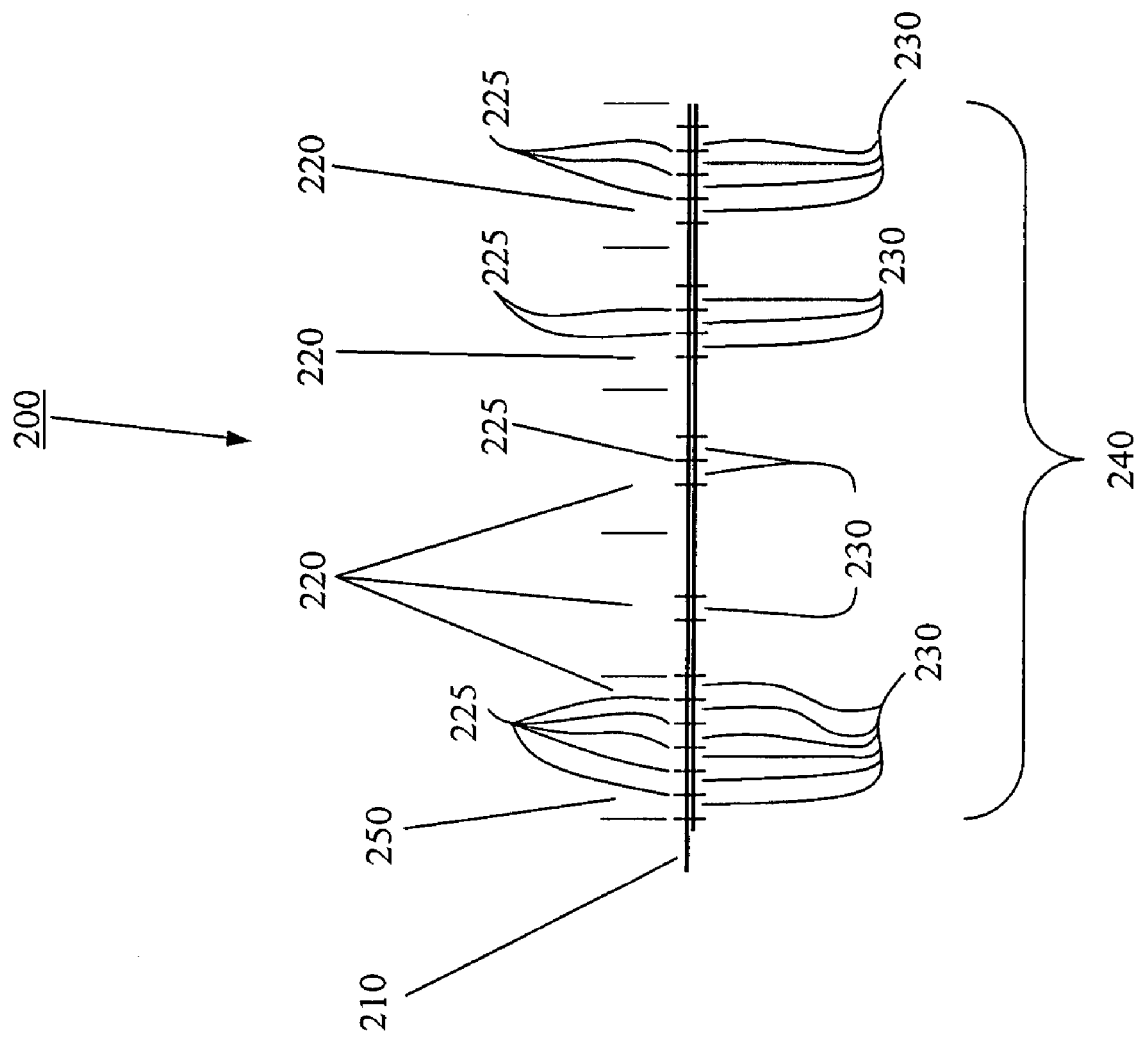

FIG. 2. Illustration of main components of Labeled-probe-assembly with binding sites for sequence-specific DNA-binding proteins.

Figure 3:
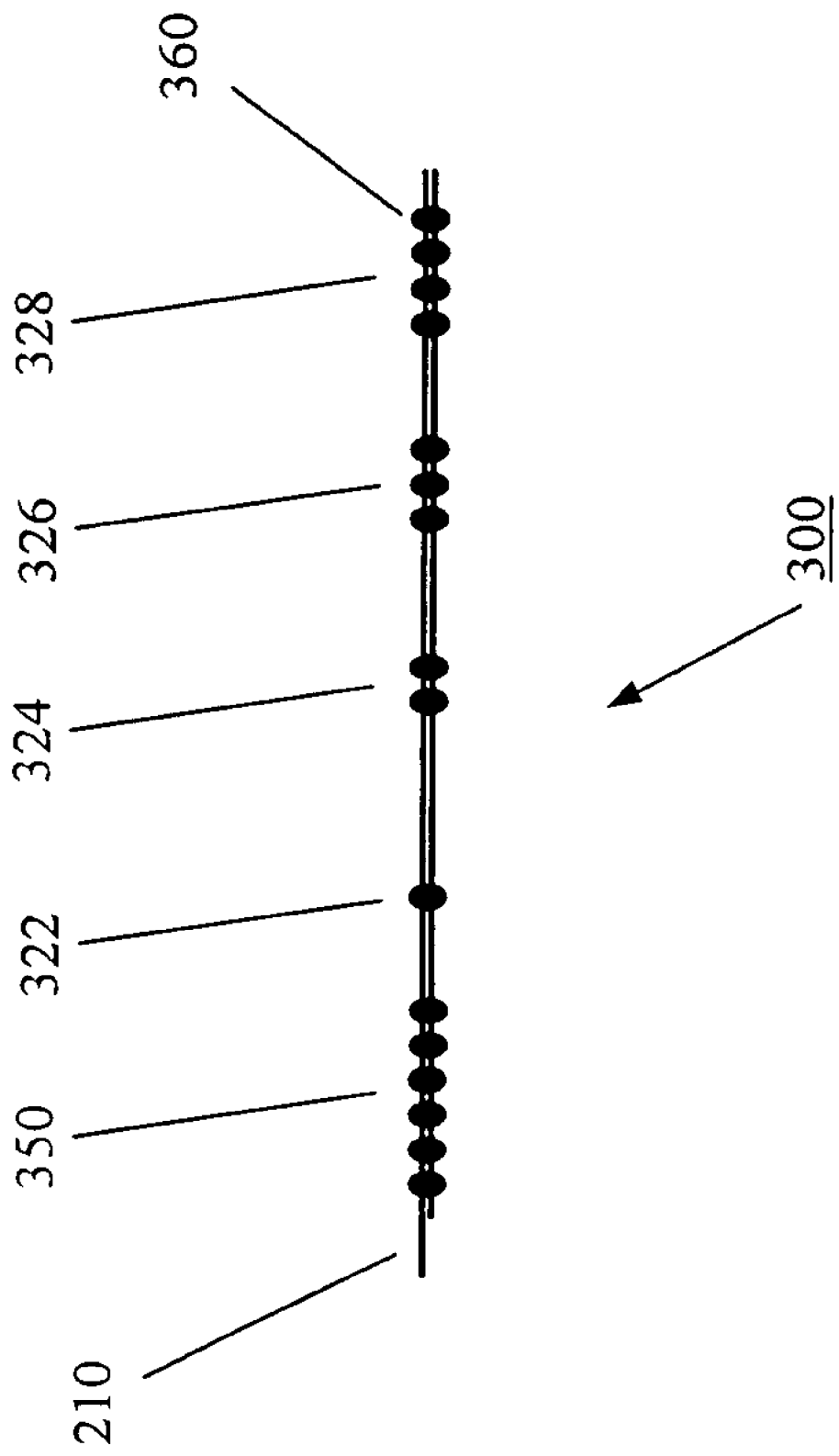

FIG. 3. Illustration of main components of Labeled-probe-assembly with bound sequence-specific DNA-binding proteins.

FIG. 4a. Illustration of probe region as amplified, SEQ ID NO:3, illustrated with 5'-end to the left, annealed to its complement, SEQ ID NO:4, with residue 1 of SEQ ID NO:3 aligned to residue 36 of SEQ ID NO:4.

FIG. 4b. Illustration of probe region, as cut by nicking and restriction enzymes, resulting in residues 1 through 26 of SEQ ID NO:3 annealed to residues 32 through 36 of SEQ ID NO:4, with residue 1 of SEQ ID NO:3 aligned to residue 36 of SEQ ID NO:4.

FIG. 4c. Illustration of probe region formed on labeled-probe-assembly, residues 1 through 26 of SEQ ID NO:3 annealed to residues 19 through 36 of SEQ ID NO:4, with residue 1 of SEQ ID NO:3 aligned to residue 36 of SEQ ID NO:4.

Figure 5A:
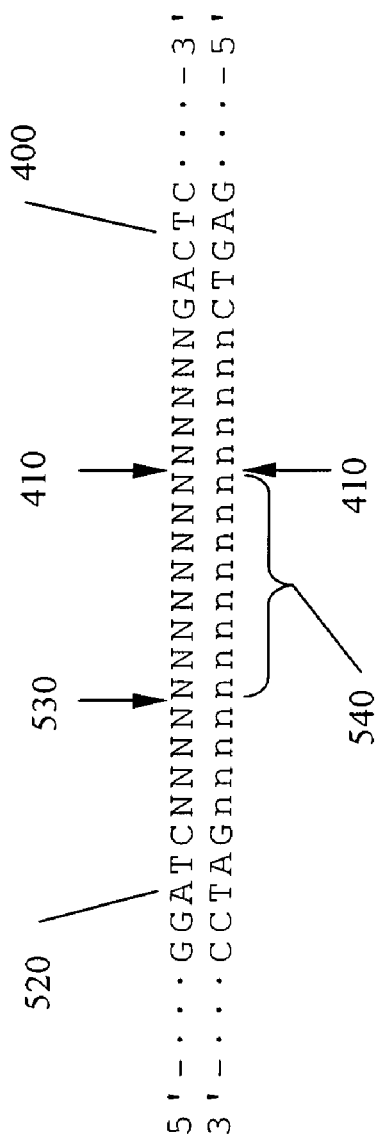

FIG. 5a. Illustration of probe region as amplified, SEQ ID NO:5, illustrated with 5'-end to left, annealed to its complement, SEQ ID NO:6, with residue 1 of SEQ ID NO:5 aligned to residue 27 of SEQ ID NO:6.

Figure 5B:
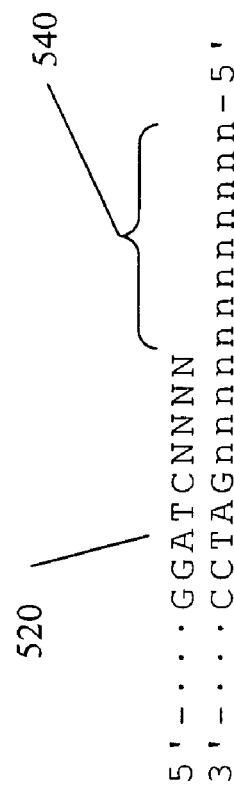

FIG. 5b. Illustration of probe region formed on labeled-probe-assembly, residues 1 through 9 of SEQ ID NO:5 annealed along the residues 11 through 27 of SEQ ID NO:6, with residue 1 of SEQ ID NO:5 aligned to residue 27 of SEQ ID NO:6.

Figure 6A:
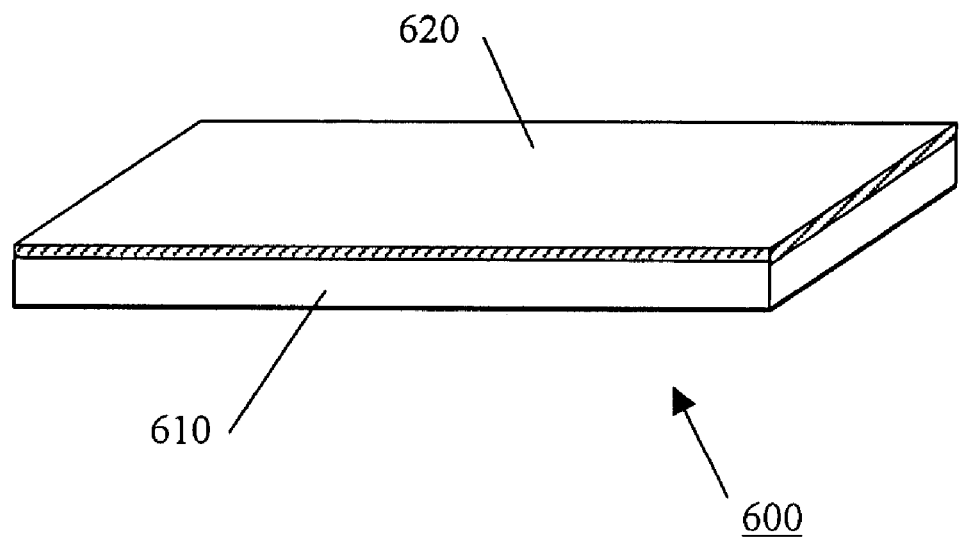

FIG. 6a. Illustration of two layer substrate.

Figure 6B:
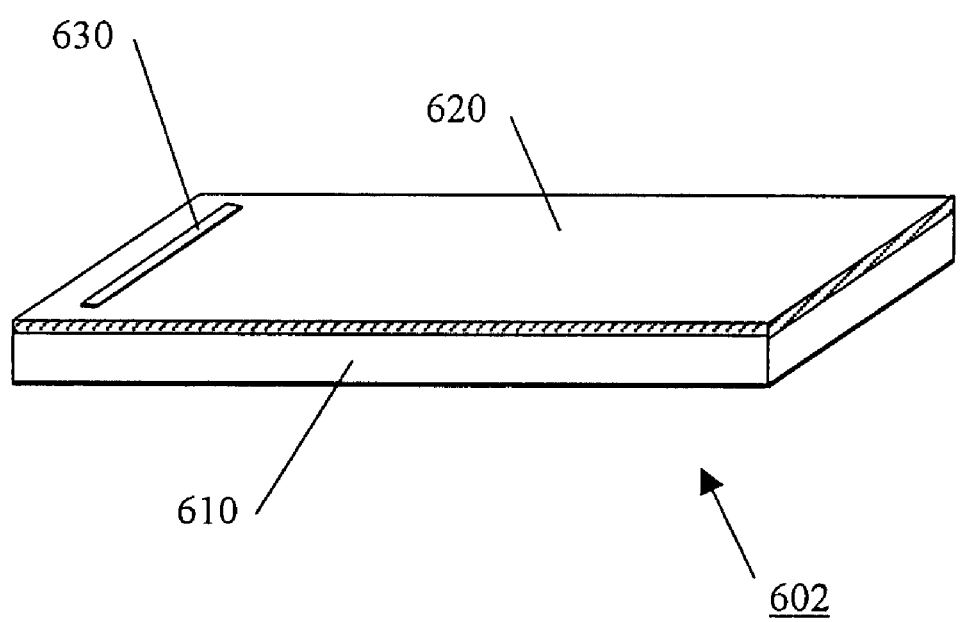

FIG. 6b. Illustration of two-layer substrate with narrow strip of avidin molecules.

Figure 7B:
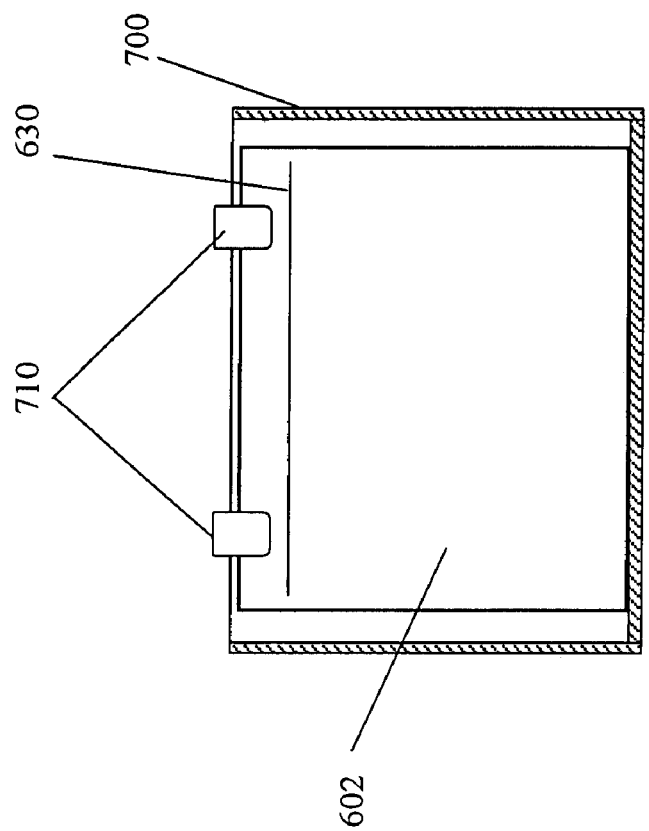
Figure 7A:
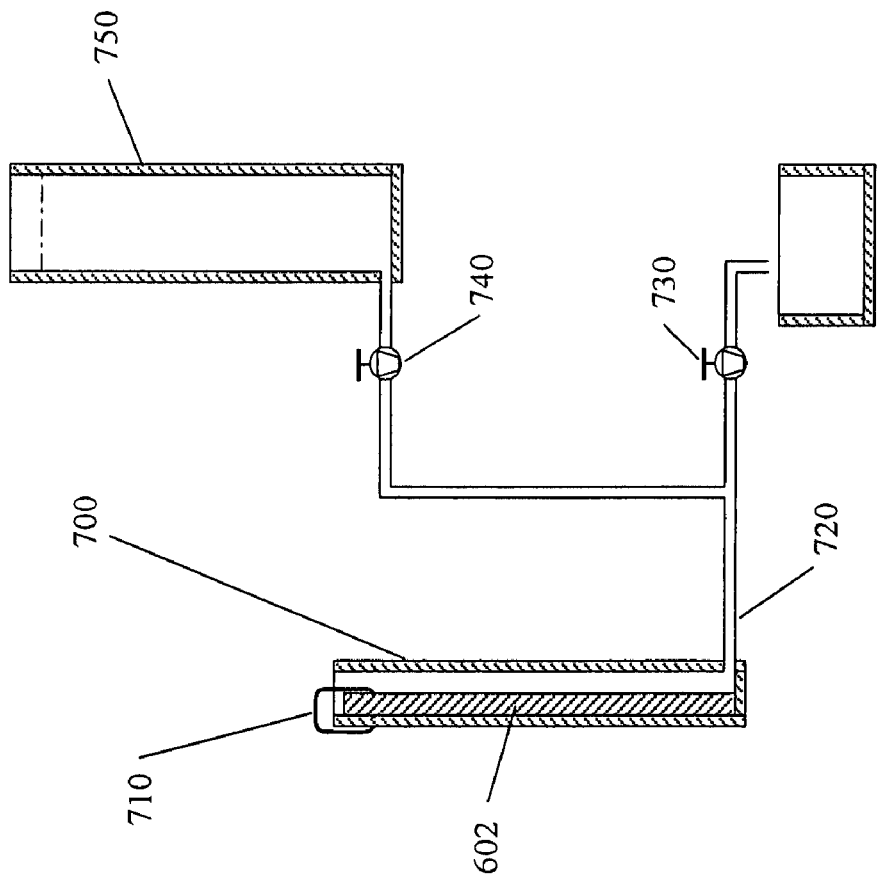

FIG. 7a. Illustration of side-view cut-away of apparatus for extending DNA over substrate.

FIG. 7b. Front view cut-away of apparatus for extending DNA over substrate.

FIG. 8a. Front view cut-away of apparatus for extending DNA over substrate, at start of extension process.

FIG. 8b. Front view cut-away of apparatus for extending DNA over substrate, part way through extension process.

FIG. 8c. Front view cut-away of apparatus for extending DNA over substrate, at end of extension process.

Figure 9:
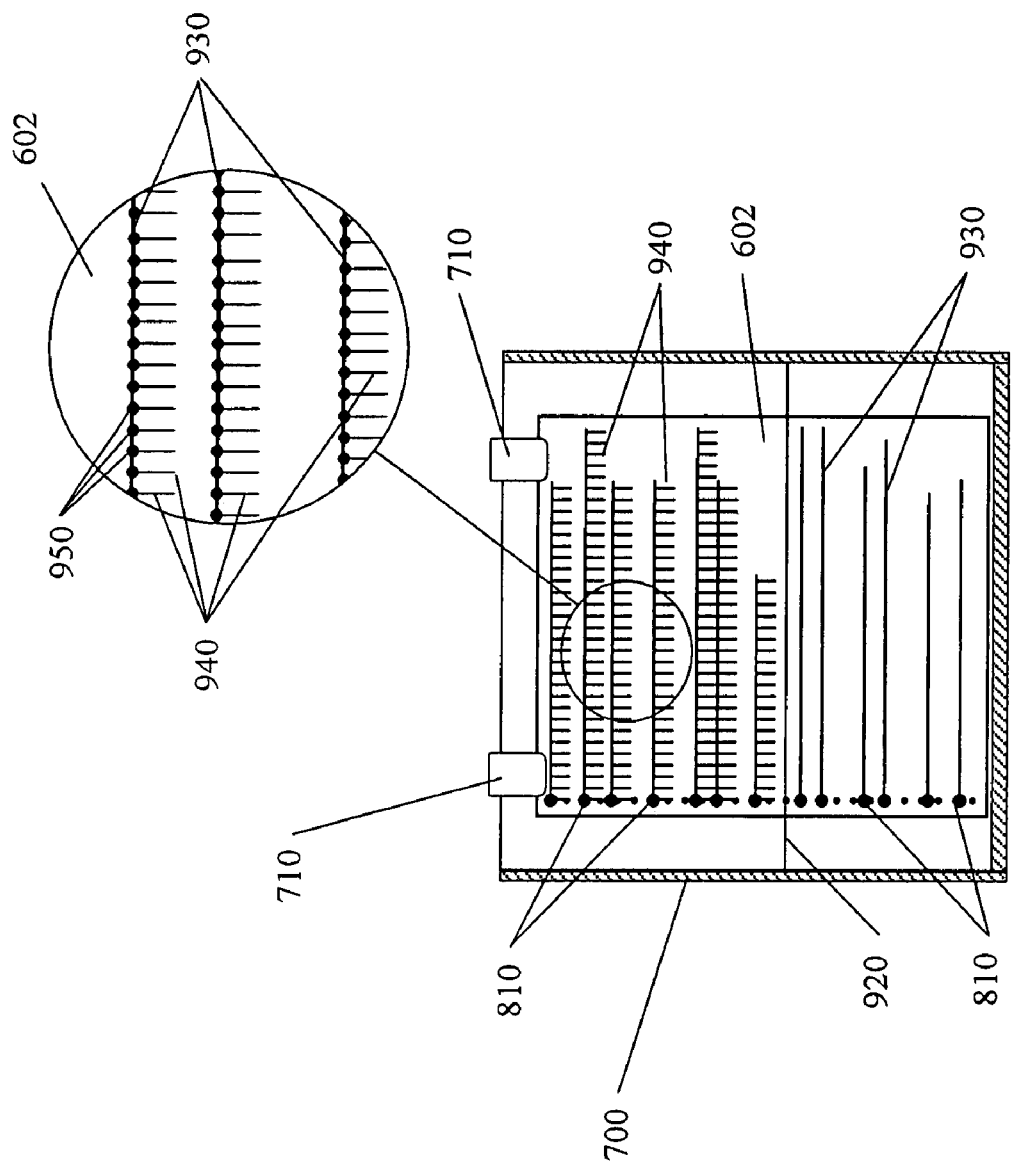

FIG. 9. Front view cut-away of apparatus for extending DNA over substrate, part way through process of extending labeled-probe-assemblies, with close-up view.

Figure 10:
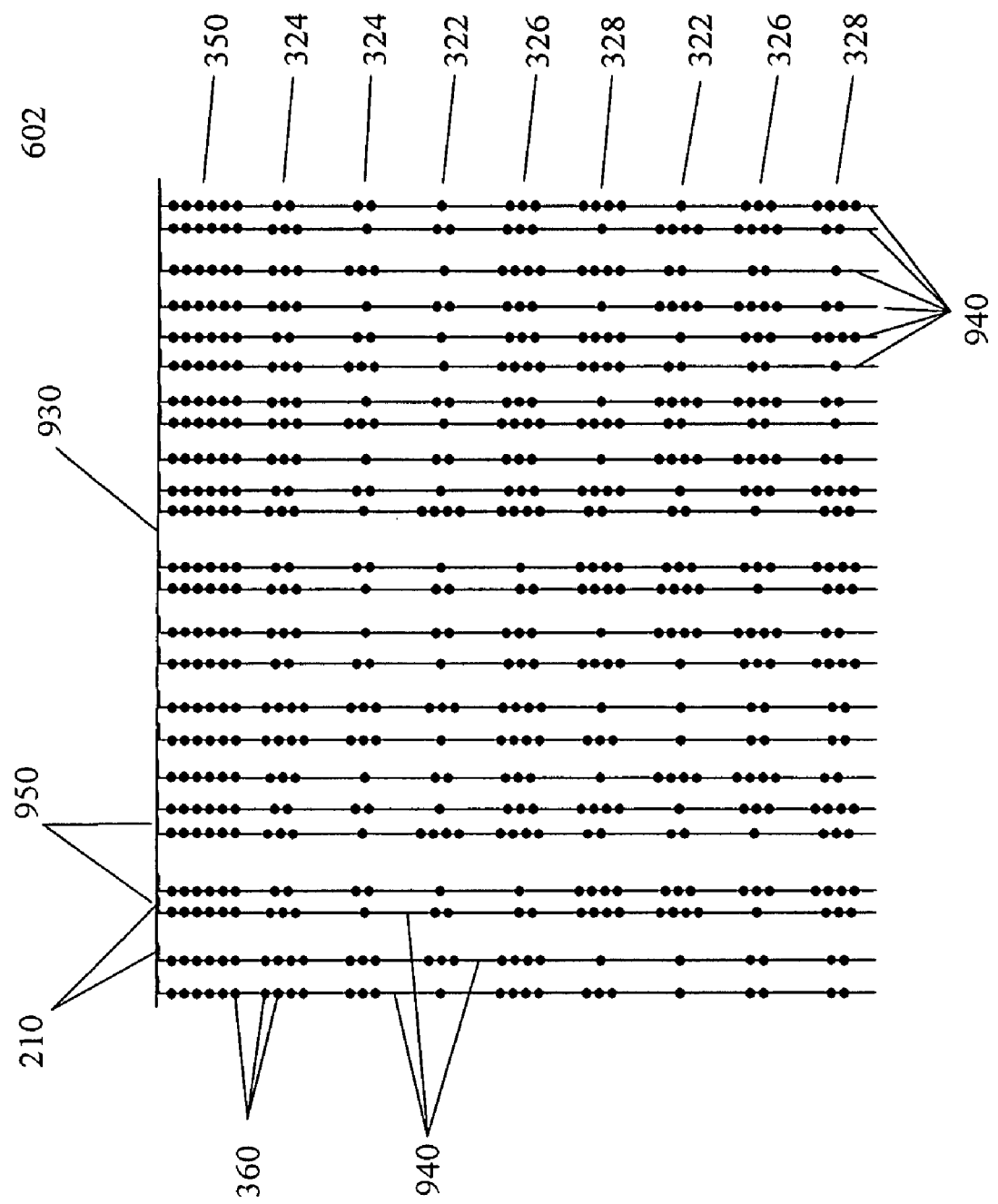

FIG. 10. Illustration of final arrangement of sample DNA and hybridized labeled-probe-assemblies with bound Lac proteins.

Figure 11:
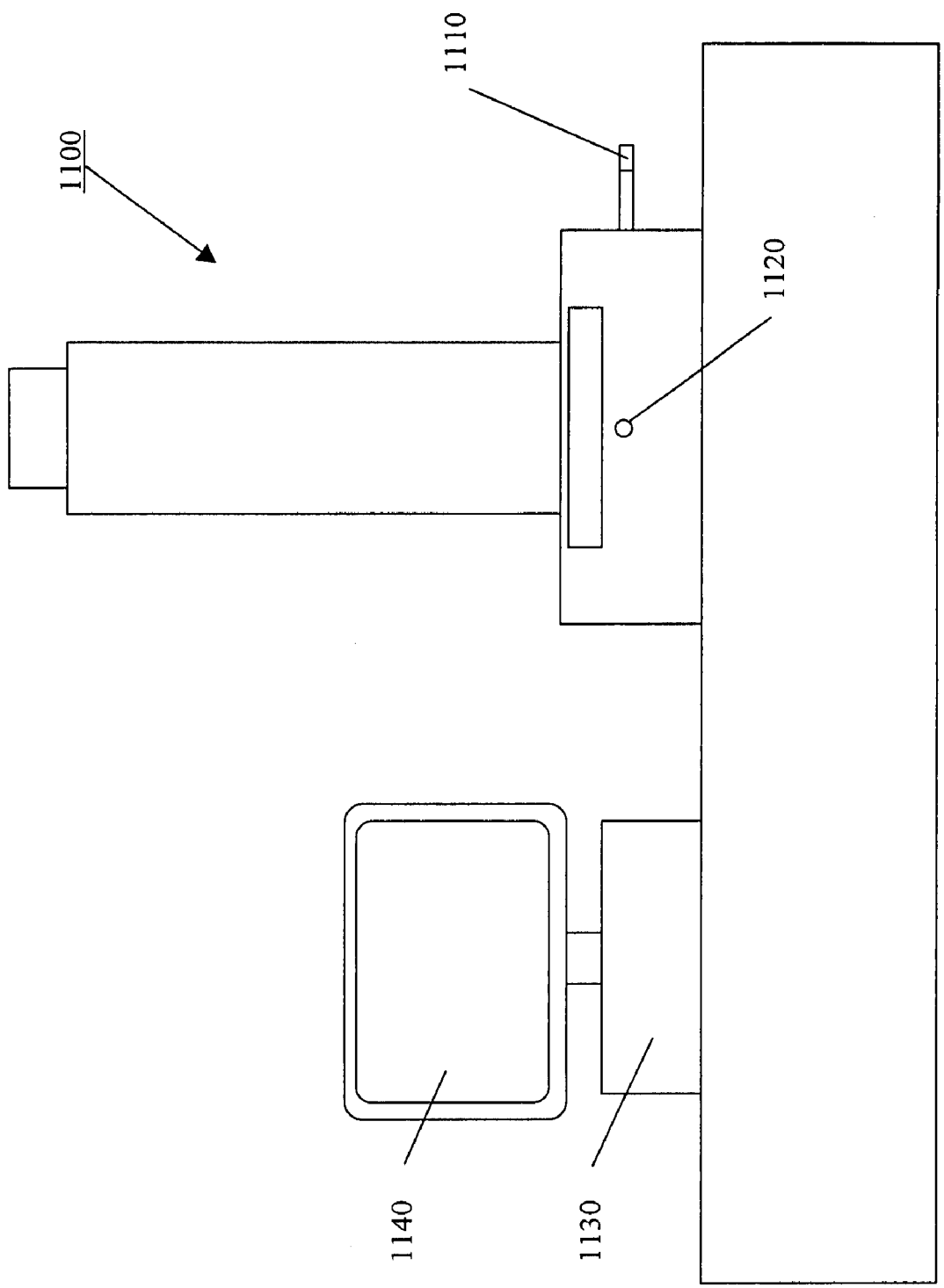

FIG. 11. Illustration of electron microscope and data acquisition system used for data readout from substrate.

Figure 12:
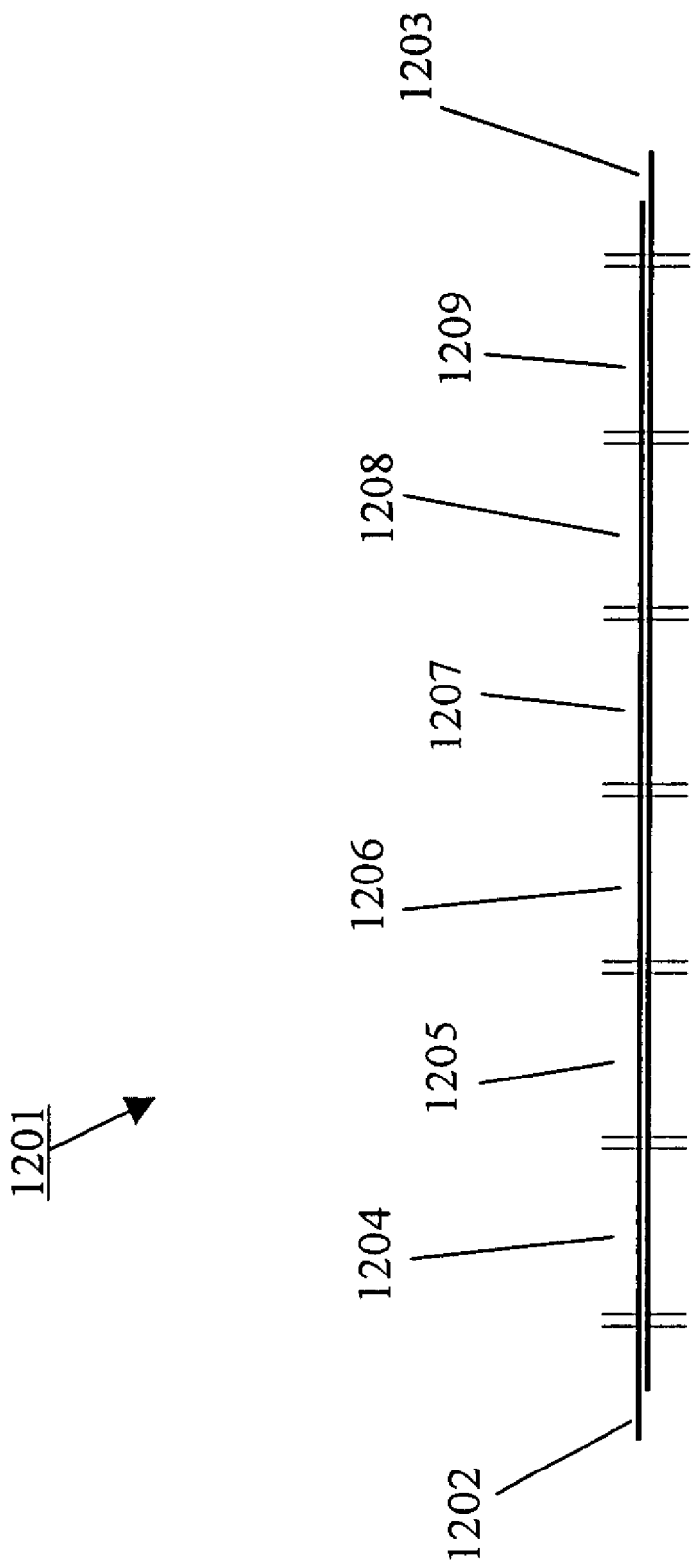

FIG. 12. Illustration of main components of alternate Labeled-probe-assembly.

Figure 13A:
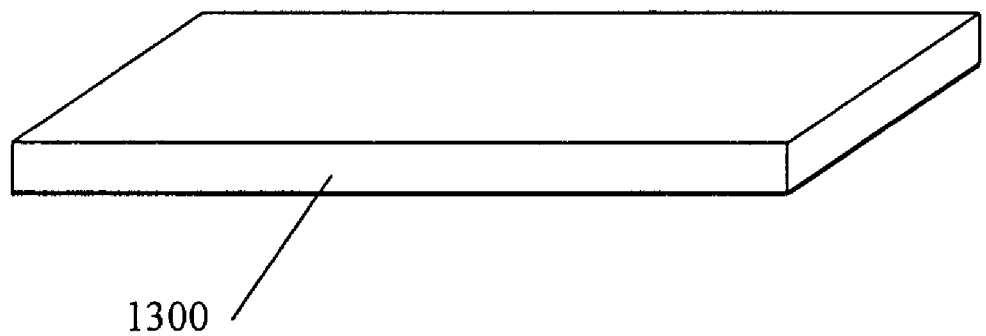

FIG. 13a. Illustration of single layer substrate.

Figure 13B:
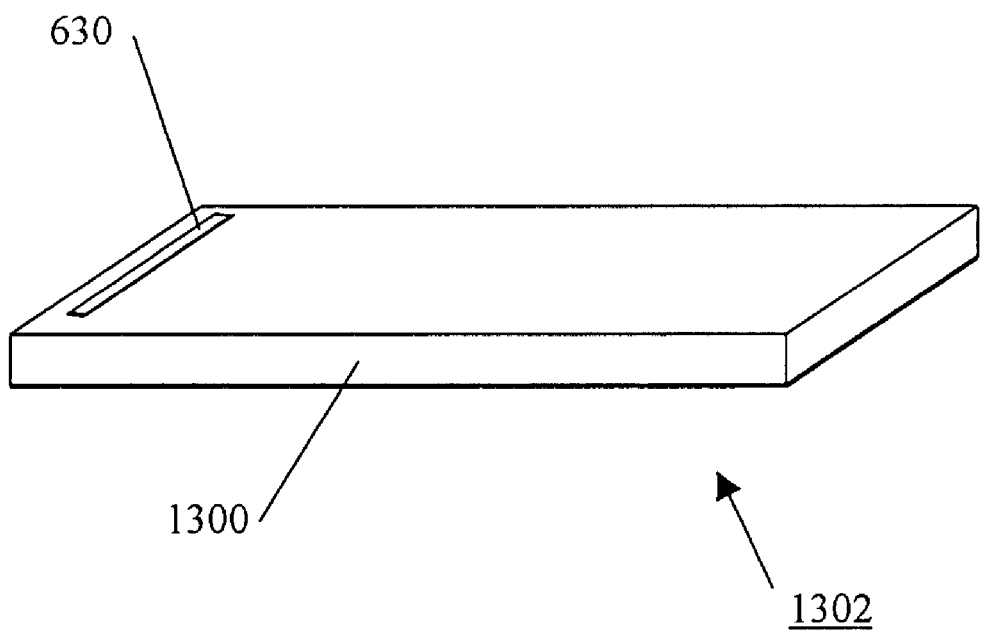

FIG. 13b. Illustration of single layer substrate with narrow strip of avidin molecules.

FIG. 14a. Illustration of apparatus for elongating substrate.

FIG. 14b. Illustration of apparatus for elongating substrate with stretchable-substrate-support over heater.

Figure 14C:
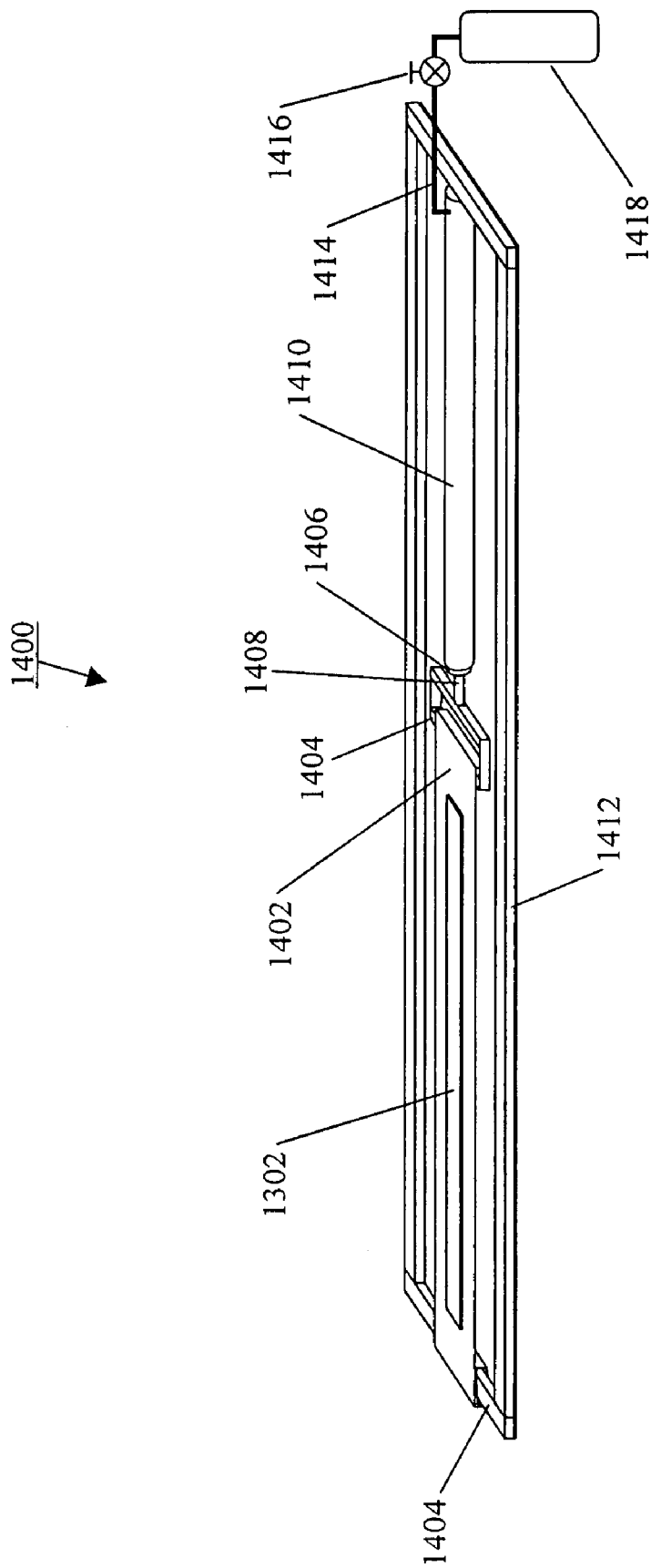

FIG. 14c. Illustration of apparatus for elongating substrate, in configuration after final elongation cycle.

Figure 15:
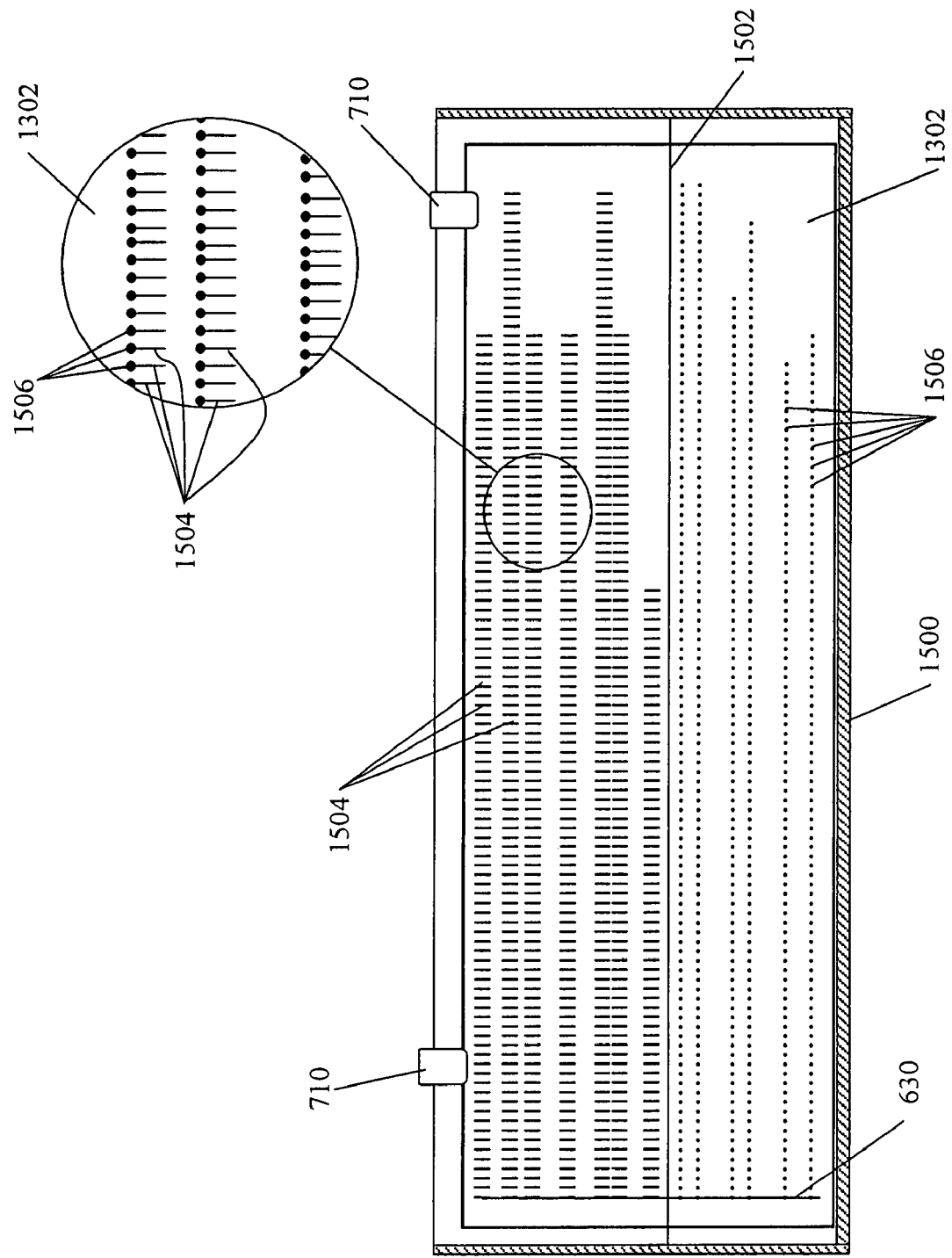

FIG. 15. Front view cut-away of apparatus for extending labeled-probe-assemblies over elongated substrate, part way through process of extending labeled-probe-assemblies, with close-up view.

Figure 16:
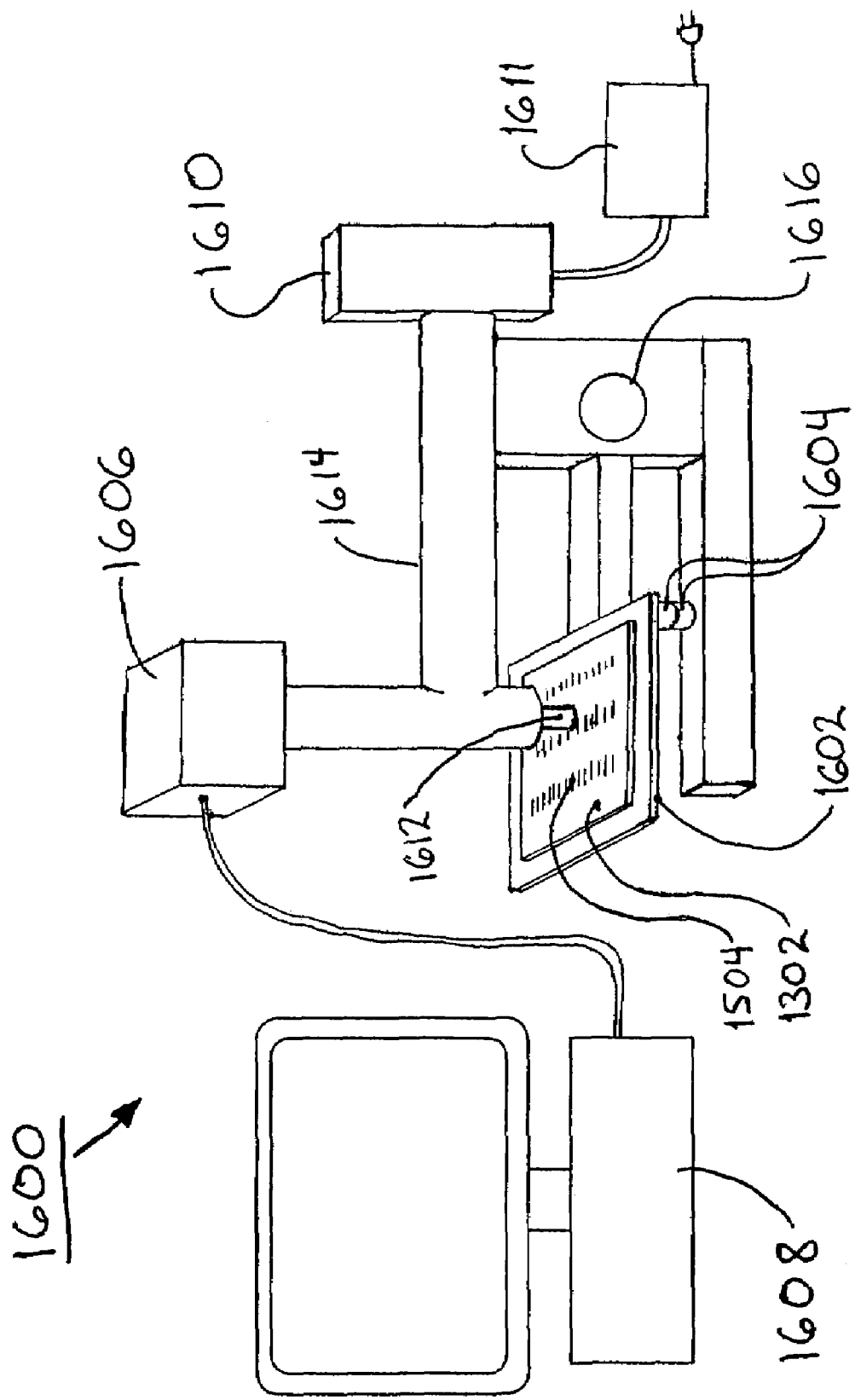

FIG. 16. Illustration of microscope and data acquisition system used for data readout from substrate.

Figure 17:
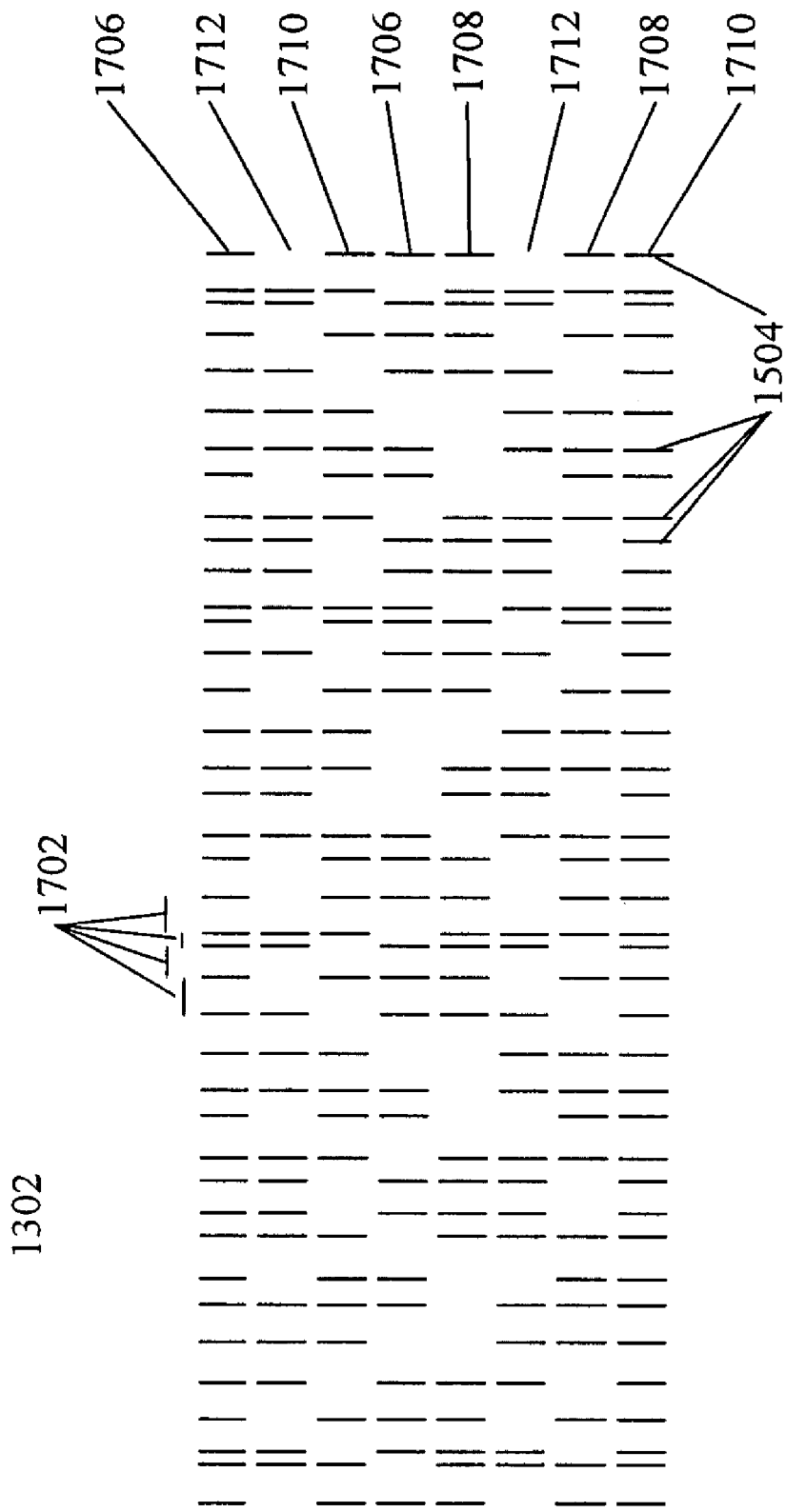

FIG. 17. Illustration of image recorded by fluorescent microscope data readout apparatus.

Figure 18:
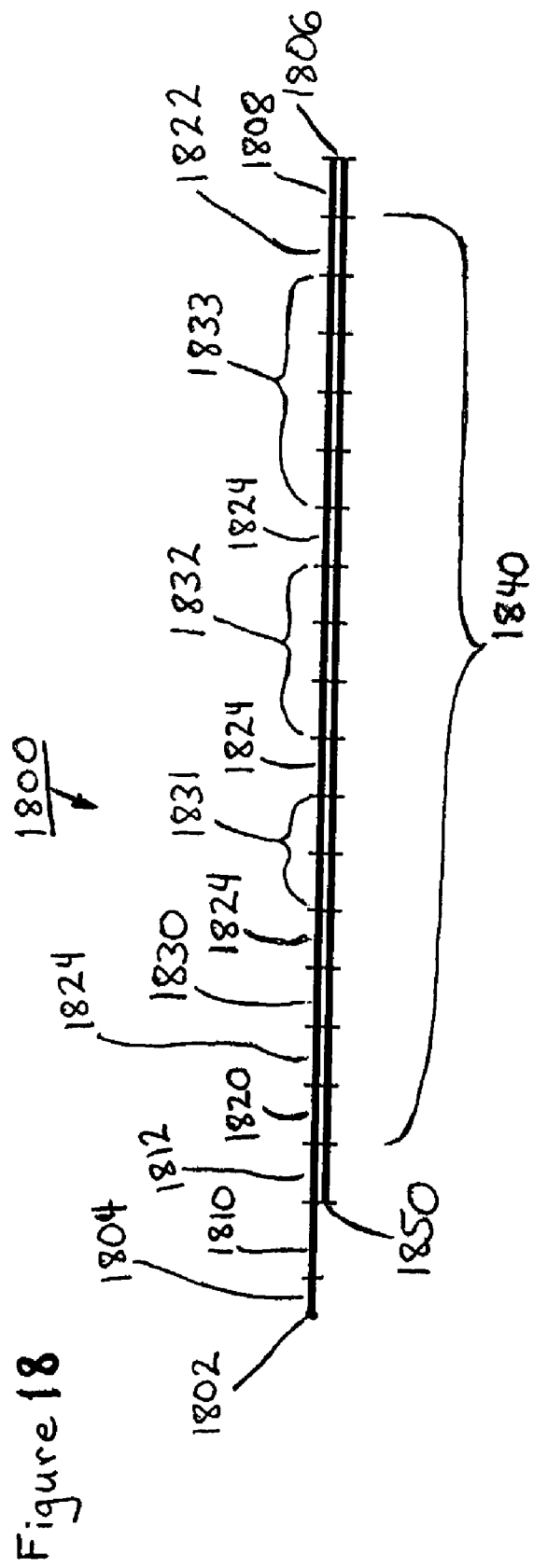

FIG. 18. Illustration of main components of a further alternate labeled-probe-assembly.

Figure 19:
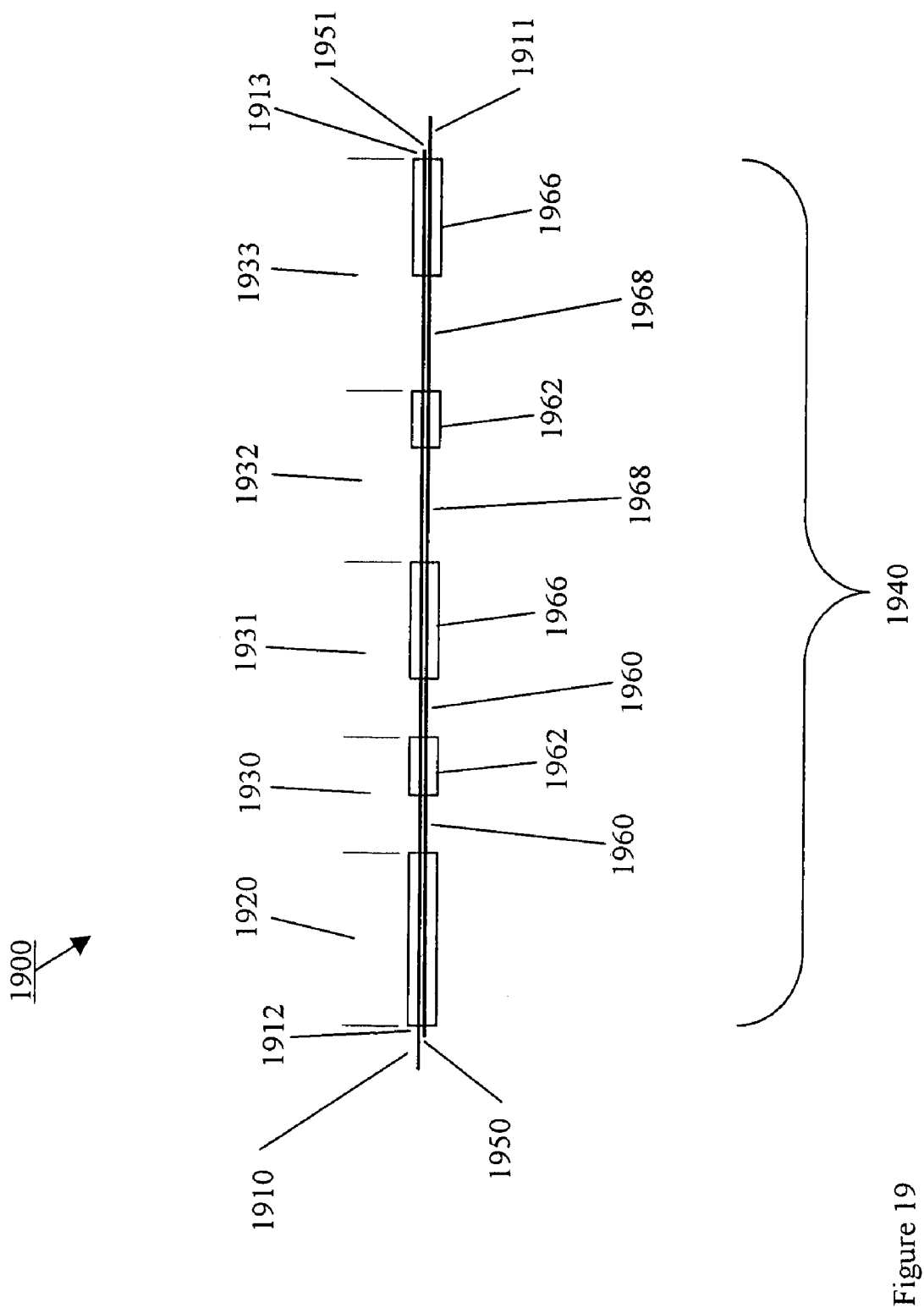

FIG. 19. Illustration of main components of a further alternate labeled-probe-assembly.

Figure 20:
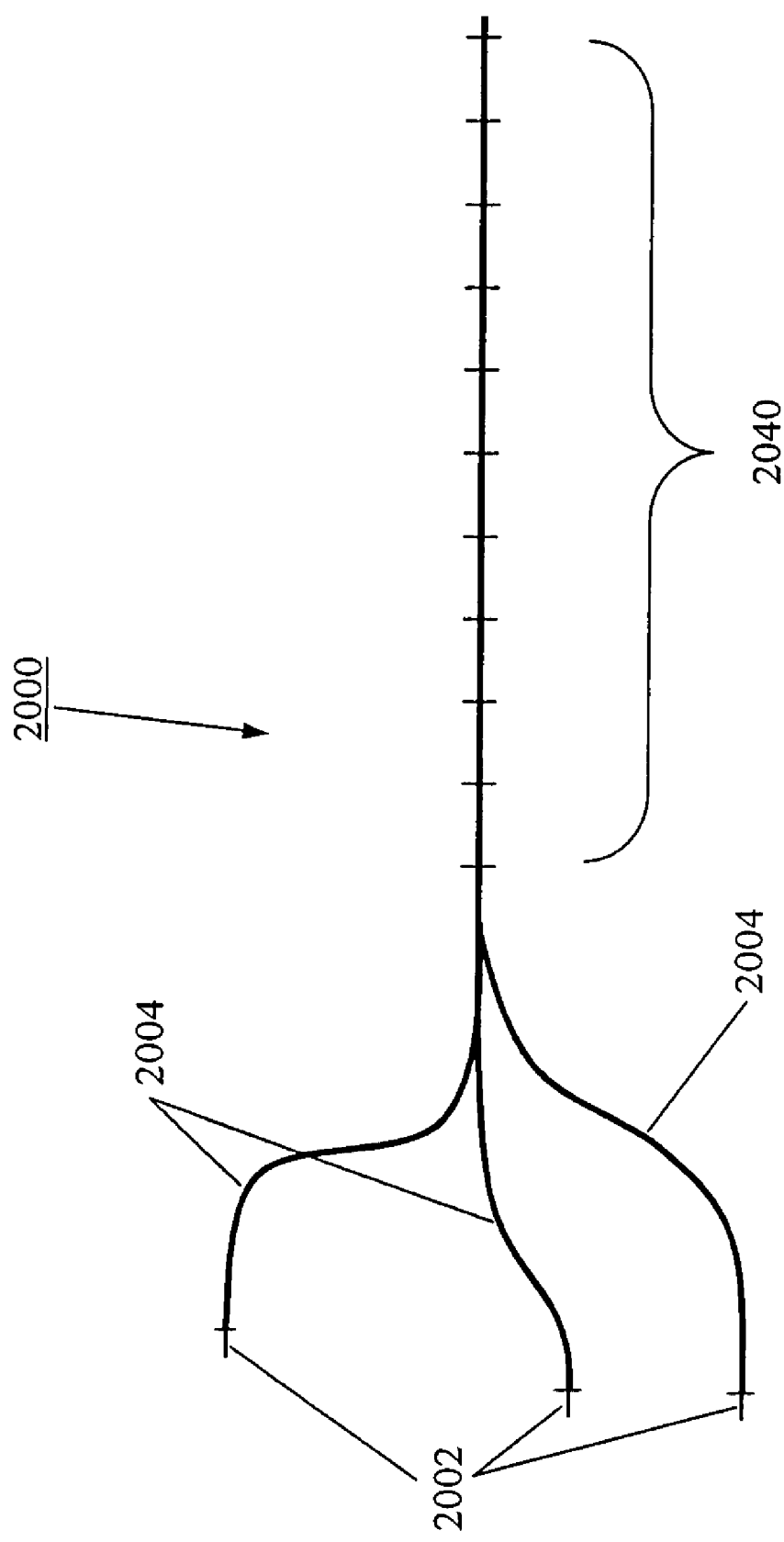

FIG. 20. Illustration of main components of multi-probe labeled-probe-assembly.

Figure 21:
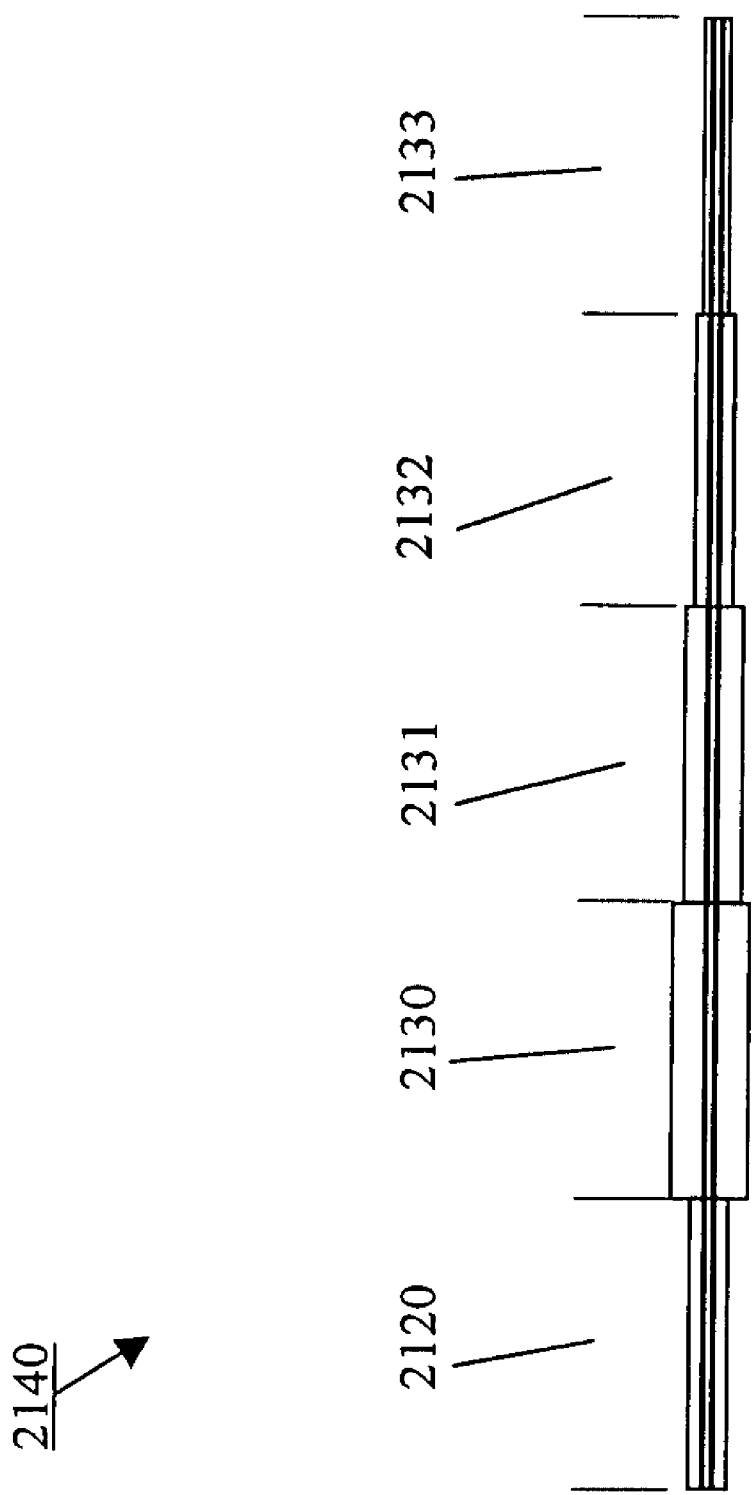

FIG. 21. Illustration of main components of a labeled-assembly using a further alternate information encoding protocol.

Figure 22:
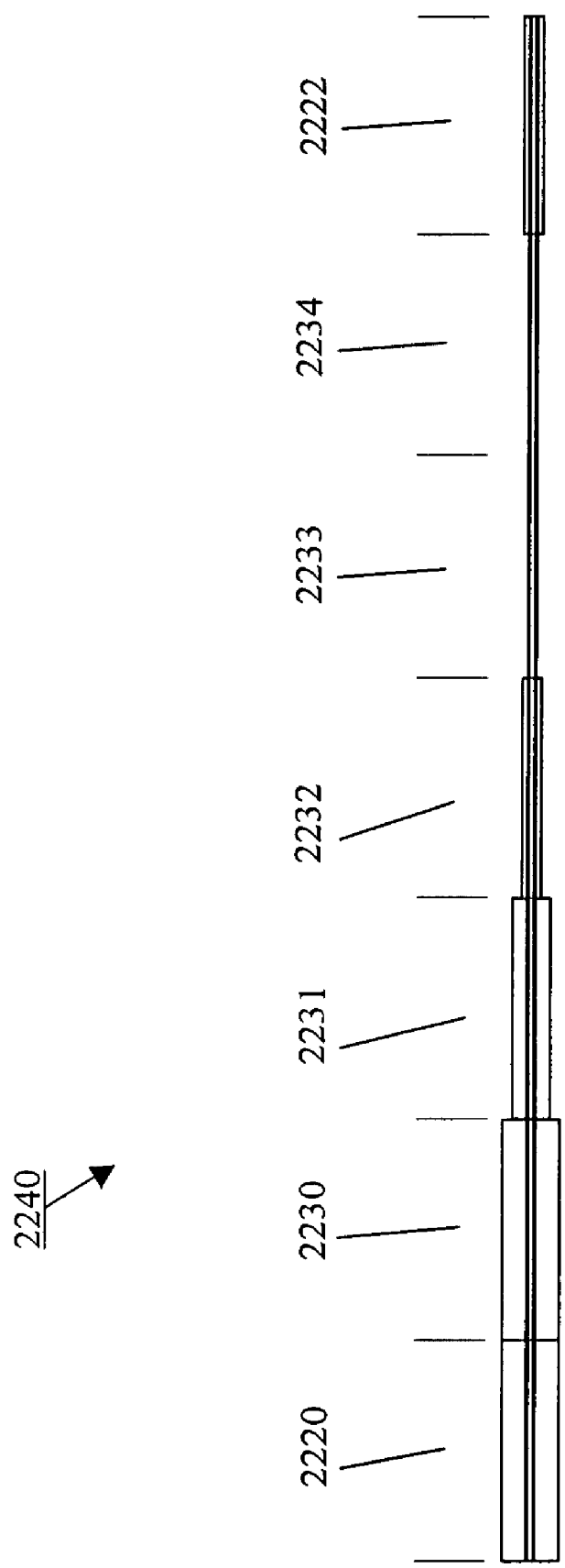

FIG. 22. Illustration of main components of a labeled-assembly using a further alternate information encoding protocol.

Figure 23:
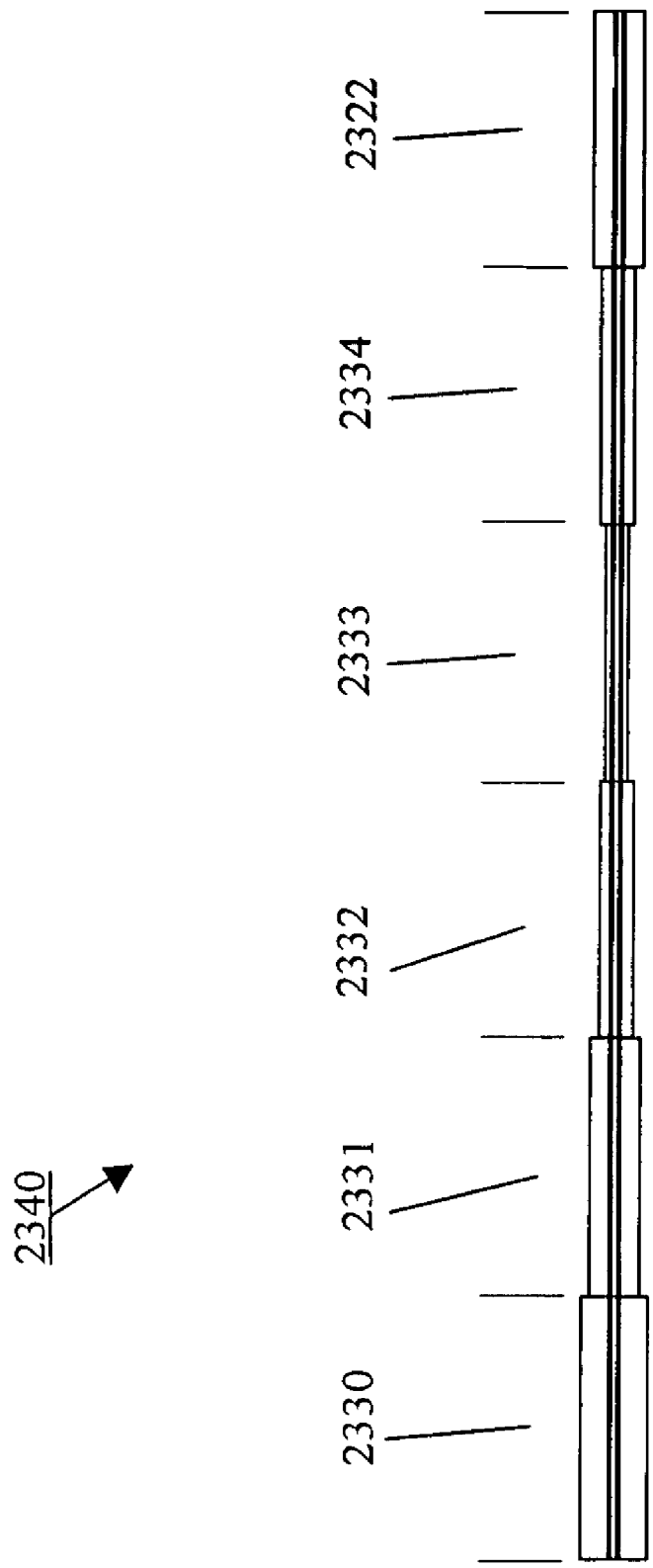

FIG. 23. Illustration of main components of a labeled-assembly using a further alternate information encoding protocol.

Figure 24:
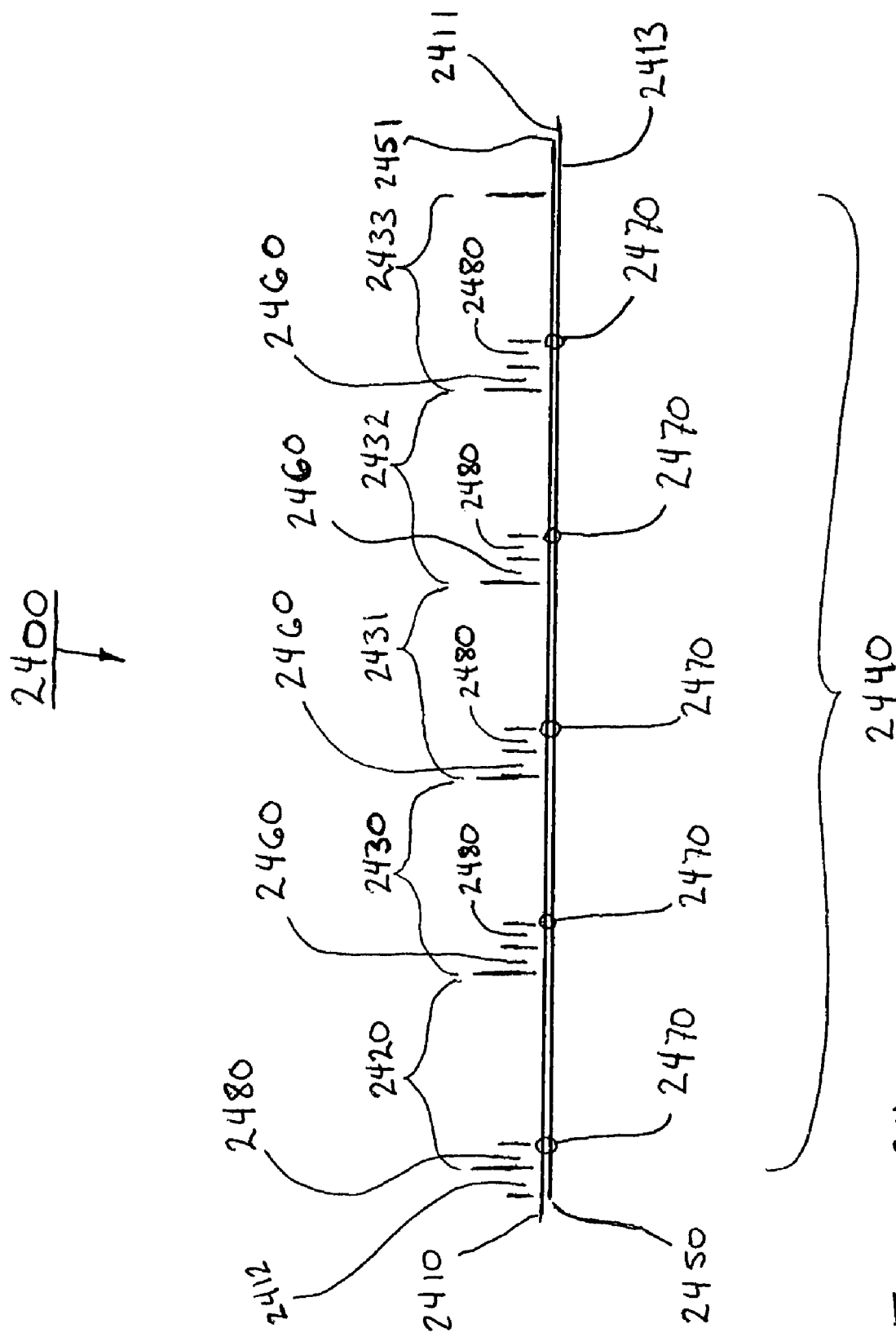

FIG. 24. Illustration of main components of a further alternate labeled-probe-assembly.

Figure 25:
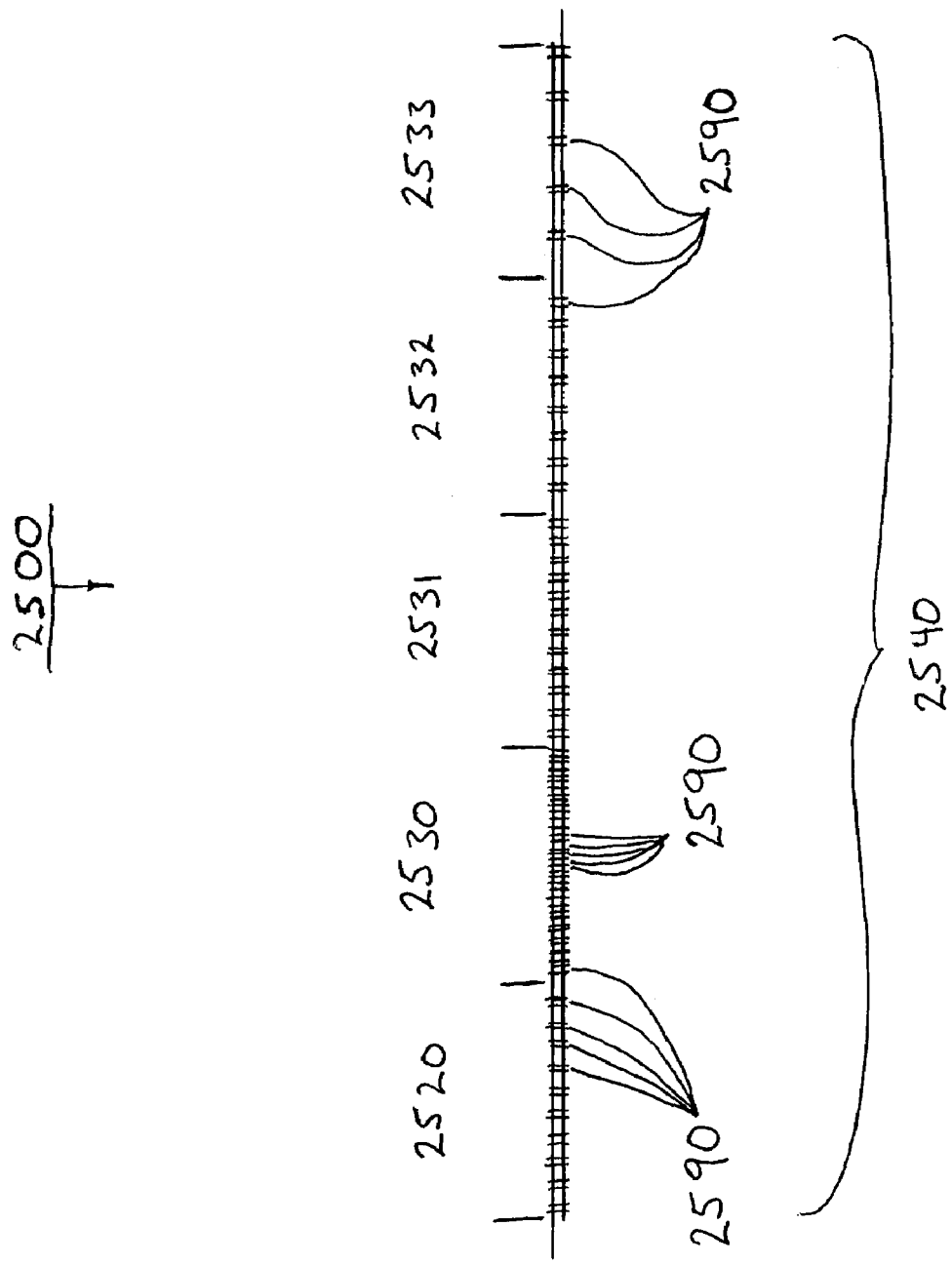

FIG. 25. Illustration of main components of a further alternate labeled-probe-assembly.

Figure 26:
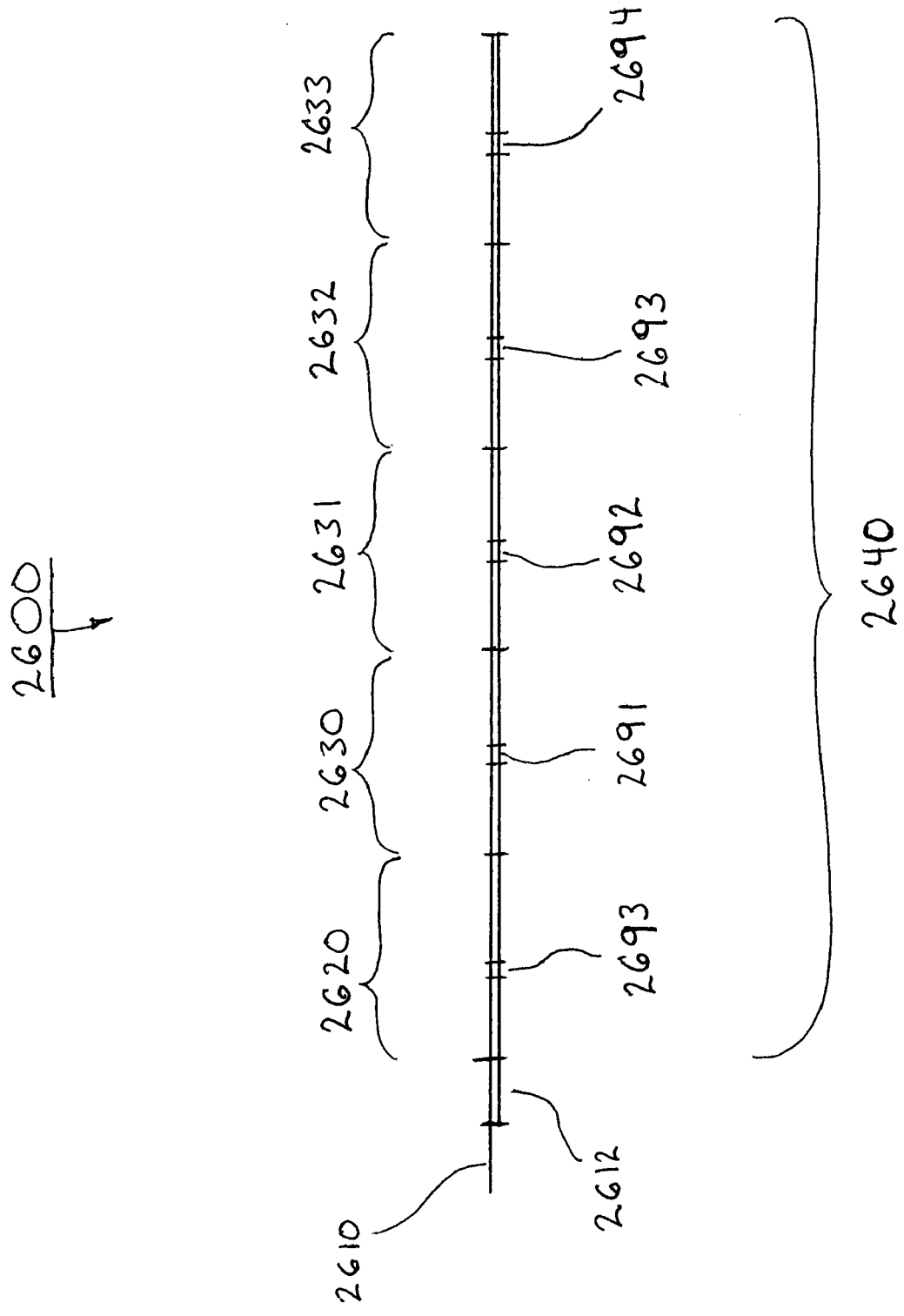

FIG. 26. Illustration of main components of a further alternate labeled-probe-assembly.

Figure 27:
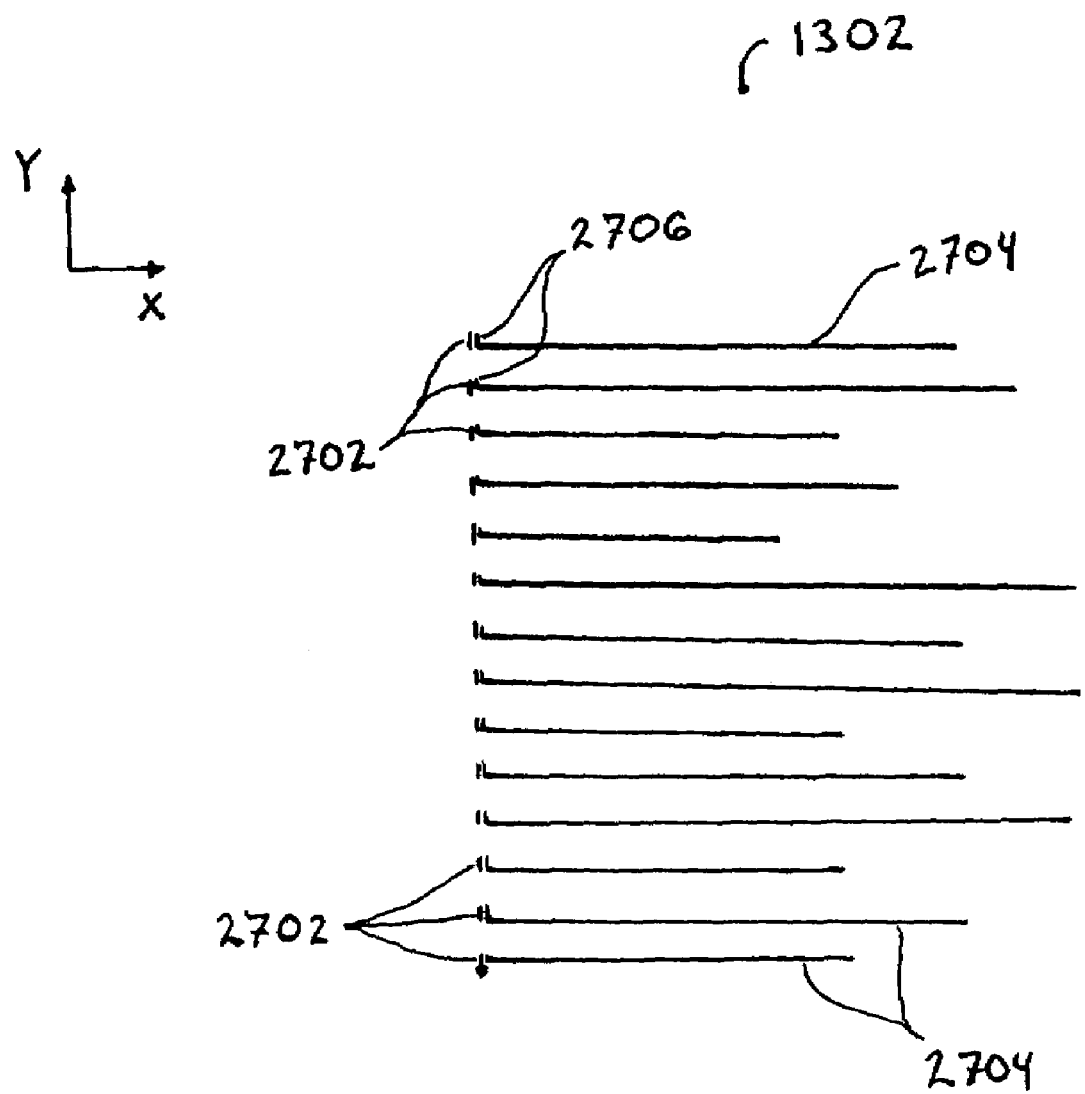

FIG. 27. Illustration of arrangement of sample DNA and hybridized labeled-probe-assemblies on portion of substrate.

FIG. 28. Illustration of arrangement of sample DNA on portion of substrate.

FIG. 29. Illustration of arrangement of sample DNA on portion of substrate, after substrate elongation.

FIG. 30. Illustration of arrangement of sample DNA on portion of substrate, after substrate elongation and hybridization of labeled-probe-assemblies.

FIG. 31. Illustration of arrangement of sample DNA on portion of substrate, after substrate elongation, hybridization of labeled-probe-assemblies, and extension of labeled-probe-assemblies.

Figure 32:
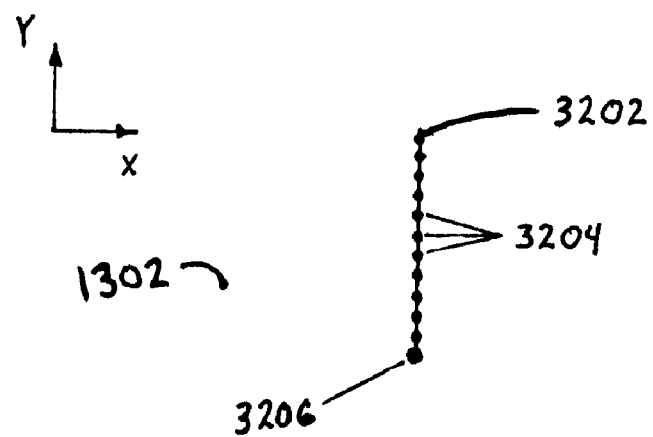

FIG. 32. Illustration of arrangement of sample DNA on portion of substrate.

Figure 33:
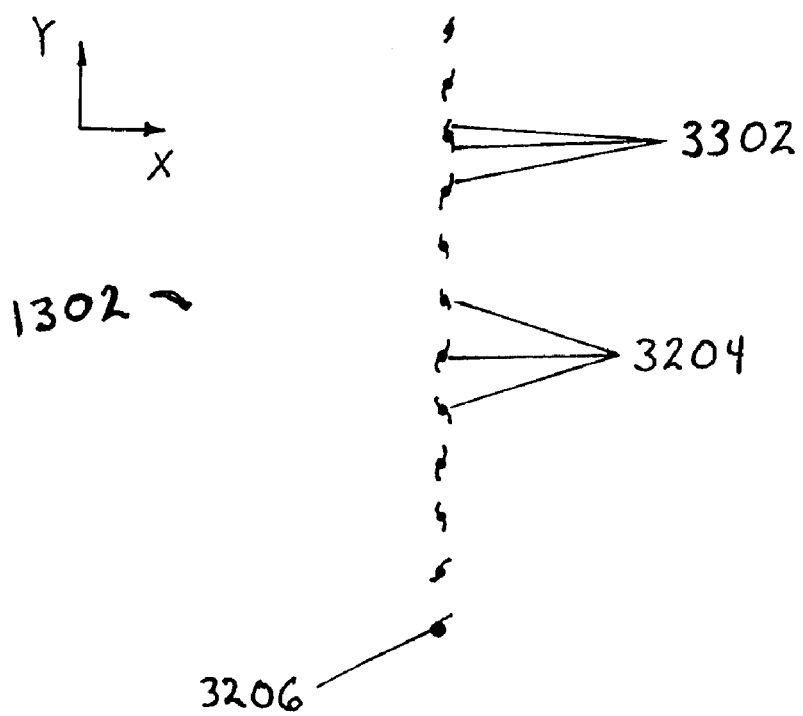

FIG. 33. Illustration of arrangement of sample DNA on portion of substrate, after substrate elongation.

Figure 34:
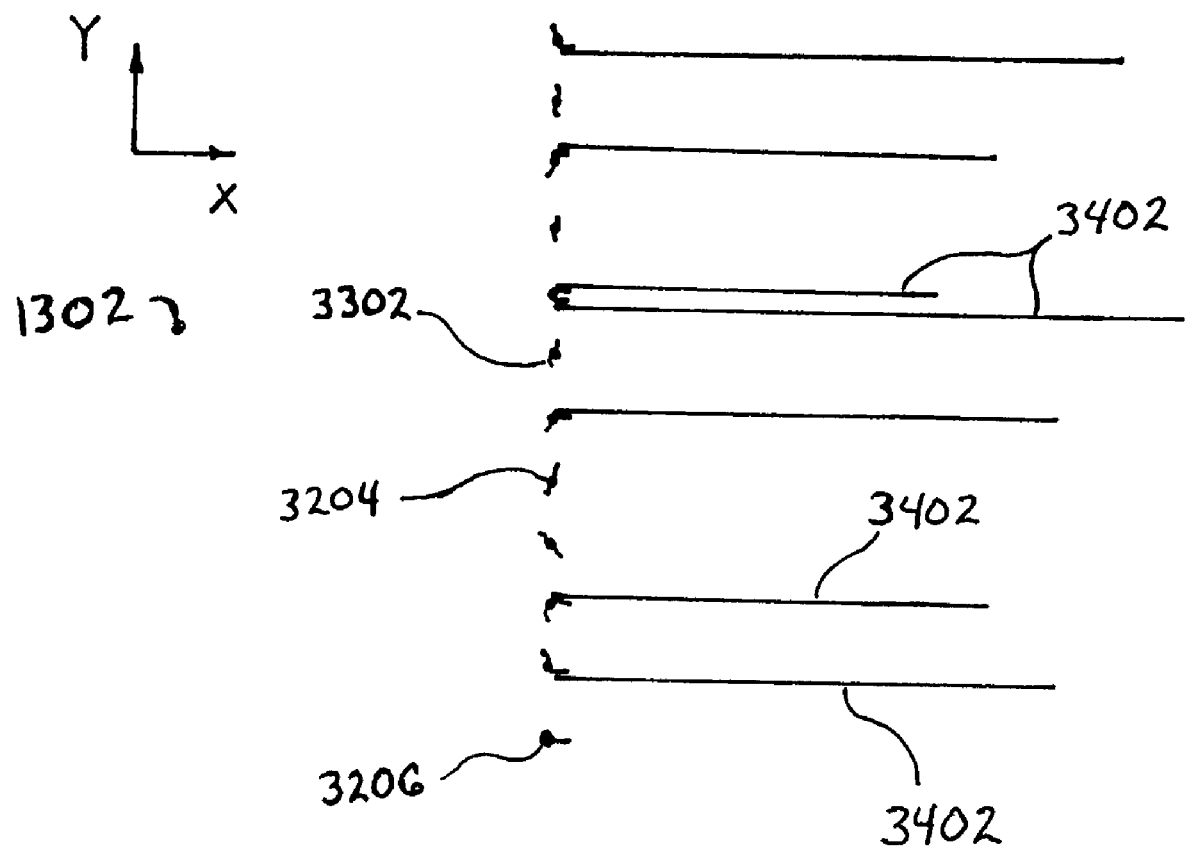

FIG. 34. Illustration of arrangement of sample DNA on portion of substrate, after substrate elongation, hybridization of first set of labeled-probe-assemblies, and extension of labeled-probe-assemblies in one direction.

Figure 35:
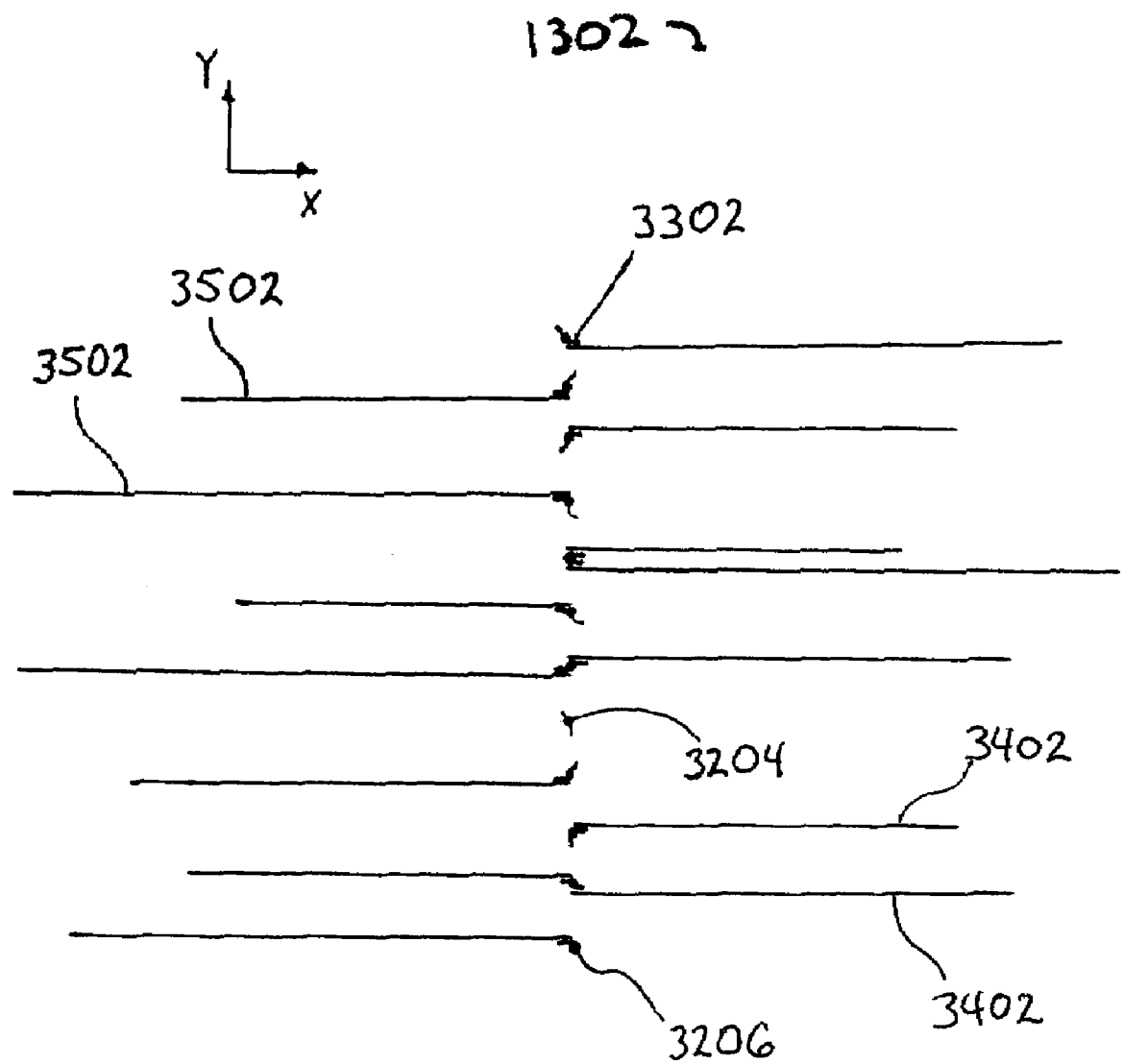

FIG. 35. Illustration of arrangement of sample DNA on portion of substrate, after hybridization of second set of labeled-probe-assemblies, and extension of second set of labeled-probe-assemblies in direction opposite that of first set.

Figure 36:
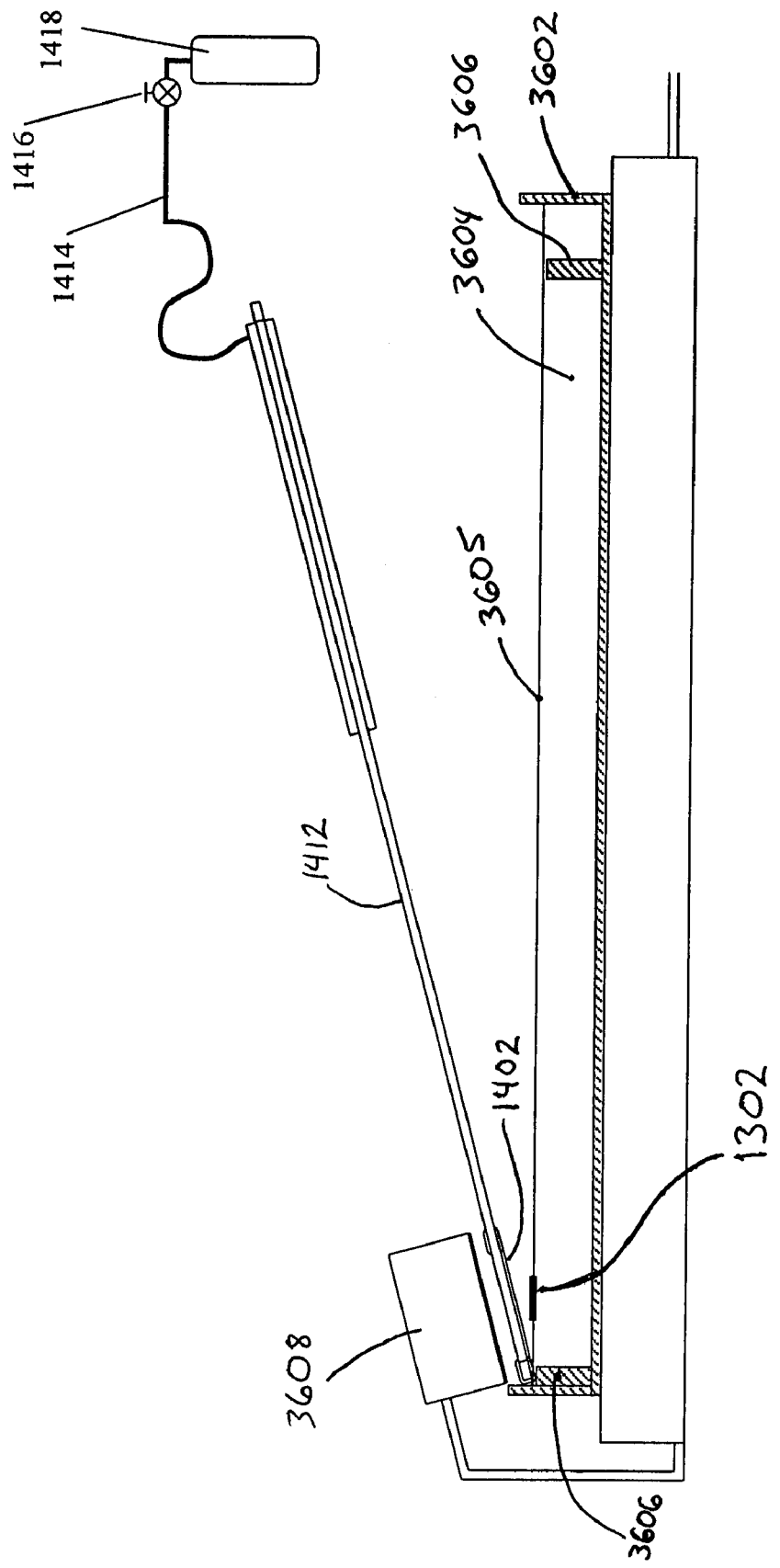

FIG. 36. Illustration of alternate apparatus for elongating substrate with stretchable-substrate-support near heater.

Figure 37:
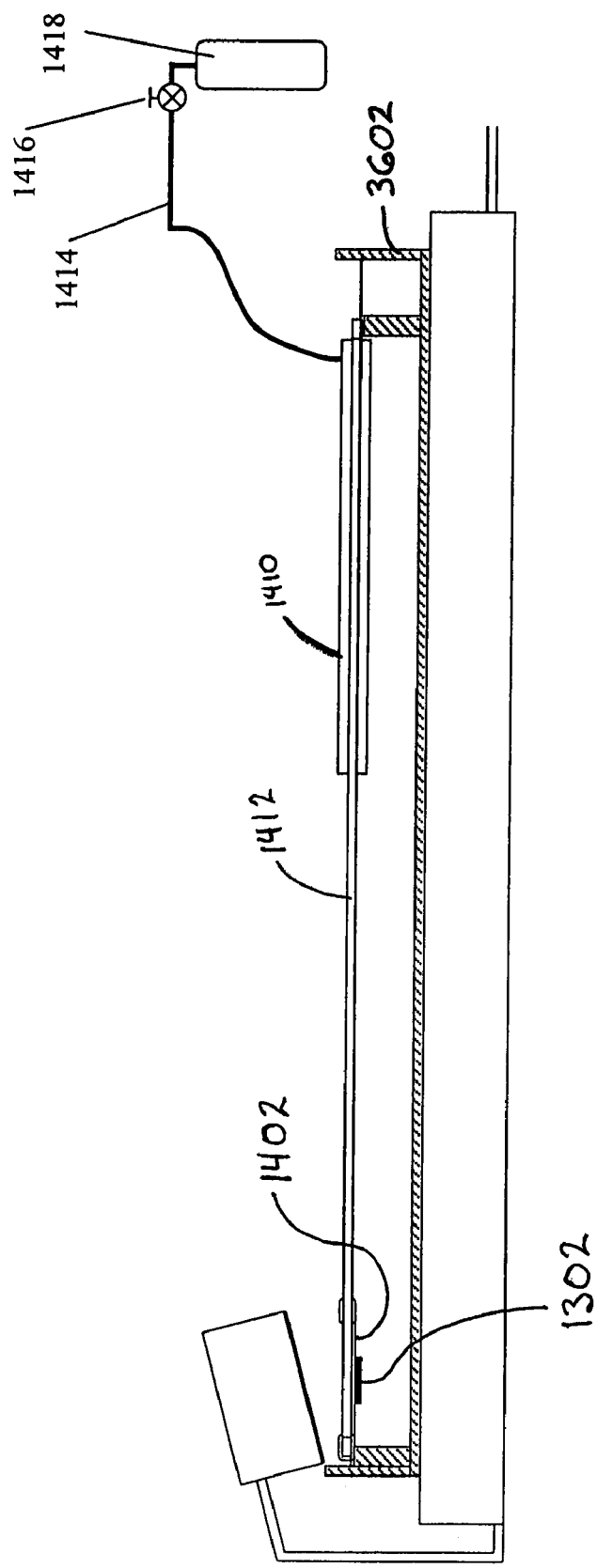

FIG. 37. Illustration of alternate apparatus for elongating substrate with stretchable-substrate-support contacting substrate.

Figure 38:
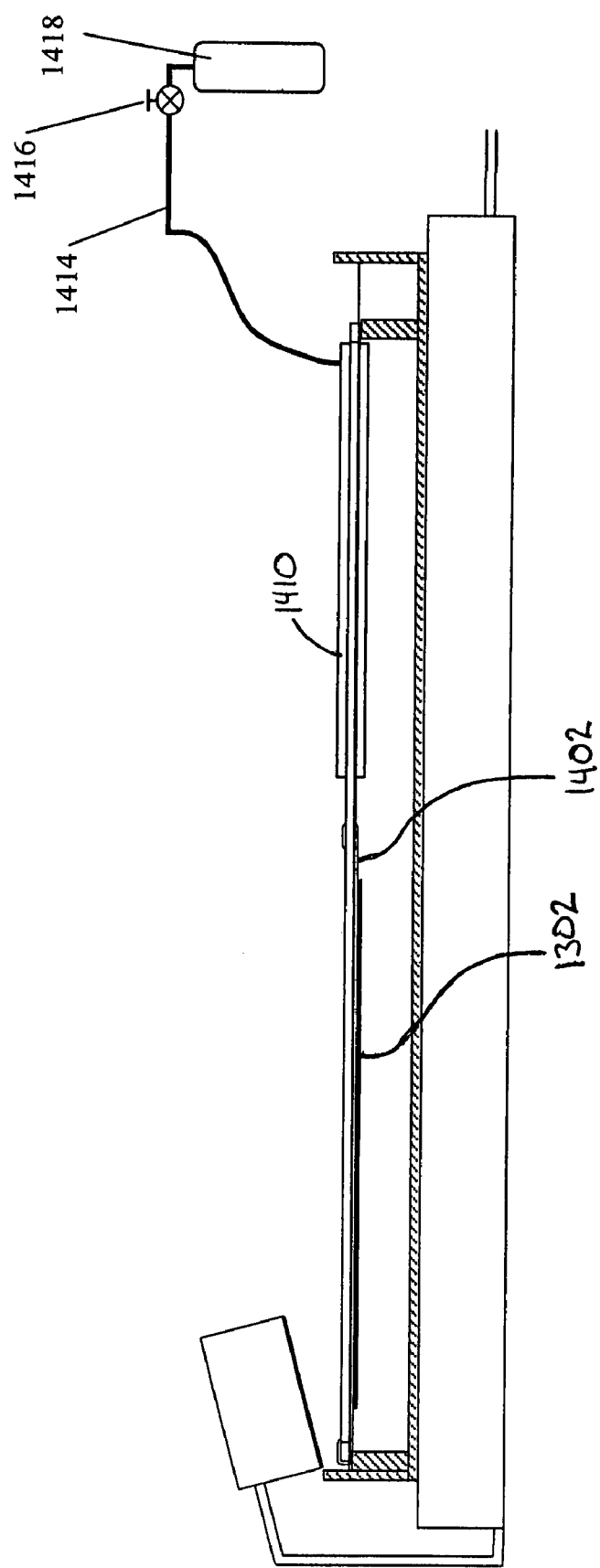

FIG. 38. Illustration of alternate apparatus for elongating substrate, in configuration after elongation cycle.

Figure 39:
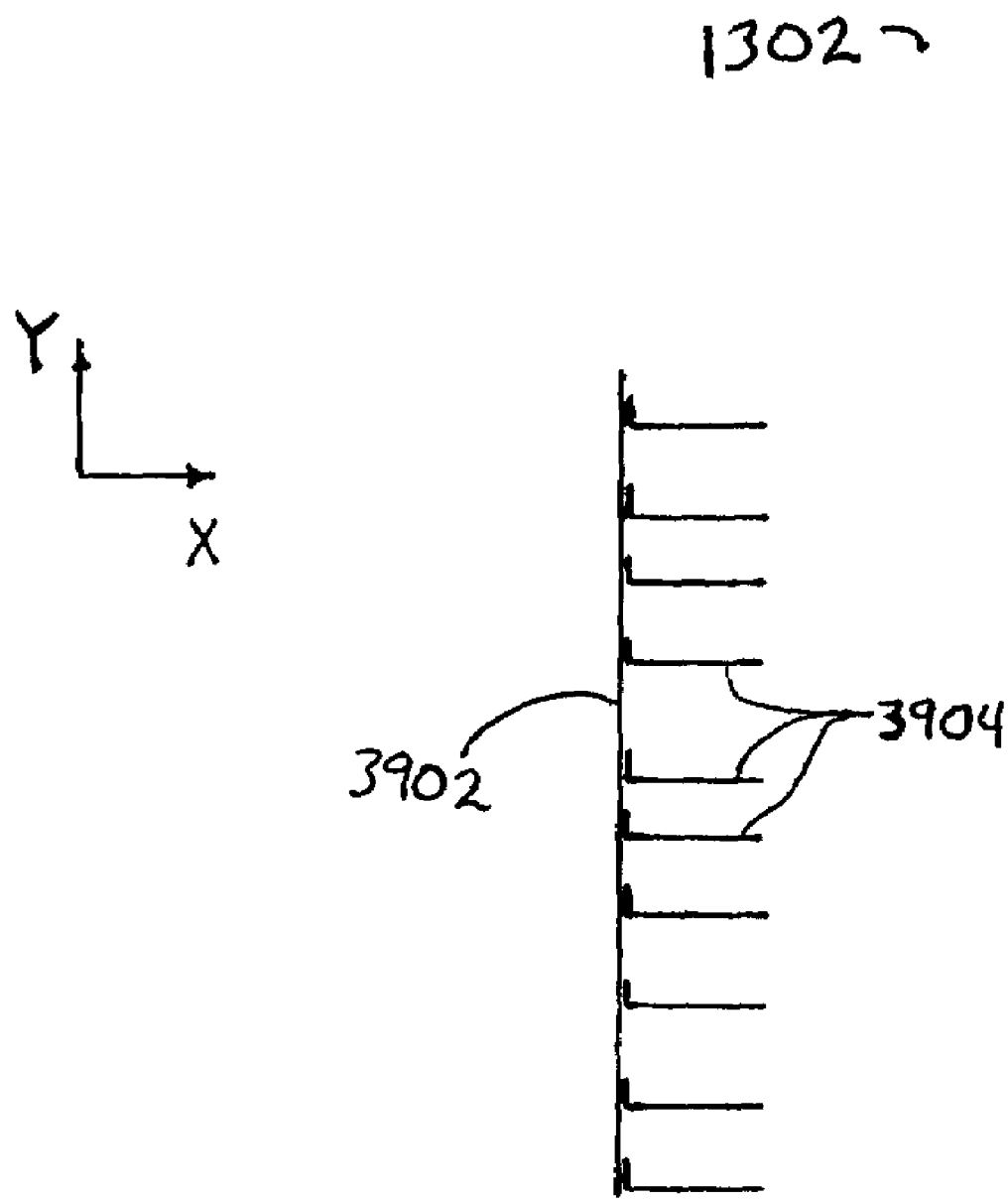

FIG. 39. Illustration of arrangement of sample DNA and hybridized and extended labeled-probe-assemblies on portion of substrate.

Figure 40:
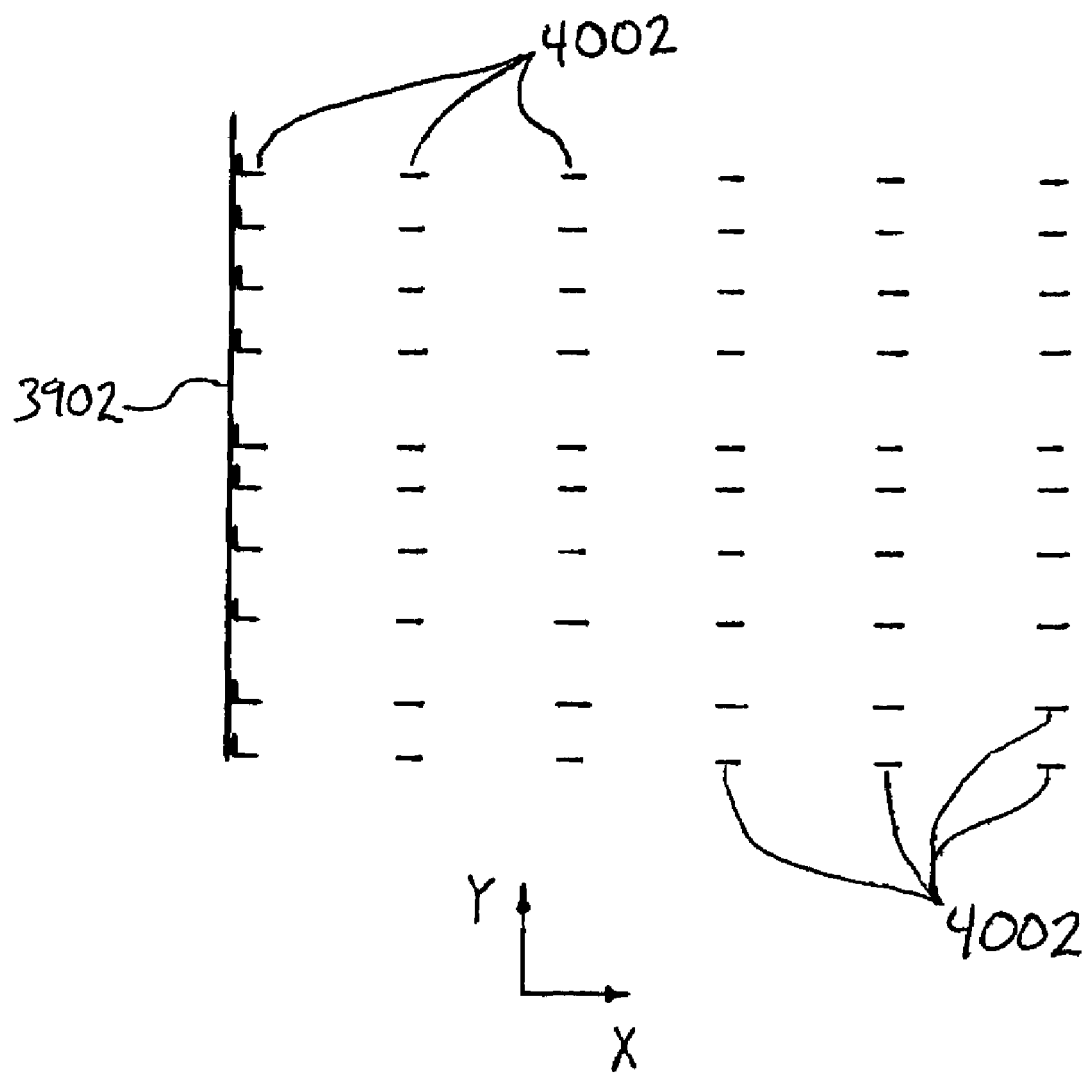

FIG. 40. Illustration of arrangement of sample DNA and hybridized and extended labeled-probe-assemblies on portion of substrate, after elongation of substrate to separate sections of labeled-probe-assemblies between cleavable-linkers.

Figure 41:
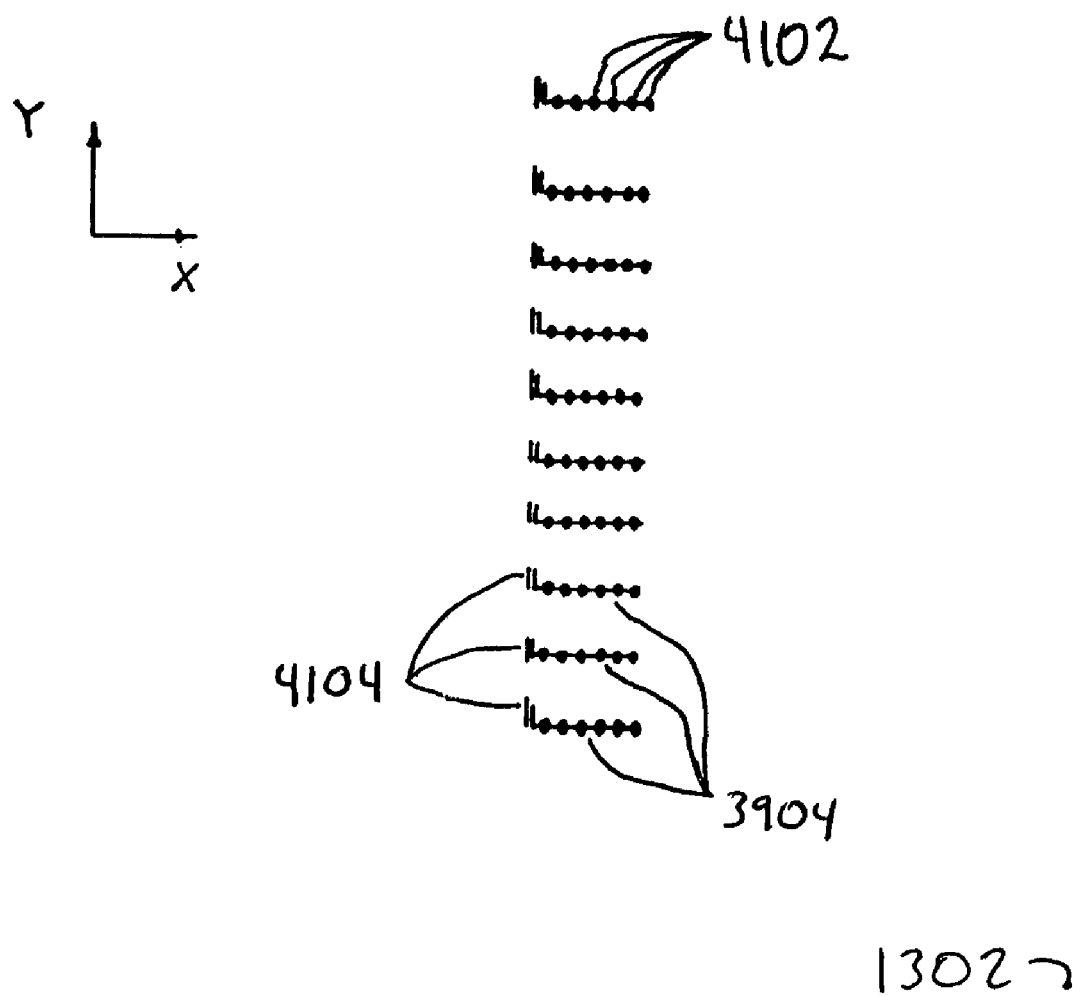

FIG. 41. Illustration of arrangement of sample DNA, hybridized and extended labeled-probe-assemblies, and DNA-binding proteins on portion of substrate.

Figure 42:
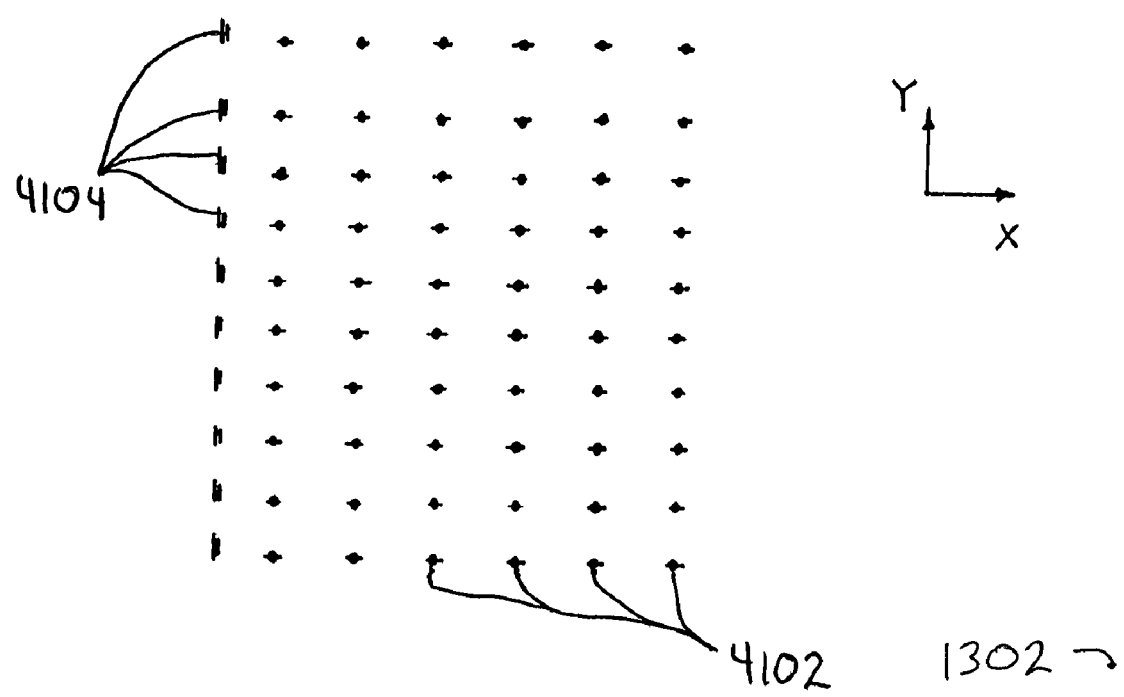

FIG. 42. Illustration of arrangement of sample DNA, hybridized and extended labeled-probe-assemblies, and DNA-binding proteins on portion of substrate, after elongation of substrate to separate substrate-bound DNA-binding proteins.

Figure 43:
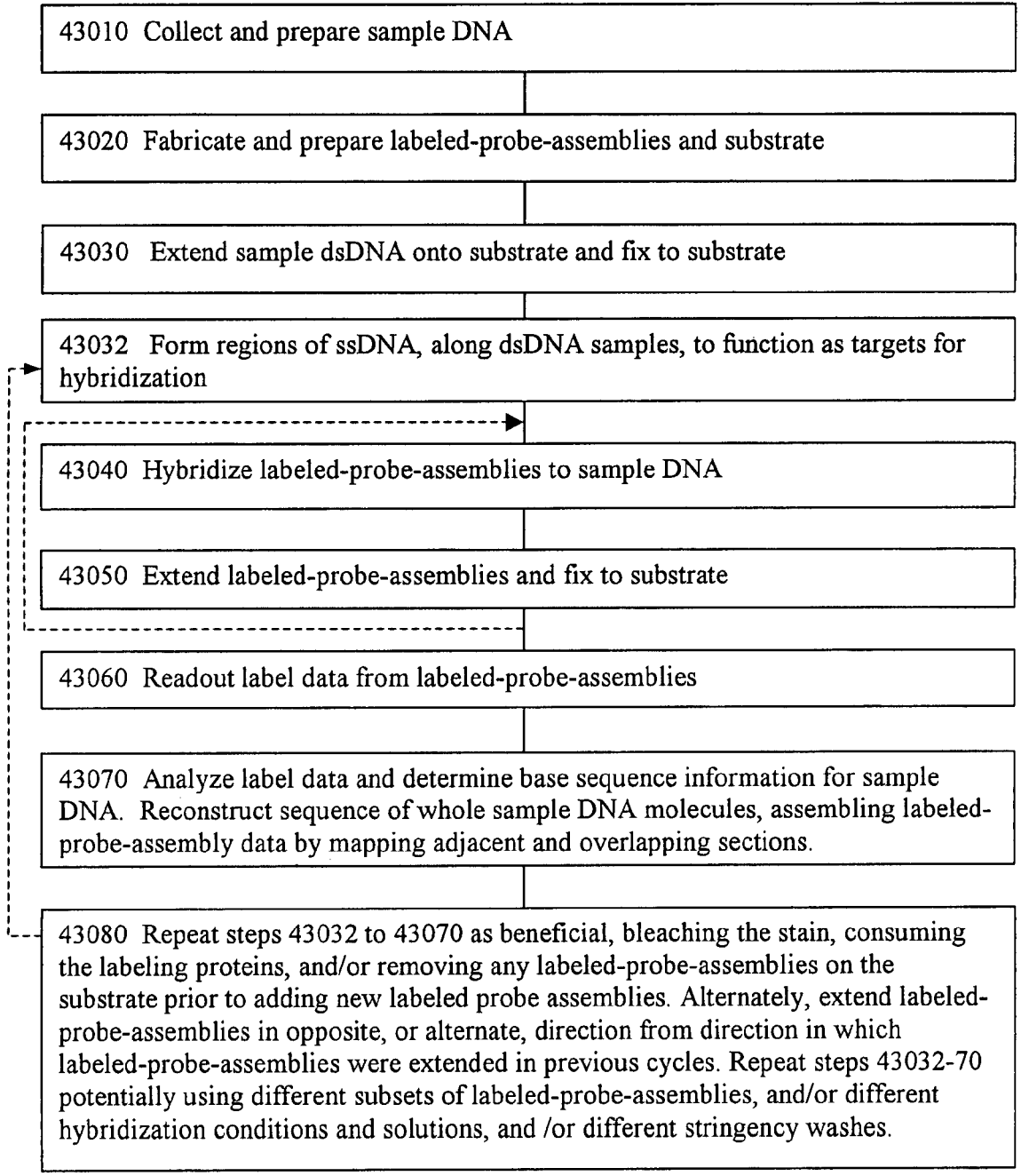

FIG. 43. Process flow diagram for preferred embodiment of method for sequencing of DNA using labeled-probe-assemblies.

Figure 44:
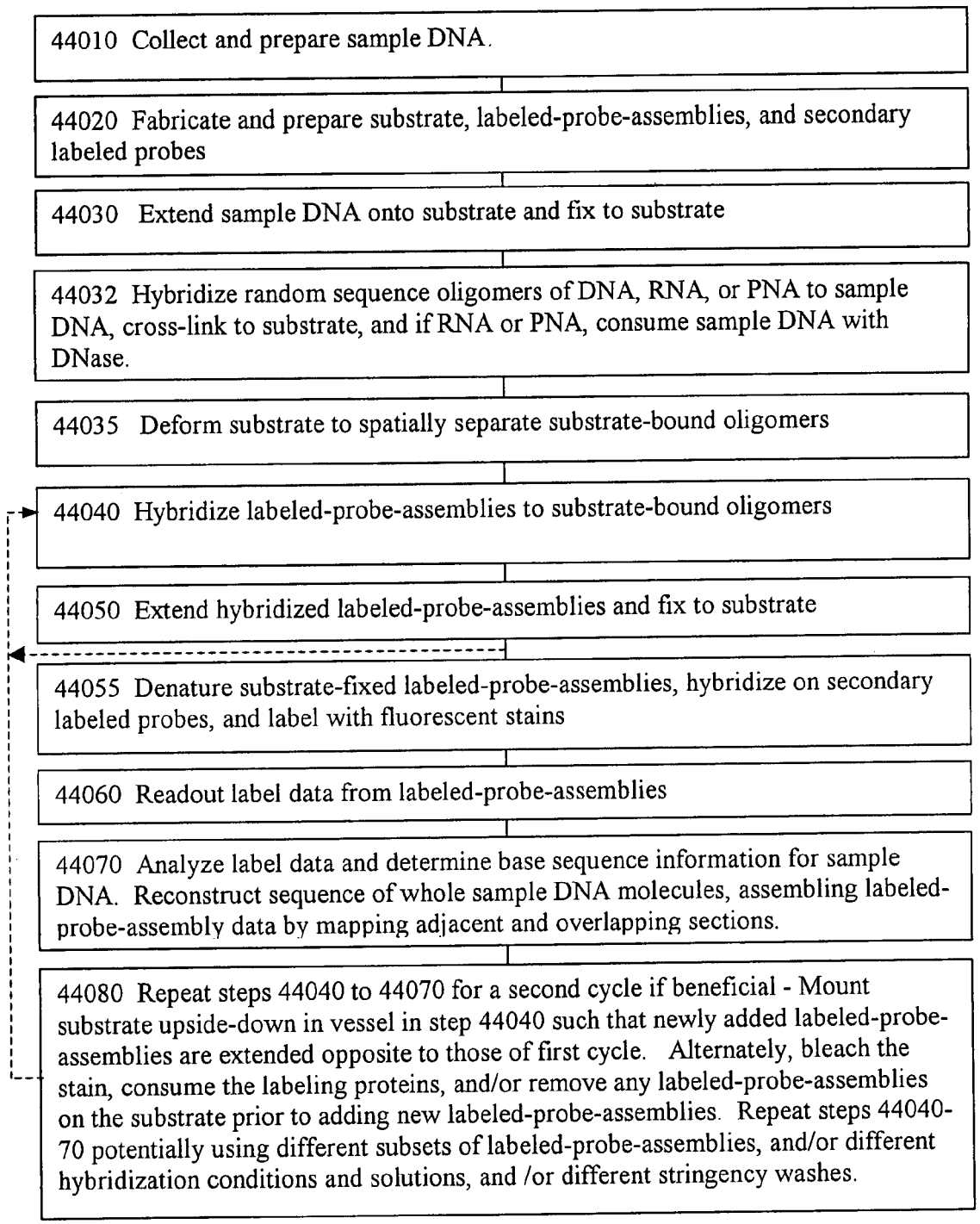

FIG. 44. Process flow diagram for alternate method for sequencing of DNA using labeled-probe-assemblies.

Figure 45:
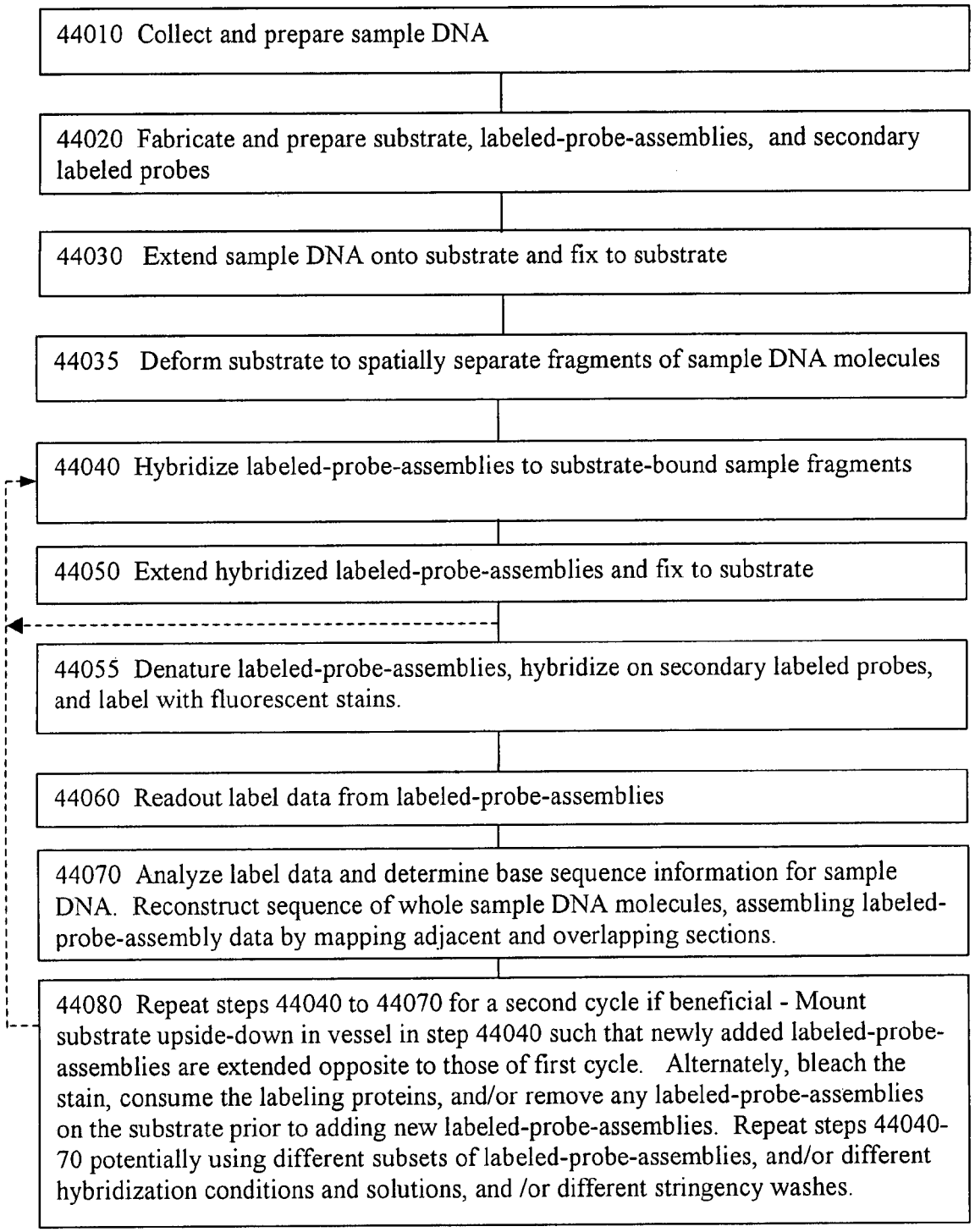

FIG. 45. Process flow diagram for further alternate method for sequencing of DNA using labeled-probe-assemblies.

Figure 46:
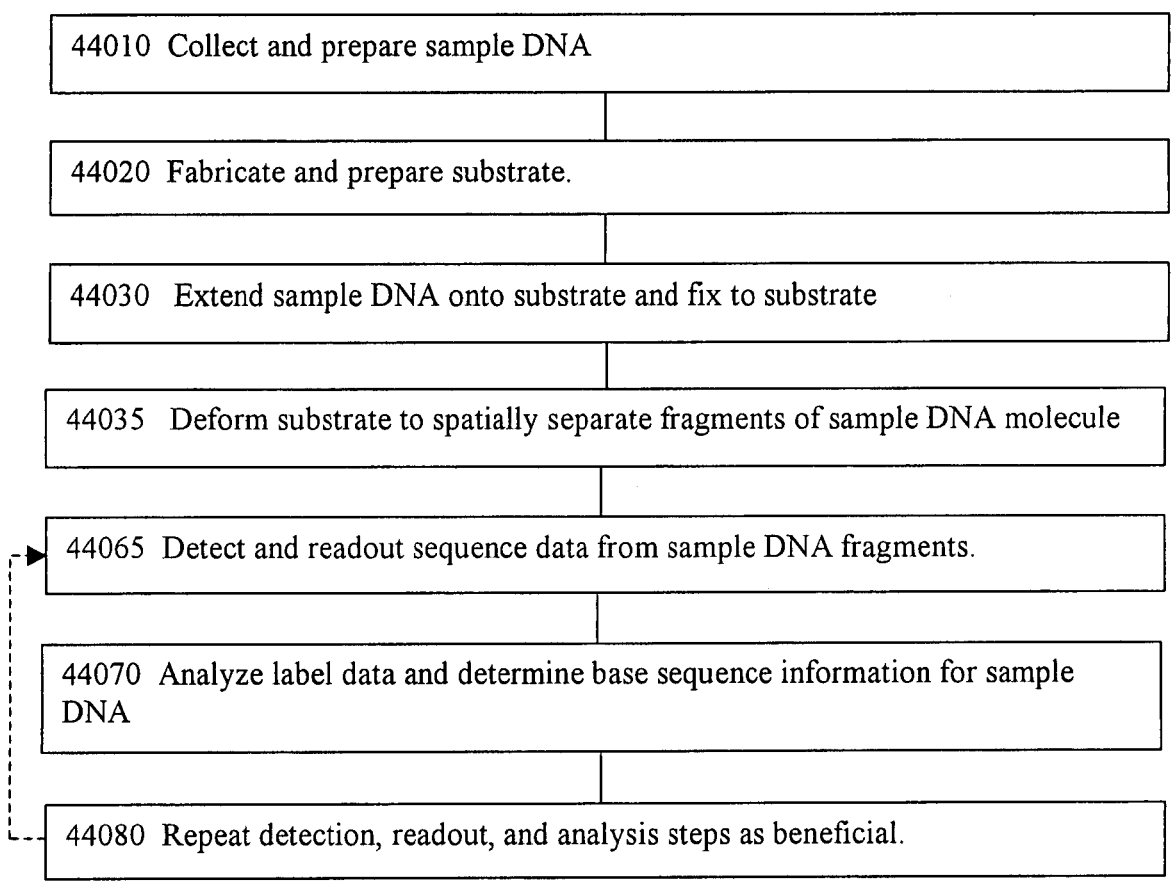

FIG. 46. Process flow diagram for further alternate method for sequencing of DNA using labeled-probe-assemblies.

Figure 47:
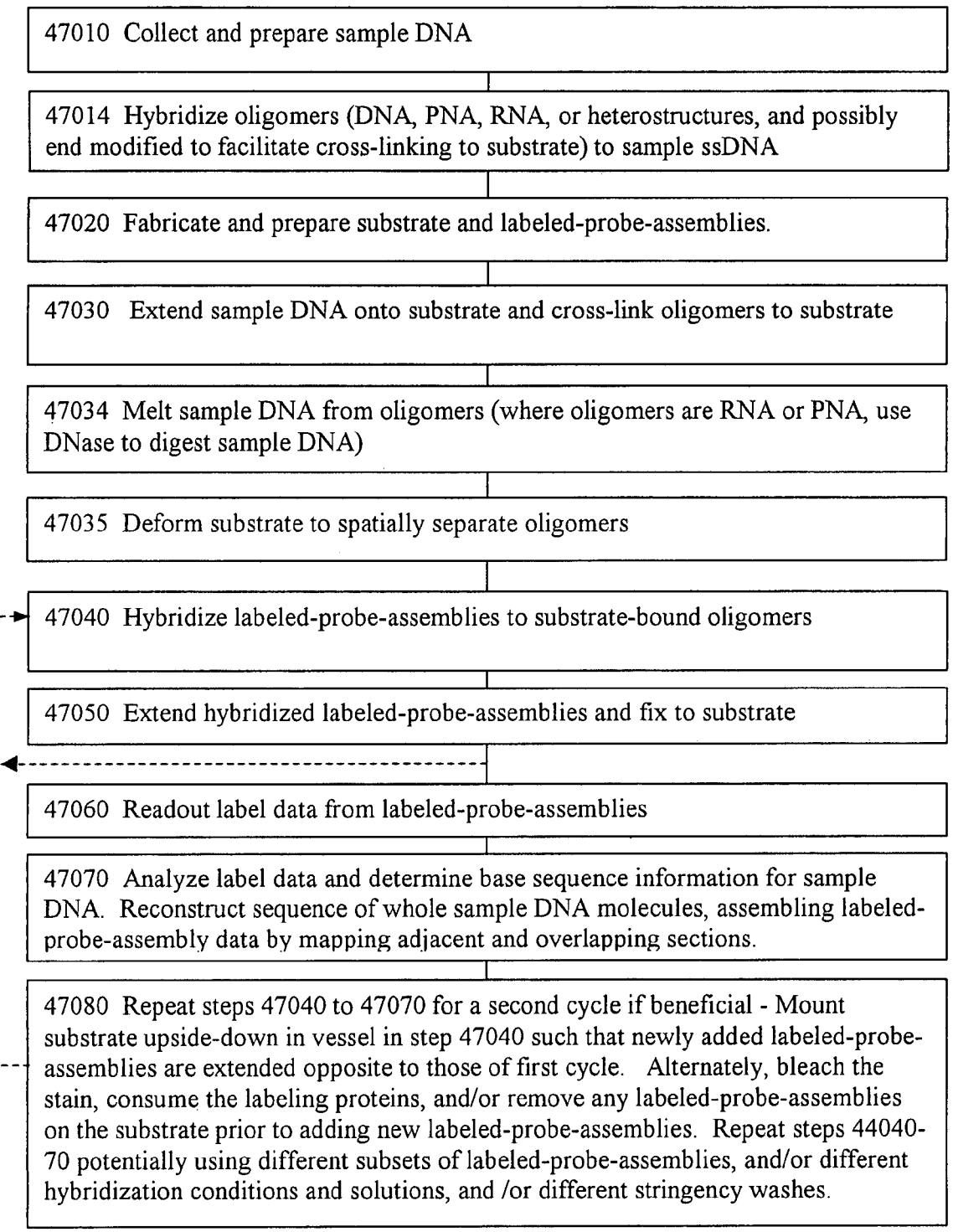

FIG. 47. Process flow diagram for further alternate method for sequencing of DNA using labeled-probe-assemblies.

Figure 48:
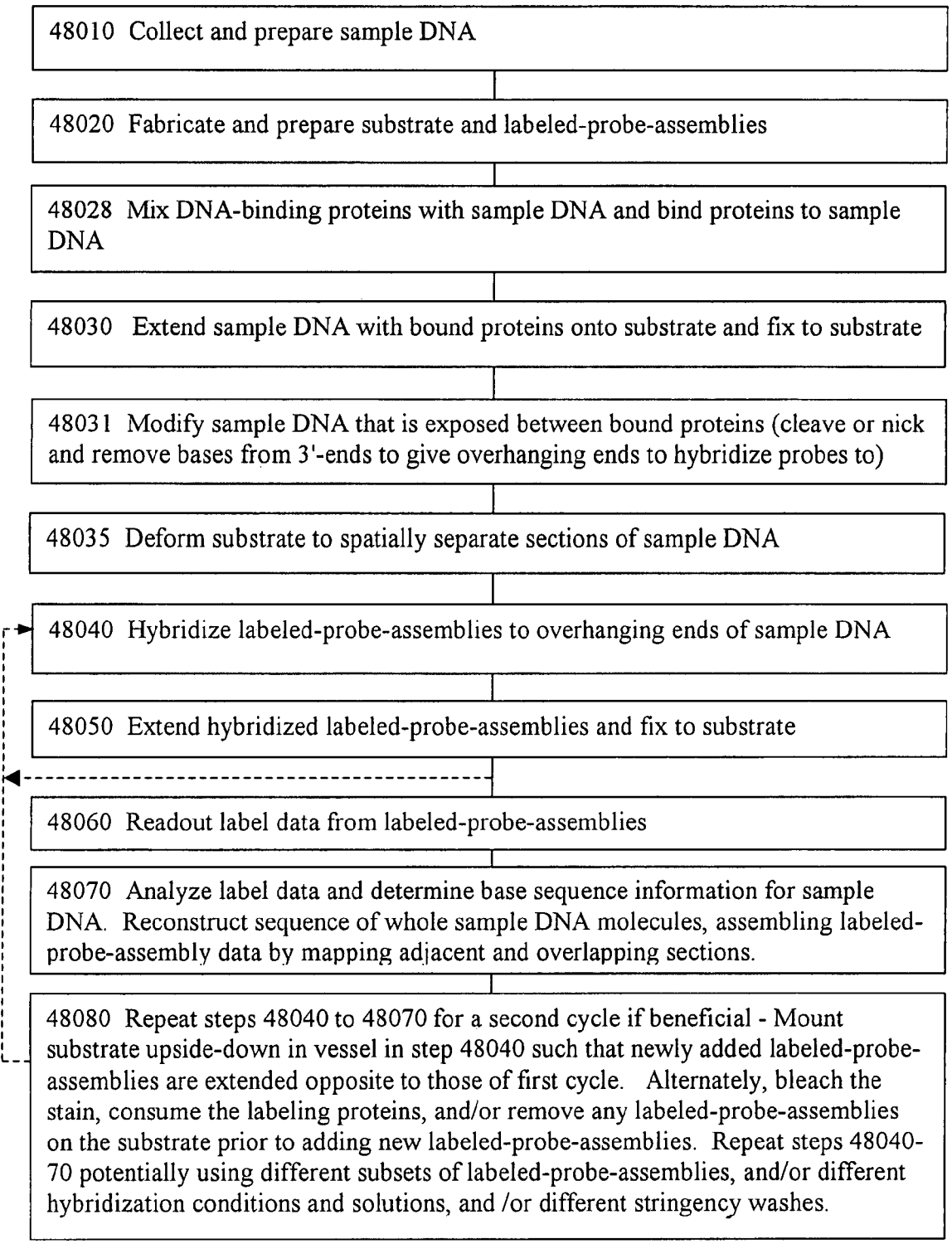

FIG. 48. Process flow diagram for further alternate method for sequencing of DNA using labeled-probe-assemblies.

Figure 49:
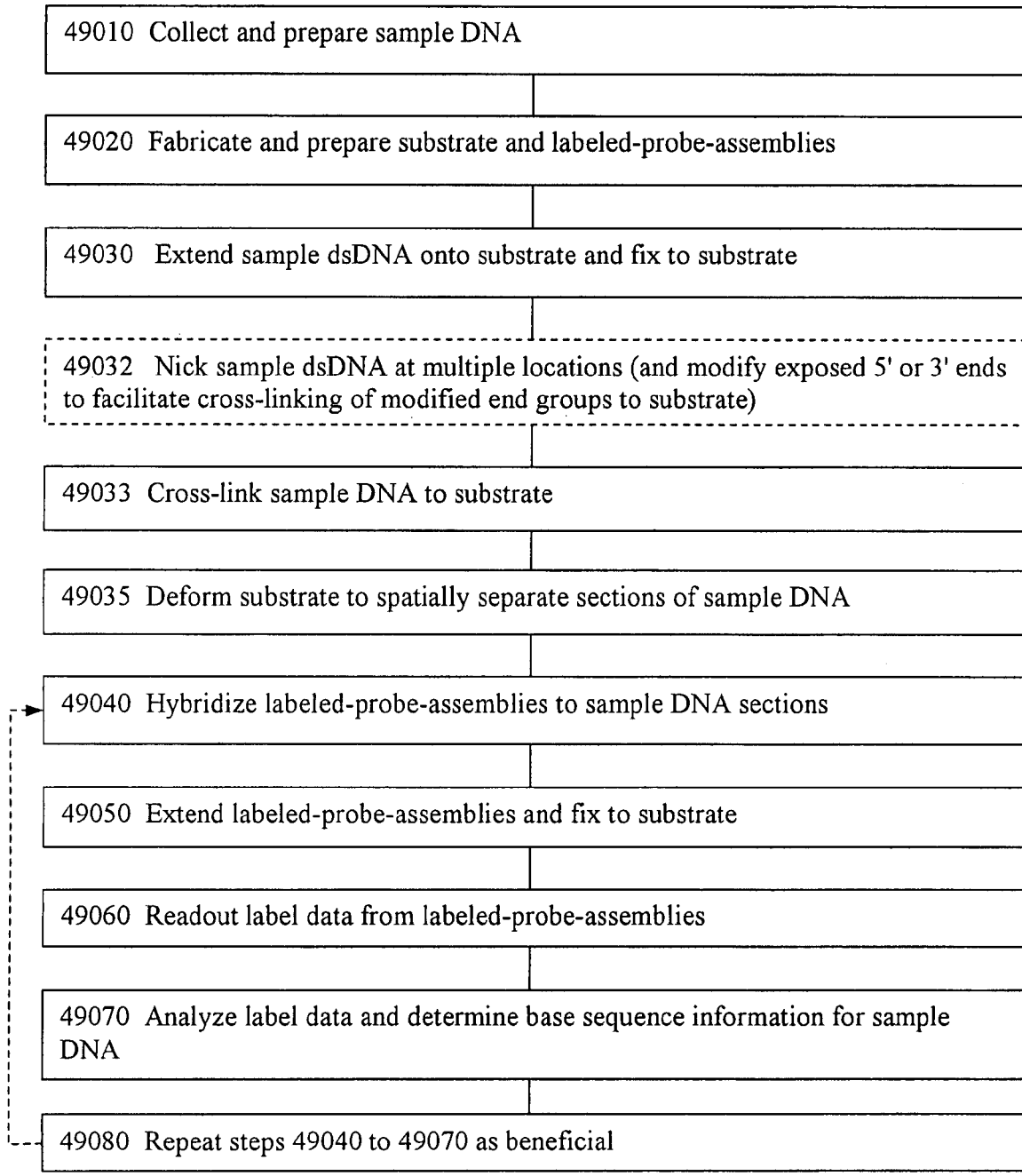

FIG. 49. Process flow diagram for further alternate method for sequencing of DNA using labeled-probe-assemblies.

Figure 50:
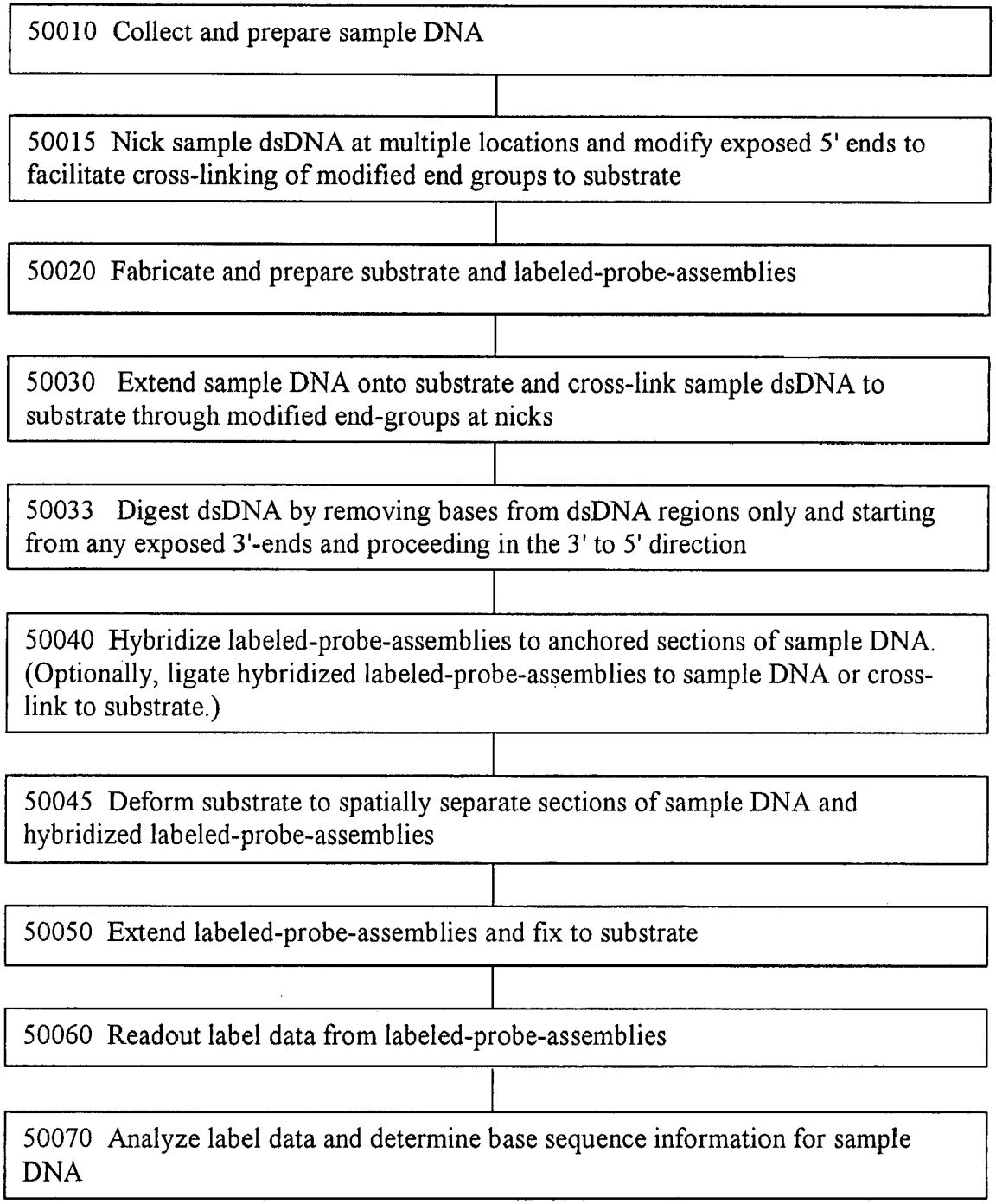

FIG. 50. Process flow diagram for further alternate method for sequencing of DNA using labeled-probe-assemblies.

FIG. 51. Process flow diagram for further alternate method for sequencing of DNA using labeled-probe-assemblies.

Figure 52:
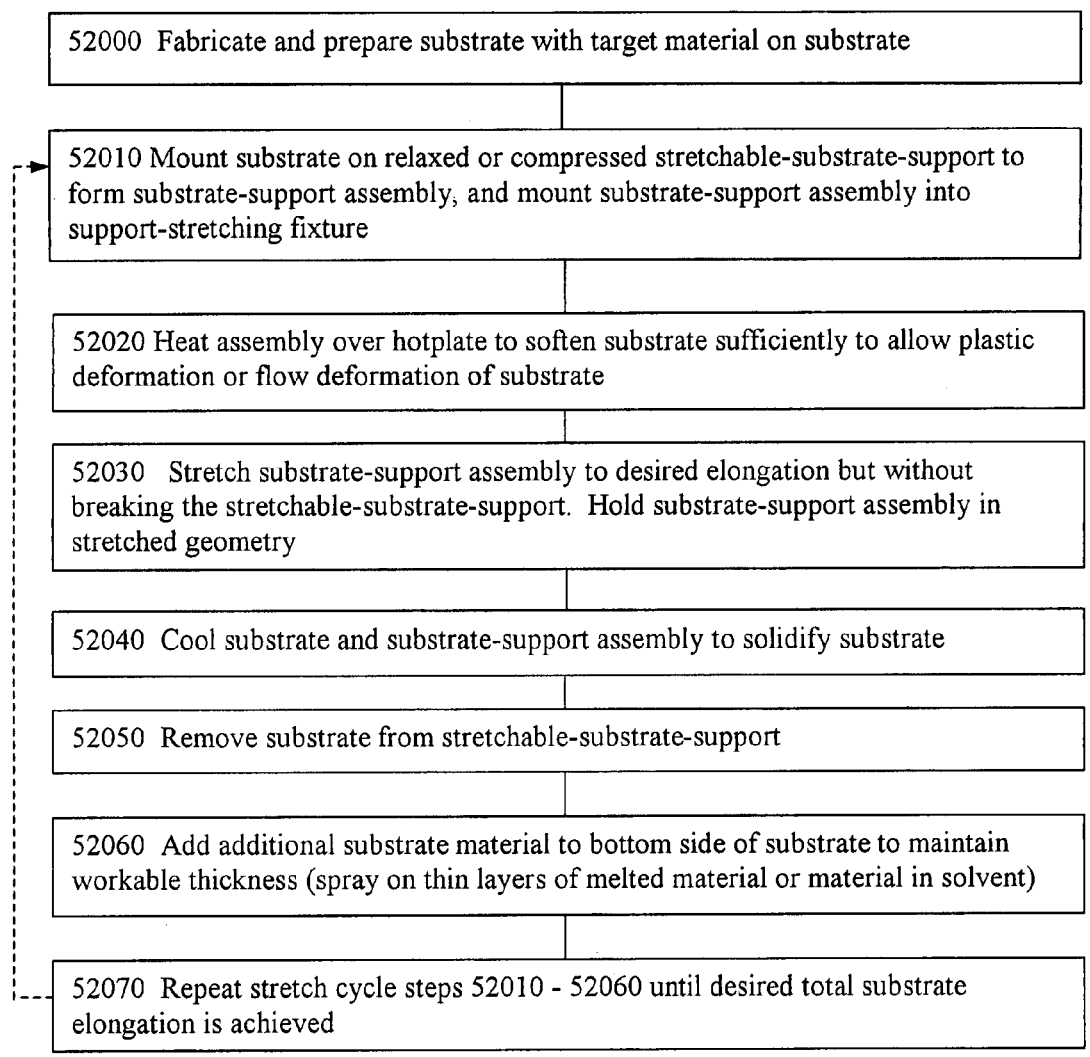

FIG. 52. Process flow diagram for method of elongating substrate.

Figure 53:
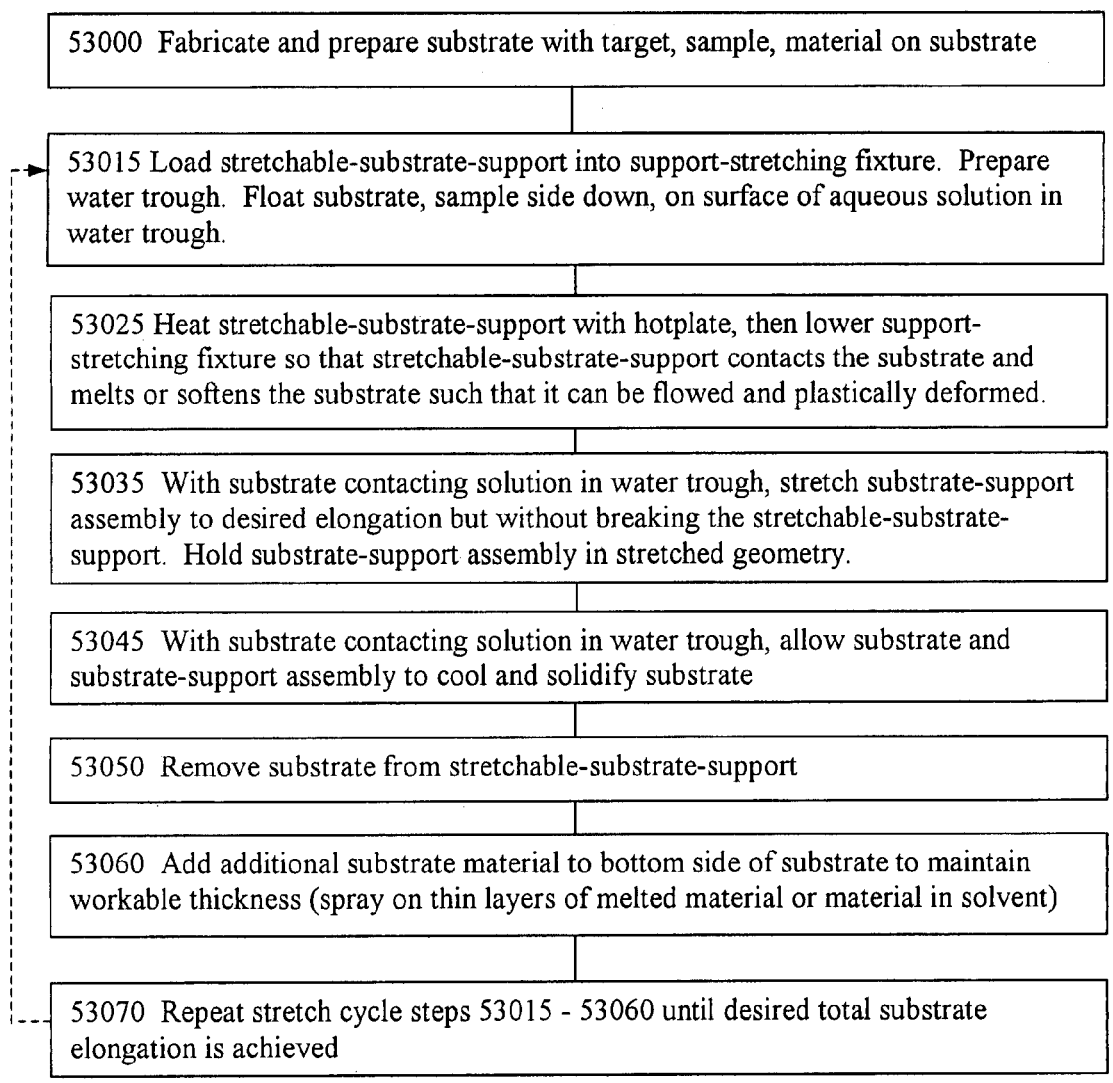

FIG. 53. Process flow diagram for alternate method of elongating substrate.

DETAILED DESCRIPTION

Labeled-Probe-Assemblies

Architecture and Information Encoding Protocols

FIG. 1 illustrates a labeled-probe-assembly with minimal detail to provide clarity to the major components. In FIG. 1, labeled-probe-assembly 100 is an assembly of two major components, a label-assembly 140 and probe 101. The functions of these two components are distinct, but their physical structures may overlap. The probe 101 includes one or more probes designed to preferentially bind to an intended target. The label-assembly 140 contains the information that can be recovered by a readout apparatus. In the embodiment illustrated in FIG. 1, the label-assembly 140 is fabricated of dsDNA, and the probe 101 is fabricated of ssDNA. For this embodiment, the intended target is any section of ssDNA with base sequence complementary to the base sequence of the probe 101. The information contained in label-assembly 140 is distributed as one or more bits of information fabricated into information-encoding regions 120 along the label-assembly, with typically one bit of information in each information-encoding region 120. In the example illustrated in FIG. 1, there are ten information-encoding regions 120. Structurally, the labeled-probe-assembly is a high molecular weight and high aspect-ratio polymer, and hence, its unconstrained shape in solution is that of a constantly moving tangle. However, when the label-assembly 140 is extended, as illustrated in FIG. 1, the separate bits of information can be spatially resolved and individually read out by the readout apparatus. Hence the information fabricated into the label-assembly 140, both the individual bits and the order of those bits, can be resolved and read by the readout apparatus, and the information recovered for data processing.

Note, one bit is defined herein as the amount of information carried in one information-encoding region, and the physical structure of each bit is dependent on the specific information encoding protocol. Most of the information encoding protocols presented in this document are designed for the encoding of DNA base sequences, and hence each bit can contain four pieces of information (modulo 4), corresponding to the four possible nucleotide bases, Adenine (A), Thymine (T), Cytosine (C), and Guanine (G). For example, the labeled-probe-assembly illustrated in FIG. 1 has ten information encoded structures 120, and hence can encode the base sequence of a ten base long section of DNA, including the identities of the bases and the order of those bases in the sequence. In electrical engineering and computer science, the bit is typically a modulo two object, physically represented by two voltage levels, whereas in this invention the bit can be an object with a modulo of two or more, being physically represented by, for example, multiple distinguishable types of stains and/or varying lengths of stained and unstained regions, etc. In this invention the bit can be an object with a modulo in the range of 2 to 100, or higher, and is typically in the range of 2 to 20, and, in the case of DNA sequence data is most often in the range of 2 to 4. This invention is not limited to a particular information encoding protocol or bit size.

In this document, numerous embodiments of suitable probes and probe structures are presented. Similarly, numerous embodiments of label-assembly structures and information encoding protocols are presented. The figures often illustrate a particular probe structure with a particular label-assembly and particular information encoding protocol. This is done to limit the number of illustration, and does not imply that the combinations illustrated are the only suitable embodiments. In fact, except where explicitly stated to the contrary, any probe or probe structure illustrated could be coupled to any label-assembly illustrated, and any information encoding protocol described could be applied to any label-assembly structure. Furthermore, in most of the label-assembly illustrations, the information encoded is a nucleotide base sequence, either 3'-A-T-C-G-5' or 3'-A-T-C-G-G-5' and usually with a separate bit to indicate the 3'-end, (or 5'-end). These simple encoded base sequences are used to simplify the illustrations only. In fact, any information, including any base sequence, can be encoded along any of the label-assemblies presented, and the number of bits, length of sequence, that can be encoded ranges from one to thousands of bits, usually the number of encoded bits will be in the range of one to one-hundred bits, and preferably in the range of 3 to 30 bits. Additionally, the illustrations provided here are not intended to limit the invention but rather to provide examples of beneficial embodiments. Based on the embodiments illustrated, many other embodiments of this invention become apparent to one skilled in the art.

In addition, for each information encoding protocol presented, alternate embodiments can be formed by permeating the four base types, A, T, C, and G, over the given base encoding representations. Furthermore, the information encoded can represent nucleotide base identity, base sequence, sequence orientation, protein identity, antigen identity, receptor identity, heparin identity, molecular identity, and any other information.

Description

Main Embodiment

Preferred Embodiment of Labeled-Probe-Assembly

Assembly Layout and Information Encoding Protocol

In the preferred embodiment of labeled-probe-assembly, illustrated in FIG. 2, the labeled-probe-assembly 200 is constructed with one ssDNA probe 210, and this is covalently attached to the label-assembly 240, which is constructed of dsDNA. Information is encoded along the label-assembly 240. Individual bits of information are encoded into separate information encoded structures 220, each of which is approximately equal in length. Within each of the regions 220, information is encoded as the particular number of *Ecoli* wild-type Lac operator O1 sequences, within the region. Each *Ecoli* wild-type Lac operator O1 sequence is designated as 230 in FIG. 2. Note, in this information encoding/readout protocol, *Ecoli* wild-type Lac repressor protein is bound to high affinity DNA sequences, 230, located at specific predetermined locations along the labeled-probe-assembly. Hence, any sequence with sufficiently high binding affinity for *Ecoli* wild-type Lac repressor protein can be used for sequences 230. The sequence 230 need not be *Ecoli* wild-type Lac operator O1, as other Lac operator sequences are acceptable, as are truncated versions of Lac operators that maintain high binding affinity. In the preferred embodiment, a 77 base-pair long version of *Ecoli* wild-type Lac operator O1 is employed. DNA with the desired sequence 230 can be obtained as detailed in Fried, et al., J. Biol. Chem. (277)52: 50676 50682 (2002). Alternate embodiments use other sequences 230, including the sequence 3'-A-C-A-C-A-C-C-T-T-A-A-C-A-C-T-C-G-C-C-T-A-T-T-G-T-T-A-A-A-G-T-G-T-G-T-5' (SEQ ID NO:2) along with the complementary strand (SEQ ID NO:1) to form the double-stranded sequence 230. For simplicity, any acceptable sequence 230 is referred to here as Lac operator.

Within each region 220, adjacent Lac operator O1 sequences 230 are separated by short spacer lengths of dsDNA 225, of approximately equal length in the range of roughly 5-50 nm, which is equivalent to approximately 15 to 150 bases. The variation in spacer lengths 225 over the entire labeled-probe-assembly is typically held to less than +/−20%, and preferably less than +/−10% around the mean. As illustrated in FIG. 2, all Lac operator O1 sequences 230 within each region 220 are grouped around the center of the region, and roughly equal lengths of spacer DNA bound this central grouping, filling the rest of the region. The length of the regions 220 are made approximately equal, typically with variations of less than +/−20%, and preferably less than +/−10% around the mean, and of mean length equal to or greater than the length of six sequences 230 plus seven short spacer lengths 225. Minimizing the overall length of the labeled-probe-assemblies, on a per bit of encoded information basis, is desirable.

Only those sequence lengths designated as Lac operator O1 sequences 230 form Lac operator sequences. There are no Lac operator sequences within the lengths of spacer DNA, and this is true for all Lac operator sequences, including O1, R1, L1, etc. Additionally, there are no high affinity binding, recognition, sites for *Ecoli* wild-type Lac repressor protein along the label-assembly 240, except the Lac operator sequences 230, which are high affinity binding sites. In this assembly, *Ecoli* wild-type Lac repressor protein will bind with high affinity to any Lac operator O1 sequences 230 and with very much lower affinity elsewhere along the label-assembly 240.

In the preferred embodiment, the information encoded along the label-assembly 240 is the complement of the base sequence of the attached ssDNA probe 210, and the particular information encoding protocol employed is as follows. The sequence start indicator 250 is the region 220 closest to the probe 210 and contains six Lac operator O1 sequences 230. In this protocol, the start indicator 250 identifies the 3'-end of the encoded base sequence. Following the start indicator 250, each subsequent region 220 holds the identity of one DNA base, with the order of the encoded bases identical to the order of bases along the base-complement of the probe 210. Base identity is encoded as follows; each Adenine (A) is encoded as one Lac operator O1 sequence 230 within its region 220, each T is encoded as two Lac operator O1 sequences 230 within its region 220, each C is encoded as three Lac operator O1 sequences 230 within its region 220, and each G is encoded as four Lac operator O1 sequences 230 within its region 220. Hence in the example labeled-probe-assembly illustrated in FIG. 2, the base sequence of the ssDNA probe 210 is 5'-T-A-G-C-3', and the information encoded along the label-assembly 240 is 3'-A-T-C-G-5'. Labeled-probe-assemblies fabricated with other probe sequences and probe lengths are constructed with the appropriate number of information encoded structures 220 and appropriate number of Lac operator O1 sequences 230 in each region 220, according to the information encoding protocol presented in this paragraph. The length of probe 210 can be in the range of two to hundreds of bases long, and is usually in the range of 4 to 50 bases long and is preferably of 8 to 25 bases in length.

In an alternate embodiment, the information encoded along the labeled-probe-assemblies only represents a portion of the base sequence of the probe, and in this case, the probe length can be in the range of two bases to tens of thousands of bases. For example, the probe may be 100 bases long, whereas the information encoded along the attached label-assembly might include only a run of 10 bases from within the 100 bases. Alternately, every other base along the probe may be encoded into the labeled-assembly, or every third base, or any other predetermined pattern of bases along the probe may be encoded into the labeled-probe-assembly.

During the use of the labeled-probe-assemblies, Lac proteins are bound to the high affinity binding sites, regions 230 in FIG. 2. Binding of Lac proteins to the labeled-probe-assembly illustrated in FIG. 2 will result in the configuration illustrated in FIG. 3. FIG. 3 illustrates assembly 300, the labeled-probe-assembly illustrated in FIG. 2 decorated with bound Lac proteins, extended in a straight line to its full length. The Lac proteins 360, illustrated as black dots, bind to each of the regions 230 of FIG. 2. In FIG. 3, to avoid unnecessary leading-lines, only one of the Lac proteins is labeled with 360 and the rest are shown as large black dots. As is apparent from the illustration, the end region with six adjacent Lac proteins is the start indicator 350. To one side of start indicator 350 is the probe 210. To the other side of start indicator 350 are four information encoded structures, the first with one bound Lac protein indicating an encoded (A) 322, the second with two Lac proteins indicating a (T) 324, the third with three Lac proteins indicating a (C) 326, and the last with four Lac proteins indicating a (G) 328.

Preferred Embodiment

Method of Manufacture

Preferred embodiment labeled-probe-assemblies are constructed of DNA, and hence can be fabricated using any of the many existing methods for manipulating the structure of DNA. In general, sections of the labeled-probe-assemblies, such as the probes, and others, can be synthesized using standard automated solid-phase methods. In addition, some or all of the sections, such as the Lac operator sequences 230 of FIG. 2, can be collected from commercially available plasmids and other biological sources by standard molecular biology techniques, such as cleavage with restriction enzymes and gel purification. Once the various different sections are available, they can be assembled by ligation into master labeled-probe-assemblies, and once assembled, they can be amplified, mass produced, by standard PCR (polymerase chain reaction) and/or cloning techniques.

To facilitate PCR and/or cloning, additional lengths of DNA are typically appended to the master labeled-probe-assemblies. If PCR of a linear DNA molecule is the chosen amplification technique, then additional DNA is added to the probe end and label-assembly end. These added lengths will include primer binding sequences, needed for standard PCR, and recognition sequences for double-strand cutting restriction enzymes, used to remove these added lengths after amplification. In the preferred embodiment, the labeled-probe-assemblies are amplified by cloning, which also requires the addition of added lengths of DNA. To facilitate cloning, typically, master labeled-probe-assemblies are fabricated as dsDNA, including the probe region, and are ligated into a cloning vector. Any typical cloning vector, plasmid, cosmid, BAC (bacterial artificial chromosome), YAC (Yeast Artificial Chromosome), etc., with sufficient payload capacity can be used.

Note that once the master labeled-probe-assemblies are assembled, labeled-probe-assemblies with different sequences can be mixed together, amplified together in the same vessel (PCR and/or cloning), extracted together, purified together, and stored and used together. Hence, once the master copies of all the different labeled-probe-assemblies are fabricated, each in its own vessel, many can be mixed together and processed simultaneously in one, or a few, vessels. Labeled-probe-assemblies that can use the same restriction enzymes during extraction and uncovering of the probes can be processed in the same vessel. Hence, only a few vessels are required to amplify and process all the types of labeled-probe-assemblies that include a complete set of possible probe sequences of a given length. To limit probe-to-probe hybridization during use of the labeled-probe-assemblies, the complete set of labeled-probe-assemblies can be processed as two or more subsets, where members within each subset have non-complementary probe sequences. The potential to simultaneously process, amplify, extract, and store entire sets and subsets of labeled-probe-assemblies in a small number of vessels provides considerable benefit to low cost production.

Extraction of the labeled-probe-assemblies from the PCR products or cloning vectors, plasmids, cosmids, BAC's, YAC's, etc., can be accomplished using any suitable method, including the following enzymatic process to uncover the ssDNA probes. In this process, two types of restriction enzymes are employed, one to generated double-strand breaks and another that generates only single strand breaks. This second type of restriction enzyme is usually referred to as a nicking enzyme. FIG. 4a illustrated the dsDNA base sequence of an example labeled-probe-assembly around the probe region for the case where the two types of restriction enzymes used are the blunt-end forming, double-strand cutting Mly I and the nicking enzyme Nb.Bsm I. Both enzymes are commercially available from New England Biolabs, as are the process reagents and recommended process steps for carrying out the enzymatic cutting and for stopping the reaction. FIG. 4a shows the recognition sequence for Mly I 400, the double-strand cutting points for Mly I 410, the recognition sequence for Nb.Bsm I 420, and the single-strand cut point for Nb.Bsm I 430. To the right of 400, in the illustration 4a, is non-labeled-probe-assembly DNA (e.g. PCR primer sequence or cloning vector), and to the left of 420 is the label-assembly. What will become the probe is located between 410 and 430 and is labeled as 440. In the example illustrated the probe is 8 bases long, can be any sequence of eight bases, and the bases are shown by eight "N". The bases listed as "N" can be arbitrarily selected, and the bases "n" are the corresponding base complements.

The extraction process consists of treating the PCR products or cloning vectors with both Nb.Bsm I and Mly I, then heating to remove the single-strand section of DNA between 430 and 410. This low molecular weight ssDNA can be removed by gel purification. At this point, the probe region will have the structure illustrated in FIG. 4b, where the probe 440 and excess overhang 450 are both ssDNA. Next, ssDNA oligomers of sequence 5'-N-N-N-N-N-N-N-N-N-N-N-N-G-3' 460 (residues 19 through 31 of SEQ ID NO:4), the base complement to 450 (residues 6 through 18 of SEQ ID NO:3), are added and ligated to the labeled-probe-assemblies, resulting in the competed labeled-probe-assembly structure shown in FIG. 4c, in which only the probe 440 is ssDNA. Note, oligomers 460 can be readily produced by solid-phase synthesis, although any method is acceptable, and can be optionally dephosphorylated prior to addition, in order to prevent ligation of back-to-back copies. Furthermore, oligomers of the same sequence can be used with any probe sequence and with any labeled-probe-assembly that has the mating complementary sequence at 450. The length of the oligomers 460 is at least one base (a Guanine), and is due to the nick location of Nb.Bsm I being on its recognition sequence. However, to facilitate annealing and ligation, 460 is made longer, typically in the range of 8 to 30 bases, and in the example shown, it is 13 bases in length. The bases "n" of oligomer 460 can be arbitrarily chosen, and it is beneficial if the G+C to A+T ratio of this section is in the range of 0.6 to 0.8. Note that other nicking and double-strand-cutting restriction enzymes are commercially available and can be substituted for Nb.Bsm I and Mly I, with the appropriate changes in recognition sequences 400 and 420 and oligomer sequence 460.

Use of at least two different nicking enzymes and two different double-strand cutting restriction enzymes, with different recognition sequences, is typically required to produce complete sets of labeled-probe-assemblies, with all possible probe sequences of a given length. This is typically required to allow for probe sequences that include the recognition sequence of one of the enzymes.

Depending on the choice of nicking enzyme, the probe will be either a 5' or 3' overhang. For example, when the nicking enzyme Nt.Alw I, also available from New England Biolabs, is used in combination with Mly I, the sequence around the probe 540 can be as shown in FIG. 5a. FIG. 5a shows the recognition sequence for Mly I 400, the double-strand cutting points for Mly I 410, the recognition sequence for Nt.Alw I 520, and the single-strand cut point for Nt.Alw I 530. This nicking enzyme leads to a 5'-overhanging probe, illustrated in FIG. 5b as an 8-mer (8 nucleotide base length) probe 540. To the left of region 520 in FIG. 5b is the rest of the labeled-probe-assembly. One advantage of Nt.Alw I is that it nicks outside of its recognition sequence, and hence the probe sequence can be almost arbitrary without the need for ligation of a capping oligomer such as 460 in FIG. 4c.

Further note that the double-strand cutting enzyme Mly I can be replaced by other double-strand cutting enzymes or nicking enzyme. The same nicking enzyme used to generate the probe overhang can be used to make the cut that terminates the probe, and hence only one enzyme type need by used. In this case, one copy of the recognition sequence for this nicking enzyme would be located to the left of the probe and one copy to the right of the probe, and facing in opposite directions. In this way, the two recognition sequences lead to the cutting of both strands, but with the cuts staggered by an amount that includes the probe. After extraction from the PCR products or cloning vectors, the labeled-probe-assemblies can be purified and the non-labeled-probe-assembly DNA separated out by any of the standard methods, including gel purification by length stratification and methods that employ a functionalized surface, functionalized beads, functionalized column separation, functionalized spin column, etc. to trap and hold either the non-labeled-probe-assembly DNA or the product labeled-probe-assemblies. Proteins can be removed by standard methods, including treatment with protein kinase K, if desired. After purification, the labeledprobe-assemblies can be stored for long periods by using existing standard techniques for storing DNA.

Operation of Preferred Embodiment

Method of Use in Sequencing

The preferred use for labeled-probe-assemblies is for the determination of the base sequence of linear sample DNA molecules. The preferred method of use is outlined in FIG. 43, and described in detail in the following paragraphs. The preferred method applies to the sequencing of linear dsDNA using the preferred type of labeled-probe-assemblies.

The process flow is outlined in FIG. 43 and starts in box 43010 with the collection and preparation of sample DNA. DNA from any source, organism, animal, plant, bacterium, fungi, viron, cell, cell-line, biopsy, synthetic source, cDNA, cDNA library, RNA, RNA-DNA heteroduplex, etc., can be used, and recovery of the sample dsDNA from the source can proceed by any available method. Many suitable methods of extraction and recovery of dsDNA are available in the literature, and kits are commercially available. Samples may be treated with protein kinase K, to remove proteins, RNase, to remove RNA, and cDNA can be formed where RNA is to be sequenced, or RNA can be sequenced directly. In cases where the recovered DNA is circular, it can be made linear by double-strand cleavage.

A major benefit of this sequencing technique is that it can be used to sequence long DNA molecules, and in fact, longer sample dsDNA molecules are preferable. Hence extraction and recovery methods that minimize strand cleavage and maximize sample length are preferred. Once recovered, sample DNA can be stored in a storage buffer at low temperature.

Prior to use of the sample DNA, one or both ends, preferable only one end, are biotinylated. The standard 3'-end labeling procedure using Terminal Transferase and biotin linked UTP is one acceptable choice. Biotin end labeling kits and protocols are available in the literature and from several commercial sources including Enzo Life Sciences Incorporated, Farmingdale, N.Y., BioProbe 3'-Oligonucleotide Labeling System and other products, and Vector Laboratories Incorporated, Burlingame, Calif., 3' EndTag DNA Labeling System along with Biotin maleimide.

In FIG. 43, box 43020 covers the fabrication of labeled-probe-assemblies and fabrication and preparation of a substrate. Fabrication of the preferred labeled-probe-assemblies has been detailed elsewhere in this document and is not repeated here. Note that the one or more unique sets of labeled-probe-assemblies can be used, each unique set consisting of labeled-probe-assemblies with different sets of probes (different probe sequences and/or lengths). The preferred substrate for use with the preferred labeled-probe-assemblies is illustrated in FIG. 6a, the substrate 600 is an assembly consisting of a thin layer of sputter deposited carbon 620 on the freshly cleaved surface of a piece of Mica 610. The structure and process for making the structure are taken from standard Electron Microscopy (EM) sample preparation practice, and many suitable processes are available in the literature.

Once the substrate is formed, a narrow strip of avidin or streptavidin, the narrow sample-end-anchoring strip, is printed and dried onto the substrate, resulting in the structure illustrated in FIG. 6b. Referring to FIG. 6b, the substrate assembly 602 consists of the narrow sample-end-anchoring strip 630 and the thin layer of sputter deposited carbon 620 on the freshly cleaved surface of the piece of Mica 610. This narrow strip of avidin or streptavidin is printed using the straight edge of a silicone rubber (PDMS) sheet as a rubber-stamp. To form the stamp, a sheet of ~¼" thick silicone rubber is cut in a straight line with a sharp razor blade at a 90 degree angle to the surface of the sheet. The end of the silicone rubber stamp is dipped into an aqueous solution containing either avidin or streptavidin. The solution being standard storage solution for the avidin or streptavidin. The solution is allowed to dry on the silicone rubber. Then the silicone sheet is held at a 45 degree angle relative to the surface of the substrate, and one edge of the avidin treated end is pressed gently against the surface of the substrate. The stamp is held in place against the substrate for approximately 30 minutes in order to transfer some of the avidin, or streptavidin, to the surface of the substrate, after which the stamp is removed. Alternately, an aqueous mixture containing avidin and/or streptavidin can be applied with a fine brush as a stripe of material across the substrate and dried.

In FIG. 43, box 43030 covers extension of the sample dsDNA onto the surface of the substrate and fixing the extended sample DNA to the surface. Many methods for extending DNA over the surface of a substrate are available in the literature. In the preferred embodiment, an apparatus such as that illustrated in FIGS. 7a and 7b is used. FIG. 7a illustrates a side-view cut and FIG. 7b a front view cut of the sample extension vessel. Referring to FIGS. 7a and 7b, the substrate 602 is fixed into the vessel using clips 710 such that the narrow sample-end-anchoring strip 630 (line of avidin molecules) on the substrate is oriented approximately parallel to the base of the vessel 700 and is toward the top of the substrate. The vessel 700 is made of polystyrene, Teflon, silanized glass, or other such material that minimizes absorption of biotin and DNA. Fluid can enter and exit the vessel from the bottom through tube 720. Draining the vessel is accomplished by opening metering valve 730, and the vessel can be filled by either adding fluid directly into the top of the vessel, using a pipette or syringe, for example, or by opening metering valve 740 to allow fluid in reservoir 750 to flow into the vessel. The height and width of the inside of the vessel 700 is made sufficient to contain the substrate. The width of the tank in the direction perpendicular to the substrate surface is typically in the range of 1/10 to ¼ the height of substrate, and can be made thinner to reduce volume when sample DNA is limited.

Biotinylated sample DNA in an aqueous solution, such as 10 mM Tris-HCl, pH 8.0, 1 mM EDTA, or 10:1 water:AF-solution (1% p-phenylenediamine, 15 mM NaCl, 1 mM $H_2PO_4$, pH 8.0, 90% glycerol), is added slowly to the vessel. To limit non-specific binding of sample DNA to the substrate, solution pH should be 7.0 or greater, and solution pH should be adjusted prior to introduction into the vessel. When handling, transferring, the DNA solution, care should be taken to minimize fluid turbulence and shear so as to limit cleavage of the sample DNA. A pipette can be used to transfer the sample from its storage container into the vessel. The mixture is allowed to stand in the vessel for approximately 10 minutes or longer, to allow the biotinylated DNA to bind to the avidin, or streptavidin, on the substrate, and then the vessel is placed in a refrigerator and cooled to 4 C. To extend the sample DNA molecules, fluid is slowly drained from the bottom of the vessel by opening valve 730 as shown in FIG. 7a. Valve 730 is adjusted so that the meniscus within the vessel lowers at a rate of approximately 1 mm per hour, although this rate is not critical. Sample DNA molecules, that are bound at one end to the substrate, are extended over the substrate surface as the level of the solution recedes. The sample DNA molecules are extended in a direction approximately perpendicular to the surface of the solution. Once the vessel has been drained, the substrate is dried thoroughly in order to fix the sample DNA to the substrate. FIGS. 8*a*-8*c* illustrate the progression from biotinylated sample-DNA bound to the avidin on the substrate, as illustrated in FIG. 8*a*, to partially extended sample DNA as illustrated in FIG. 8*b*, and finally, to fully extended sample DNA as illustrated in FIG. 8*c*. In the FIGS. 8*a-c*, the vessel 700 is shown as a front view cut with clips 710 holding substrate 602, the line of avidin-biotin-sample-DNA conjugates are shown as the line of dots 810 (the avidin molecules form the sample-end-anchoring strip 630 of FIGS. 6*b* and 8*a*), and the solution meniscus is shown as the line 820. In FIGS. 8*a*-8*c*, the extended sample DNA molecules 830 are illustrated, but the sample DNA in solution is not, nor are those portions of the extended DNA molecules that are in solution. Furthermore, for clarity of the illustration, only two of the possibly many extended sample DNA molecules 830 are labeled (the others are illustrated as straight lines extending from the line of avidin-biotin-sample-DNA conjugates 810 toward the solution meniscus 820 and perpendicular to 820), and only two of the possibly many avidin-biotin-sample-DNA conjugates 810 is labeled (the others are illustrated as black dots falling along a straight line parallel to the solution meniscus 820). Note that the extended sample DNA molecules 830 are extended approximately along a single direction, perpendicular to the solution meniscus 820, and that molecules 830 can be, and often are, of different lengths. In FIG. 8*c*, the substrate 602 is shown to be long enough such that the extended sample DNA molecules 830 end before reaching the bottom edge of the substrate 602. This can be beneficial but is not required.

In FIG. 43, box 43032 covers the formation of single-strand regions of sample DNA, which are then available as hybridization targets for the ssDNA probes of the labeled-probe-assemblies. Box 43032 is specific to sequencing of dsDNA samples, and is not included in the process flow when the sample DNA is single-stranded. Many methods of forming single-strand regions along the fixed dsDNA are widely known. The preferred method for this substrate type is to thermally melt the dsDNA in hot solution and then fix the DNA by drying the substrate. The substrate is placed in 70% formamide/2×SSC (where 20×SSC is a mixture of 3M NaCl, 0.3M trisodium citrate 2H2O, pH adjusted to 7.0 with 1M HCl) at 70 C for 2 minutes to denature the strands, followed by immersion in cold 70% ethanol for 1 minute, then 90% ethanol for one minute, then 100% ethanol for one minute, and then air dried.

In FIG. 43, box 43040 covers hybridization of the labeled-probe-assemblies to the substrate bound sample DNA. The hybridization process is conducted in the same vessel that will be used to extend the hybridized labeled-probe-assemblies. This vessel is the same or similar to the vessel 700 of FIG. 7 used in box 43030 of FIG. 43 to extend the sample DNA molecules. The substrate, with extended and fixed sample DNA molecules 930, is placed in the vessel such that the axis of the extended sample DNA molecules is approximately perpendicular to the direction of gravity, parallel to the surface of the hybridization solution 920, as illustrated in FIG. 9. Note, FIG. 9 illustrates the substrate in the vessel after hybridization of labeled-probe-assemblies and part way through the labeled-probe-assembly extension process. Hence, the orientation of the substrate within the vessel is rotated 90 degrees to that of the substrate during step 43030 of FIG. 43.

Prior to use in step 43040 of FIG. 43, the labeled-probe-assemblies are added to the hybridization solution and heated so as to denature any probe-to-probe hybrids that may have annealed during storage, however, the temperature and duration should not be so great as to denature entire labeled-probe-assemblies. The temperature should just exceed the calculated melting temperature for the most stable probe-to-probe hybrid, for example, for a probe length of 10 bases in SSC-based hybridization solution, the labeled-probe-assemblies should be heated to 45 C for one minute, then rapidly cooled to the desired hybridization temperature. The temperature used depends on the chemistry of the hybridization solution used. Many acceptable hybridization solution formulations are available in the literature. See for example Chapter 9 "Hybridization Analysis" in Molecular Biology Labfax (1990). The choice of an optimum solution depends on several variables, including the length of the probes, whether the probes and sample molecules are DNA, RNA, or PNA, and variation in G-C to A-T ratio of the various probes. For instance, three typical hybridization solution, any of which can be used, include SSC hybridization solution (sodium chloride/sodium citrate based solution of 0.45M NaCl, 0.045M trisodium citrate 2H2O, pH adjusted to 7.0 with 0.15M HCl, 0.05% sodium pyrophosphate), diluted AF-solution (10:1 SSC hybridization solution: AF-solution (1% p-phenylenediamine, 15 mM NaCl, 1 mM H2PO4, pH 8.0, 90% glycerol), and TMAC (Tetramethylammonium chloride) based hybridization solution. For example, see recipe in Short Protocols in Molecular Biology, 4th ed., F. M. Ausubel, et. al., John Wiley & Sons, Inc., 1999, page A1-40. Commercially available solutions are also acceptable, as are additives to speed hybridization and increase stringency, such as dextran sulfate (Mol. Wt 500,000) and increased sodium-salts. Typically, solution pH is kept above 7.0 to limit binding of free DNA molecules, sample or labeled-probe-assemblies, to the substrate. TMAC based solution is used primarily in cases where the difference in binding energy between G-C rich and poor probes causes issues with stringency. The SSC hybridization solution is the preferred solution.

The hybridization solution with labeled-probe-assemblies is then added to the vessel to cover at least that portion of the substrate with extended sample DNA molecules. Hybridization is allowed to continue until the desired percentage of hybridization interaction has completed or the process has saturated. Typically, the hybridization reaction is given 18 to 48 hours, and longer or shorter times are acceptable. Following hybridization, stringency rinses may be employed to remove any incorrectly hybridized probe. Many examples of stringency rinses and procedures are available in the literature, however, it is important to limit physical agitation and fluid flows to minimize the probability of shearing the labeled-probe-assemblies. If used, stringency rinse solutions are slowly added at the top of the vessel by syringe while simultaneously draining fluid at approximately the same rate from the bottom drain, 730 illustrated in FIG. 7*a*.

Following hybridization and any stringency rinses, a solution containing Lac operator proteins (*Ecoli* wild-type Lac operator) is slowly added to the vessel. Lac proteins are allowed to bind to the Lac operators on the labeled-probe-assemblies. One acceptable Lac protein solution consists of 10 mM Tris-HCL (pH 8.0), 1 mM EDTA, 250 mM KCL, and Lac operator proteins. The concentration of Lac operator protein in the solution can be adjusted to maximize repressor sequence specific binding while minimizing non-specific sequence binding. A starting concentration of Lac operator protein from which to start optimization is 0.01 uM (micromolar). Solution temperature is maintained at approximately 21 C, or at a lower temperature if required to prevent hybridized probes from denaturing from the sample DNA. Optionally, ethylene glycol can be added up to approximately 7% v/v level in order to increase the operator specific to non-specific sequence binding ratio, and 0.1 mg/ml BSA (bovine serum albumin) can be added to reduce non-specific substrate binding of Lac protein. The binding reaction is allowed to equilibrate, typically for approximately one hour, and longer at temperatures below 21 C.

FIG. 43, box 43050 covers the step of extending all labeled-probe-assemblies that are hybridized along the sample DNA molecules, in a direction that is approximately perpendicular to the direction in which the sample DNA molecules are extended. The hybridized labeled-probe-assemblies are extended over the substrate using a process similar to that detailed in step 43030 and illustrated in FIG. 9. Valve 730 of illustration 7a is adjusted to allow the solution within the vessel to drain such that the meniscus within the vessel lowers at a rate of approximately 1 mm per hour, although this rate is not critical. Labeled-probe-assemblies that are bound at one end to sample DNA molecules, are extended over the substrate surface as the level of the solution recedes. The labeled-probe-assemblies are extended in a direction approximately perpendicular to the surface of the solution. FIG. 9 illustrates the front-view cut of the configuration part-way through the process of extending the labeled-probe-assemblies. Referring to FIG. 9, substrate 602 is held by clips 710 into vessel 700, as the surface of the hybridization solution 920 is lowered, those labeled-probe-assemblies 940 that are hybridized to the extended and fixed sample DNA molecules 930 are extended over the surface of substrate 602. Only the extended labeled-probe-assemblies 940 are illustrated. The direction of extension of the labeled-probe-assemblies 940 is approximately perpendicular to the surface of the hybridization solution 920. The avidin-biotin-sample-DNA conjugates 810 are also illustrated in FIG. 9. FIG. 9 also illustrates a close-up view looking down onto the substrate 602 and showing the extended and fixed sample DNA molecules 930 and the extended labeled-probe-assemblies 940. Where the probes of the labeled-probe-assemblies are hybridized to the extended and fixed sample DNA molecules 930 is illustrate in the close-up view in FIG. 9 as probe-sample duplex regions 950. Note, for clarity in FIG. 9, only a few of the possibly many 810, 930, 940, and 950 are labeled, and the Lac proteins are not shown. Once the vessel has been drained, the substrate is dried thoroughly in order to fix the labeled-probe-assemblies to the substrate.

The resulting configuration of sample DNA molecule and hybridized labeled-probe-assemblies is illustrated in FIG. 10, which illustrates a top-view of a portion of the substrate 602 with a portion of one extended and fixed sample DNA molecule 930. Labeled-probe-assemblies 940 include probes 210 that are hybridized to sample molecule 930 to form probe-sample duplex regions 950. Labeled-probe-assemblies 940 are extended approximately perpendicular to the sample DNA molecule 930. Lac proteins 360 are bound to the labeled-probe-assemblies in predetermined patterns to form the encoded information regions; start indicator (3'-end) 350, (A) 322, (T) 324, (C) 326, and (G) 328. Hence the right most labeled-probe-assembly illustrated in FIG. 10 encodes the information 3'-T-T-A-C-G-A-C-G-5'. Note, for clarity in FIG. 10, only a few of the many 210, 322, 324, 326, 328, 350, 360, 940, and 950 are labeled.

It is often beneficial to repeat boxes 43040 and 43050, in that order, using different subsets of labeled-probe-assemblies, and/or different hybridization conditions and solutions, and/or different stringency washes. Different subsets of labeled-probe-assemblies, with each subset having different probe sequences, can be hybridized to the sample on each cycle through 43040-43050. When multiple hybridization-extension cycles are used, typically two cycle are used, such that the subset of labeled-probe-assemblies used in the first cycle plus those used in the second cycle constitute a complete, spanning, set of labeled-probe-assemblies. Breaking the complete set into two subsets can be beneficial, especially when the two subsets contain complementary probe sequences. This eliminates competition due to probe-to-probe hybridization. The optional repetition of boxes 43040-43050 is illustrated in FIG. 43 as the dashed line extending from the output of 43050 to the input of 43040.

Box 43060 of FIG. 43 covers the steps of reading-out the information encoded along the labeled-probe-assemblies. In the preferred embodiment, the readout apparatus is a SEM (Scanning Electron Microscope), and the processes of sample preparation and imaging follow standard electron microscopy protocols available in the literature. First the substrate, with bound sample DNA molecules and labeled-probe-assemblies, is sputter coated with platinum in a rotary coater. Next, the top layer of the substrate, the carbon film, is scribed around the perimeter of the substrate and floated off the mica surface. This can be done in a beaker filled with water, and the carbon film floats on the surface of the water. An electron microscope sample grid is used to collect the floating carbon film. The electron microscope sample grid with carbon film is then dried and loaded into the SEM. SEM images of areas of the carbon substrate appear as illustrated in FIG. 10, with the sample DNA molecules appearing as faint approximately straight long lines, and multiple labeled-probe-assemblies appearing as faint approximately straight lines with visible beads, individual Lac proteins bound to the labeled-probe-assemblies, at discrete locations along these lines. The orientation of the labeled-probe-assemblies is approximately perpendicular to the axis of the sample DNA molecules. Multiple SEM images are recorded covering all sample DNA molecules of interest on the substrate. As shown in FIG. 11, illustrating the SEM apparatus 1100, the relative locations of the images over the carbon film are determined by recording the number of turns of the X and Y axis precision micrometers, 1110 and 1120, used to move the sample under the electron beam. Additional information on relative displacement between images is provided by spacing the images such that there is overlap between adjacent images and aligning identical features in each image, either manually with printed images or using software and digitized images. In addition to the location of the image on the substrate, the information extracted from each SEM image are the distances along the sample DNA molecules between labeled-probe-assemblies and the locations of beads, individual Lac proteins, along each labeled-probe-assembly. For each labeled-probe-assembly, the locations of the Lac proteins along the assembly are analyzed to determine the base sequence information encoded. Hence, the information obtained for each sample DNA molecule includes multiple probe-length base sequences, the map of the order of these probe-length sequences along the sample DNA molecule, and the physical map of approximate distances between them. This information is collected from multiple copies of each type of sample DNA molecule, a process referred to as over-sampling, thus insuring sufficient overlap of sequence information to reconstruct the entire sequence of each of the different types of sample DNA molecules. The information is collected and stored on computer 1130, illustrated in FIG. 11, which is connected to the SEM detector and can be connected to the Internet. Computer 1130 can also be used for data analysis with data displayed on monitor 1140.

Box 43070 of FIG. 43 covers the analysis of the information recovered in step 43060 and reconstruction of the entire sequence of whole sample DNA molecules. Computer programs for reconstructing the entire sequence of whole sample DNA molecules by finding the highest probability alignment of multiple overlapping short sequences have been developed to support "Shotgun" sequencing protocols and "contig" mapping. These same programs can be applied to the information gathered in step 43060. Additionally, multiple alignment programs can be further optimized by using the order and physical distance between labeled-probe-assemblies, part of the data collected in step 43060, and translating these distances into approximate numbers of bases along the sample DNA molecule (typically 2.4 kb/micron) between lengths of sequence information. Analysis of the data collected in step 43060 provides the base sequence of the whole sample DNA molecules. The raw and analyzed sequence data are stored to computer memory and can be made available for use on other computers and analysis programs and with other data sets, and can be transmitted by electronic and physical means to other computer systems and the Internet.

Box 43080 of FIG. 43 covers the optional repetition of the steps in boxes 43032 to 43070 (or 43040 to 43070). This is particularly relevant to process-flows in which staining is not by sputtered metal, or, in cases where sputtered metal staining is used, boxes 43032 to 43050 can be repeated, prior to box 43060 (i.e. box 43080 would be placed between boxes 43050 and 43060 in FIG. 43). Boxes 43032 to 43070 are repeated as beneficial, bleaching the stain, consuming the labeling proteins, and/or removing any labeled-probe-assemblies on the substrate prior to adding new labeled-probe-assemblies. Alternately, extend labeled-probe-assemblies in opposite, or alternate, direction from the direction in which labeled-probe-assemblies were extended in previous cycles.

The methods, assemblies, and apparatus' detailed in this and other sections illustrate specific embodiments of more general forms and procedures. Many alternatives are possible, and some are presented in the sections that follow. In addition, many alternatives will become apparent upon consideration of the embodiments provided. The embodiments provided are not intended to limit the invention, but rather to detail specific cases from which further alternate embodiments will be apparent. For example, many further alternate embodiments can be constructed by rearranging the order of specific process steps within the embodiments presented, and many more can be created by mixing and matching process steps, assemblies, and apparatus' between two or more of the specific embodiments. Furthermore, an understanding of the fundamental processes, assemblies, and apparatus' presented allows their extension beyond simple combinatorics to new materials, equipment, and techniques.

Description and Operation

Alternate Embodiments

Alternate Variations of the Preferred Embodiment

Assembly Layout and Information Encoding Protocol
Many alternate layouts and information encoding protocols for labeled-probe-assemblies are detailed elsewhere in this document.
One simple and space efficient alternative to that described above has equal length spaces between central groupings of Lac protein binding sequences, and hence the length of each region 220, of FIG. 2, is dependent on its encoded base.
High affinity binding sequences other than O1 can be used in regions 230, of FIG. 2, such as R1, etc.
Sequence-specific DNA binding proteins other than *Ecoli* wild-type Lac protein can be employed, such as, Lac protein from other sources and modified Lac proteins, Trp repressor protein, Gal repressor protein, and CAP. In which case, the base sequence of the regions 230, of FIG. 2, is that which has high binding affinity for the specific proteins used. Furthermore, a mixture of different types of sequence-specific DNA-binding proteins, with shared or unique high affinity binding sequences can be employed.

Alternate probes on Labeled-probe-assemblies for various applications
Probes on both ends of assembly, or multiple probes on long linkers connected to one label-assembly (to increase rate of labeling)
For sequencing by hybridization, set of all probes makes up a complete set of N-mers (ssDNA, ssRNA, ssPNA, or combination of these), or repeated application, each using a different subsets of N-mers (so as to limit probe-to-probe hybridization and so increase the concentration of probe available for hybridization with target)
For sequence recognition, probe can be protein that will bind to specific ss or dsDNA or RNA sequences.
For tagging specific proteins and other molecules, probe can be anti-body to protein, biotin, avidin, etc.

Method of Use
There are many other uses for labeled-probe-assemblies, including:
Detection and determination of SNPs (single nucleotide polymorphisms)
Determination of allele type
FISH (Fiber in-situ hybridization)
Determination a short sections of sequence Method of Use in Sequencing
FIG. 43 presents the preferred process flow for sequencing of dsDNA samples. In step 43010, DNA is collected and prepared for subsequent process steps. Sample collection usually entails the collection of a tissue sample or harvesting of cells or plaques with the desired DNA, and may include generation of cDNA from cellular RNA. DNA can be extracted and isolated, or generated from RNA templates, using any suitable protocol, of which many standard protocols exist. An advantage of the sequencing method disclosed here is that very long DNA molecules can be sequenced, and in addition, it is beneficial to have the sample DNA molecules be as long as possible. Hence, DNA extraction and isolation protocols that tend to produce DNase-free, largely protein-free and solvent-free DNA molecules of high or maximal molecular weight are the best. Due to the flexibility and robustness of the overall sequencing process, extraction and isolation protocols that tend to produce shorter, lower molecular weight DNA molecules are also acceptable.

In step 43020 of FIG. 43, the substrate is fabricated. A number of different unique substrate types are possible, and for each substrate type, the downstream process steps are modified. Substrates may include non-deforming substrates, solid or flexible, preferably flat, preferably smooth, with or without a surface layer. Substrates may have strip or dots of avidin or streptavidin, or be a clean surface with no specific anchor molecules. Surface, in combination with the DNA extension solution, should promote extension of DNA molecules over the surface. Surface is preferably suitable for fixing, covalent and/or non-covalent bonding, of DNA to surface. Beneficially, substrate will have grid or other features visible to the readout hardware used to facilitate alignment of adjacent images captured by the readout hardware and to facilitate measurement of distances along the substrate and between labeled-probes.

In step 43020 of FIG. 43, the labeled-probe-assemblies are fabricated. In an alternate embodiment, during fabrication of labeled-probe-assemblies, the probe regions can be made single-stranded by use of 5'-to-3' directionally digesting exonucleases (resulting in 3'-overhanging probes) or 3'-to-5' exonucleases (resulting in 5'-overhanging probes).

Step 43030. Extend Sample dsDNA onto Substrate and Fix to Substrate
  Attach one of both ends of sample DNA molecules to substrate by:
    Anchor w biotin/avidin or streptavidin
    Anchor by modifying terminal P or OH, then cross-linking to substrate amine, sulfhydryl, or thiol group.
    Non-specific binding (such as by pH control as used in DNA combing or simple droplet spreading of sample) with no modification to ends of sample DNA (no biotinylation of sample DNA required)
  Extend by:
    Spreading, fluid spreading, droplet spreading
    Pull through meniscus
    Spin coating
    DNA Combing
    Flow to extend and change chemistry (pH, or cross-linking) to fix
    AC and/or DC Electric-field to extend
    Dry to fix, dry and heat to fix, UV-cross-link to fix, cross-linking to fix, change chemistry (pH or cross-linking additive) to fix Step 43032 Form Regions of ssDNA to Function as Hybridization Targets.
  Form ss nicks and/or ds breaks (by enzymatic, chemical, UV exposure, UV exposure with intercalated stain molecules such as Ethidium Bromide, patterned UV exposure, patterned or blanket e-beam or ion-beam (FIB) exposure), and treat with directional exonuclease (5'-to-3' or 3'-to-5')
    Limit extent of ss regions by adding dsDNA-binding proteins to nick/break procedure to protein footprint protection.
  Alternately, mechanically cleave substrate fixed dsDNA by stretching the substrate beyond the stain limit of DNA. This will form both blunt ends and overhanging ends, some of which will be usable as targets for probes. To increase the percentage of overhanging ends usable as targets, the sample may be treated with directional exonucleases (5'-to-3' or 3'-to-5').

Step 43040. Hybridize Labeled-Probe Assemblies to Sample DNA
  Optionally, ligate or cross-link probe to target or substrate
  Labeled-probe-assemblies can be a mixture of labeled-probe-assemblies with various, distinguishable stains, such that labeled-probes with different stains can be readout successfully, even where they are too close together to be spatially resolved.

Step 43050. Extend Labeled-Probe Assemblies and Fix.
  As per 43030, but approximately perpendicular to axis of extension along which sample DNA was extended in step 43030.
  Lac proteins can be bound to labeled-probe-assemblies prior to their hybridization to sample DNA (step 43040), after hybridization and before extension (as presented in detailed description above), or after extension and fixing of labeled-probe-assemblies to substrate (after step 43050)

Step 43060. Readout Label Data from Labeled-Probe Assemblies
  Use AFM (Atomic Force Microscope), STM (Scanning Tunneling Microscope), or other SPM (Scanning Probe Microscope) in place of SEM as the readout apparatus.
  Use multi-tip AFM, STM, or SPM in place of SEM as readout apparatus, where the multi-tip arrangement allows multiple locations on the substrate to be scanned simultaneously.
  Fluorescent microscopy to collect sequence data encoded along labeled-probe-assemblies with fluorescent stain, and to estimate number of bases along sample separating labeled-probes
  Use TEM (Transmission Electron Microscope) in place of SEM
  A computer controlled automated stage assembly can be implemented to automatically collect image and image-location data over selected areas of the substrate.

Step 43080. Optionally, Repeat Steps 43040 to 43070 as Beneficial
  Bleach or remove existing labeled-probe assemblies prior to repeating step 43040.
  May move step 43080 before step 43070.

Further Alternate Variations of the Method of Use for the Preferred Embodiment

Variations to Box 43010 of FIG. 43 include;
  Biotinylating the 5'-end(s) of the sample DNA molecules, instead of or in addition to the 3'-end(s) (5'-end labeling kits are commercially available from several sources including Vector Laboratories.)
  Using binding pairings other than biotin-avidin to anchor one or both ends of the sample molecules to the substrate, such as biotin-streptavidin, antigen-antibody combinations, sulfur-end-group—gold, and phosphorimidazolide—amine.
  Leaving the ends of the sample DNA un-modified, and extending the sample DNA molecules by means that rely on non-specific DNA-end to substrate binding, such as flow methods and DNA combing.
Variations to Box 43020 of FIG. 43 include;
  Replacing sample binding strip 630 of FIG. 6b with a low density coating of avidin or avidin-conjugated molecules covering some or all of the substrate surface.
  Fabricating substrate without sample binding strip 630, and instead relying on non-specific DNA to substrate binding.
  Fabricated substrate of cleaved Mica, without the carbon film, and using SEM (scanning electron microscopy), SPM (scanning probe microscopy), AFM (atomic force microscopy), or other techniques with nanometer-scale resolution, to detect and readout the encoded information.
Variations to Box 43030 of FIG. 43 include;
  Extending sample DNA over surface of substrate by fluid flow immediately followed by rapid drying
  Droplet spreading
  DNA combing
  Application of a DC or AC electric field followed by rapid drying Contact transfer to substrate from a surface layer containing Cytochrome C protein and sample DNA molecules and followed by rapid drying Tethering sample DNA to microsphere and extending DNA by moving microsphere with focused laser fields.

Fixing of the sample DNA to the surface can be accomplished by simple drying, as presented above, or by techniques such as: drying followed by heating (typically to approximately 80 C for several minutes or longer), UV-cross-linking, chemical cross-linking, application of Methylene Blue followed by UV exposure, application of methanol:acetic acid (3:1) fixative, etc. References for all these techniques are available in the literature.

Variations to Box 43032 of FIG. 43 include;

UV, chemical, or enzymatic nicking followed by nick expansion by directional, single-strand consuming dsDNA exonucleases Denaturing by exposure to high pH solution (typically of pH ~11.5-12) followed by cold rinses and rapid drying An Alternate Embodiment of Labeled-Probe-Assemblies and Methods for their Use A number of alternate embodiments of labeled-probe-assemblies and methods for their use are detailed below. In this section, the alternate embodiment presented uses fluorescent secondary probes to visibly label the labeled-probe-assemblies, instead of using Lac proteins as labels, and the readout apparatus uses fluorescent microscopy. In addition, short oligomers are hybridized to the sample DNA molecules and cross-linked to the substrate. The substrate is then deformed, stretched, pulled, expanded, flowed, and otherwise elongated, in order to spatially separate the oligomers and allow more sequence information to be extracted from each individual sample DNA molecule.

Layout of an Alternate Labeled-Probe-Assembly

FIG. 12 illustrates the layout of the alternate labeled-probe-assembly 1201. The assembly 1201 is fabricated of DNA and has two ssDNA probes, 1202 and 1203, with identical base sequence. Including two probes per labeled-probe-assembly increases their rate of hybridization to target sample DNA. The label-assembly portion of 1201 is made of dsDNA and includes a start indicator 1204, and, in this example, four base encoding regions 1205-1208, followed by end indicator 1209. For clarity of the illustration, each of the regions 1204-1209 is bounded by vertical lines. Note, as with all the types of labeled-probe-assemblies presented in this document, the number of base encoding regions is limited in the figures for clarity, while actual labeled-probe-assemblies can have many more base encoding regions, as well as fewer. The number of base encoding regions on a given labeled-probe-assembly is typically in the range of 2 to 100 or more, beneficially in the range of 4 to 50, and preferably in the range of 6 to 25. Each base encoding region 1205-1208, the start indicator 1204, and end indicator 1209 is of approximately equal length, typically in the range of 0.1 to 5.0 microns and preferably in the range of 0.25 to 1.0 microns, and the variation in length of the base encoding regions within a single labeled-probe-assembly is typically less than +/−10%, and preferably less than +/−5%, of the mean length. The minimum length is set by the limits of resolution set by specifics of the physical characteristics of the labeling molecules and readout apparatus, and lengths shorter than ~0.2 microns can be resolved using readout apparatus equipped with either a scanning UV-laser excitation probe or near-field optical probe.

Between probe 1202 and start indicator 1204, and between probe 1203 and end indicator 1209, there are typically short spacer, transition, regions that may include the recognition sequences of nicking enzymes and restriction enzymes used during the fabrication of the labeled-probe-assemblies. It is preferable to design these short spacer regions to be as short as practical. Furthermore, there may be short spacers between adjacent base encoding regions 1205-1208, and between 1204 and 1205, and 1208 and 1209. These spaces may be remnants of specifics of the manufacturing methodology and are not required for, or detrimental to, the information encoding protocol, and it is generally preferable to keep the labeled-probe-assemblies as short as possible while maintaining their manufacturability and functionality.

The base encoding regions 1205-1208, start indicator 1204, and end indicator 1209 are not directly stained. Hence, no staining is required during the manufacture of the labeled-probe-assemblies. Visualization, in this case by fluorescent staining, of the labeled-probe-assemblies is accomplished by hybridizing secondary labeled probes to some or all of regions 1204-1209, and it is these secondary labeled probes which are stained. Hence, the base sequences along each of the regions 1204-1209 is specified during manufacture, and secondary labeled probes are fabricated with the complementary sequences. During use of the labeled-probe-assemblies, secondary labeled probes are hybridized to some or all of regions 1204-1209, and it is these secondary labeled probes that are stained and visualized by the readout apparatus.

Information Encoding Protocol of an Alternate Labeled-Probe-Assembly

An alternate information encoding protocol is presented for these labeled-probe-assemblies. In this case, two distinguishable fluorescent stain types are used, fluorescein and rhodamine, as well as unstained regions, to form four distinguishable fluorescent responses, fluorescein only (green), rhodamine only (red), a mixture of fluorescein and rhodamine (yellow), and unstained (black). As noted above, the labeled-probe-assemblies are not stained directly, rather, the base sequences along each base encoding region, the start indicator, and end indicator, are specified, predetermined. Secondary labeled probes are fabricated with base sequences complementary to the appropriate base encoding regions, and it is the secondary labeled probes that are stained and detected.

The base sequence information encoding protocol as visualized by the readout apparatus is as follows; each encoded adenine (A) is represented by one base encoding region of the labeled-probe-assembly stained with fluorescein only (green fluorescence), each encoded (T) is represented by one base encoding region stained with rhodamine only (red fluorescence), each encoded (C) is represented by one base encoding region stained with both fluorescein and rhodamine (yellow), and each encoded (G) is represented by one base encoding region left unstained (no fluorescence). Further, the start indicator is stained as an (A) with fluorescein only, and the end indicator is stained as a (T) with rhodamine only. The start indicator indicates the 3' end of the encoded sequence, and the encoded sequence is the base complement of the labeled-probe-assembly's probe sequence (i.e. the base sequence of the target to which the probe will hybridize).

To affect this protocol, only three types of secondary labeled probes, with three unique base sequences (pA, pT, and pC), are required. Likewise, only four base sequences (sA, sT, sC, and sG) are required to define the base encoding regions 1205-1208, start indicator 1204, and end indicator 1209. Each region encoding (A) is fabricated with the specific sequence (sA), similarly, each region encoding (T) is fabricated with the specific sequence (sT), which is different, has little homology with, the other specific base encoding sequences, and sequences (sC) and (sG) are similarly defined. These sequences are in dsDNA, hence the corresponding secondary labeled probes (pA), (pT), and (pC) have matching (identical or a high degree of homology) dsDNA sequences to (sA), (sT), and (sC), respectively. To prevent incorrect labeling, the sequences (sA), (sT), (sC), and (sG) are designed with minimal homology. Finally, as mentioned above, there may be short spacer or transition regions between adjacent base encoding regions.

An example is illustrated in FIG. 12. In this example, start indicator 1204 and base encoding region 1205 are fabricated with base sequence (sA), end indicator 1209 and base encoding region 1206 are fabricated with dsDNA base sequence (sT), base encoding region 1207 is fabricated with sequence (sC), and, base encoding region 1208 is fabricated with sequence (sG). Prior to reading out the encoded information, secondary labeled probes with base sequence (pA) will be hybridized to regions 1204 and 1205, secondary labeled probes with base sequence (pT) will be hybridized to regions 1206 and 1209, and a secondary labeled probe with base sequence (pC) will be hybridized to region 1207. Hence, in FIG. 12, the encoded sequence is 3'-A-T-C-G-5'.

Method of Manufacture of Alternate Labeled-Probe-Assemblies and Secondary Labeled Probes As with the other embodiments presented, standard laboratory techniques in cell and molecular biology can be applied to fabricate the labeled-probe-assemblies and secondary labeled probes. In general, master labeled-probe-assemblies are assembled by ligating together sections of (sA), (sT), (sC), and (sG), in the proper order onto synthetically or biologically derived probe sequences. The dsDNA sequences (sA), (sT), (sC), and (sG) can be derived from biologic sources, usually by restriction enzyme excision from plasmids or natural sources, or they can by synthesized, or sequences derived from biologic sources can be manipulated and modified by techniques from bioengineering and molecular biology. The master labeled-probe-assemblies can then be amplified by standard cloning and/or PCR processes, and the product labeled-probe-assemblies extracted from the amplification vectors by standard techniques using commercially available reagents and protocols.

Note that once the master labeled-probe-assemblies are assembled, labeled-probe-assemblies with different sequences can be mixed together, amplified together in the same vessel (PCR and/or cloning), extracted together, purified together, and stored and used together. Hence, once the master copies of all the different labeled-probe-assemblies are fabricated, each in its own vessel, many can be mixed together and processed simultaneously in one, or a few, vessels. Labeled-probe-assemblies that can use the same restriction enzymes during extraction and uncovering of the probes, can be processed in the same vessel. Hence, only a few vessels are required to amplify and process all the types of labeled-probe-assemblies that include a complete set of possible probe sequences of a given length. To limit probe-to-probe hybridization during use of the labeled-probe-assemblies, the complete set of labeled-probe-assemblies can be processed as two or more subsets, where members within each subset have non-complementary probe sequences. The potential to simultaneously process, amplify, extract, and store entire sets and subsets of labeled-probe-assemblies in a small number of vessels provides considerable benefit to low cost production.

In one embodiment, the labeled-probe-assemblies are dephosphorylated, 5'-P is removed leaving 5'-OH, prior to use. During use, dephosphorylated labeled-probe-assemblies can be ligated to substrate bound oligomers, without ligating pairs of labeled-probe-assemblies to each other. Dephosphorylation can be conducted using enzymes with phosphatase activity, such as the alkaline phosphatases Bacterial Alkaline Phosphatase (BAP) and Calf Intestine alkaline Phosphatase (CIP), using existing standard protocols and commercially available materials.

Secondary labeled probes, with dsDNA sequences (pA), (pT), and (pC), typically have the same sequences as (sA), (sT), and (sC), respectively, and hence are derived by the same techniques as (sA), (sT), and (sC). In order to label these three types of secondary labeled probes, each of the sequences (pA), (pT), and (pC) is amplified in separate containers by cloning and/or PCR. The secondary probe sequences are then extracted from the cloning vectors and labeled with either biotin-dUTP (Boehringer Mannheim Biochemicals), or digoxigenin-dUTP (Boehringer Mannheim Biochemicals), or both, by nick translation or random primer extension. All secondary labeled probes (pA) are labeled with biotin-dUTP, probes (pT) are labeled with digoxigenin-dUTP, and probes (pC) are labeled with both. An acceptable procedure is presented in Parra, I., Windle, B., Nature Genetics (5):17 21 (1993). Per this procedure, fluorescent stains are conjugated to the secondary labeled probes after they have been hybridized to the labeled-probe-assemblies. In this case, fluorescein-avidin DN (Vector Labs) and rhodamine-labeled anti-digoxigenin Fab fragment (Boehringer Mannheim Biochemicals) are used to stain the secondary labeled probes. Many alternate labeling and staining procedures are available commercially and in the literature, such as described in Weier, H-U. G. et al., Human Molecular Genetics (4)10:1903 1910 (1995).

Method of Use of an Alternate Labeled-Probe-Assembly—Including Deformation of Substrate One method of use is presented in the process flow diagram of FIG. 44. The process is designed for the sequencing of single-strand and double-strand DNA samples and includes the deformation of the substrate to spatially separate fragments of the sample DNA or oligomers hybridized to the sample DNA, allowing more sequence information to be extracted from each individual sample DNA molecule. This process shares several of the same steps as previously presented in and described for FIG. 43, and hence the description of FIG. 44 will focus on those steps that are unique to FIG. 44.

Box 44010 of FIG. 44, describes the collection and preparation of sample DNA, and the processes described for box 43010 of FIG. 43 can be used, including the addition of biotin to one or both ends of the sample DNA molecules.

Box 44020 of FIG. 44 covers the fabrication of labeled-probe-assemblies and fabrication and preparation of a substrate. Fabrication of the labeled-probe-assemblies is detailed elsewhere in this document and is not repeated here. Note that one or more unique sets of labeled-probe-assemblies can be used, each unique set consisting of labeled-probe-assemblies with different sets of probes, different probe sequences and/or lengths. The substrate is fabricated to be deformed, flowed, stretched, expanded, or otherwise elongated. Suitable substrates are formed from low-melting point, non-water soluble, materials and mixtures of such materials, that include at least one component that has a functional binding-group for binding of the DNA and end-modified oligomers, described in box 44032, below. The melting point of the substrate is typically selected to be in the range of 25 C to 100

C, and preferably in the range of 40 C to 70 C, however, lower and higher melting point compounds can also be used. Functional binding-groups that facilitate sample and oligomer binding include primary and secondary amines, and terminal vinyl, carboxyl, hydroxy, sulfhydryl, thiol, and phosphoranate end-groups, and common cross-linker groups such as maleimide end-group and hydroxysuccinimide ester end-group. It is also beneficial if the compounds are waxy or amorphous in nature, with a softening point temperature proceeding melting to a liquid. The substrate can be fabricated as a continuous homogeneous material or mixture of materials, or as an assembly with two or more layers. A two layer substrate assembly usually is fabricated with a thicker base layer, typically composed of wax, and a thin surface layer composed of a non-water-soluble material with functional binding groups. Suitable component materials that do not include functional binding groups include waxes, synthetic waxes, natural waxes, paraffin wax, eicosane, docosane, and other non-water soluble, and preferably waxy, hydrocarbons, lipids, phosphatidylcholine, cholesterol, etc. Suitable component materials that include a functional binding-group include 1-octadecylamine, 1-octadecanethiol, 1-eicosanol, 1-docosene, eicosanoic acid, phosphatidylethanolamine (PE), modified phospholipids such as those from Avanti Polar Lipids, N-Dodecanylamine-PE, Phosphatidylthioethanol, and N-MCC-PE. The preferred substrate material for this embodiment is the mixture of 80-98% paraffin wax and 2-20% 1-octadecylamine, and FIG. 13a illustrates the substrate 1300. The paraffin wax is selected to have a melting point near that of 1-octadecylamine. The substrate is formed by casting in a silicone mold. After removing from the mold, the substrate is annealed in water at temperature of 45 C for several hours. An alternate substrate, which has a two-layer layout like in FIG. 6a, has a thick layer of synthetic wax covered with a thin layer of Dodecanylamine-phosphatidylethanolamine. This substrate can be made by first casting the wax portion, and then depositing a monolayer of Dodecanylamine-phosphatidylethanolamine on top using the LB film technique. The wax is selected to have a melting point roughly equal to that of the Dodecanylamine-phosphatidylethanolamine. Other alternate substrates include mixtures of 70-100% phosphatidylethanolamine with 0-30% cholesterol.

Substrates are typically made 1 mm to 4 mm thick, with length roughly 5 millimeters longer that the longest sample DNA molecule, and width roughly 10 millimeters wider than is needed to hold the desired number of sample DNA molecules. For sequencing of entire chromosomes and high molecular weight chromosome fragments, typical dimensions are 3 mm thick, 30 mm long, and 50 mm wide. As sample extraction techniques improve, longer substrates will be used. These dimensions provide one example, and the exact dimensions are not critical.

Once the substrate is formed, a narrow strip of avidin or streptavidin 630 is printed and dried onto the substrate 1300, resulting in the substrate assembly 1302 illustrated in FIG. 13b. This narrow strip of avidin or streptavidin 630 is printed using the straight edge of a silicone rubber (PDMS) sheet as a rubber-stamp. To form the stamp, a sheet of ~¼" thick silicone rubber is cut in a straight line with a sharp razor blade at a 90 degree angle to the surface of the sheet. The end of the silicone rubber stamp is dipped into an aqueous solution containing either avidin or streptavidin. The solution being standard storage solution for the avidin or streptavidin. The solution is allowed to dry on the silicone rubber. Then the silicone sheet is held at a 45 degree angle relative to the surface of the substrate, and one edge of the avidin treated end is pressed gently against the surface of the substrate. The stamp is held in place against the substrate for approximately 30 minutes in order to transfer some of the avidin, or streptavidin, to the surface of the substrate, after which the stamp is removed.

In FIG. 44, box 44030 covers extension of the sample dsDNA onto the surface of the substrate and fixing the extended sample DNA to the surface. Many methods for extending DNA over the surface of a substrate are available in the literature. In one embodiment, an apparatus such as that illustrated in FIGS. 7a and 7b is used, except that substrate assembly 1302 is used instead of substrate assembly 602. Referring to FIGS. 7a and 7b, the substrate assembly 1302 (shown as 602 in FIGS. 7a and 7b) is fixed into the vessel using clips 710 such that the line of avidin 630 on the substrate 1300 is oriented approximately parallel to the base of the vessel 700 and is toward the top of the substrate. The vessel 700 is made of Teflon, polystyrene, silanized-glass, or other such material that minimizes absorption of biotin and DNA. Fluid can enter and exit the vessel from the bottom through tube 720. Draining the vessel is accomplished by opening metering valve 730, and the vessel can be filled by either adding fluid directly into the top of the vessel, using a pipette or syringe, for example, or by opening metering valve 740 to allow fluid in reservoir 750 to flow into the vessel. The height and width of the inside of the vessel 700 is made sufficient to contain the substrate. The width of the tank in the direction perpendicular to the substrate surface is typically in the range of $\frac{1}{10}$ to $\frac{1}{4}$ the height of substrate, and can be made thinner to reduce volume when sample DNA is limited.

Biotinylated sample DNA in an aqueous solution, such as 10 mM Tris-HCl, pH 8.0, 1 mM EDTA, or 10:1 water:AF-solution (1% p-phenylenediamine, 15 mM NaCl, 1 mM $H_2PO_4$, pH 8.0, 90% glycerol), is added slowly to the vessel. To limit non-specific binding of sample DNA to the substrate, solution pH should be 7.0 or greater, and solution pH should be adjusted prior to introduction into the vessel. When handling, transferring, the DNA solution, care should be taken to minimize fluid turbulence and shear so as to limit cleavage of the sample DNA. A pipette can be used to transfer the sample from its storage container into the vessel. The mixture is allowed to stand in the vessel for approximately 10 minutes or longer, to allow the biotinylated DNA to bind to the avidin, or streptavidin, on the substrate, and then the vessel is placed in a refrigerator and cooled to 4 C. To extend the sample DNA molecules, fluid is slowly drained from the bottom of the vessel by opening valve 730 as shown in FIG. 7a. Valve 730 is adjusted so that the meniscus within the vessel lowers at a rate of approximately 1 mm per hour, although this rate is not critical. Sample DNA molecules, that are bound at one end to the substrate, are extended over the substrate surface as the level of the solution recedes. The sample DNA molecules are extended in a direction approximately perpendicular to the surface of the solution. Once the vessel has been drained, the substrate is dried thoroughly in order to fix the sample DNA to the substrate. FIGS. 8a-c illustrate the progression from biotinylated sample DNA bound to the avidin on the substrate, as illustrated in FIG. 8a, to partially extended sample DNA as illustrated in FIG. 8b, and finally, to fully extended sample DNA as illustrated in FIG. 8c. Note one exception to FIGS. 8a-c is that substrate assembly 1302 is used here, instead of substrate assembly 602 as indicated in the figures. In the FIGS. 8a-c, extending sample DNA molecules 830 are end-bonded to avidin molecules on the printed avidin line 630. The avidin-biotin-sample-DNA conjugates are shown as dots 810, and the solution meniscus is shown as the line 820. After completion of the sample DNA extension, as illustrated in FIG. 8c, the extended sample DNA molecules 830 are extended approximately along a single direction.

In FIG. 44, box 44032 covers the hybridization of probe length oligomers to the sample DNA molecules. The oligomers may be DNA, RNA, or PNA (peptide nucleic acid), and typically are of all sequences complementary to all the various labeled-probe-assembly probe-sequences to be used. The oligomers are modified as necessary to facilitate binding to the substrate. Typically, this is accomplished by modifying the 3' end of the oligomers to add a sulfhydryl group, which can accomplished during the solid phase synthesis of the oligomers or by use of Terminal Transferase addition of a modified base (see kits and protocols by Enzo Life Sciences Incorporated, Farmingdale, N.Y., BioProbe 3'-Oligonucleotide Labeling System and other products, and Vector Laboratories Incorporated, Burlingame, Calif., 3' EndTag DNA Labeling System.). Other suitable end modifications and substrate binding methodologies are available, and include converting the 5'-P to 5'-phosphorimidazolide and binding this to substrate amine groups using a water soluble carbodiimide in imidazole buffer, as described in Chu, B. C. F., Wahl, G. M., Orgel, L. E., Nucleic Acid Research (11)18:6513 6529 (1983) and similar chemistries in "Covalent Binding of DNA to CovaLink NH Methods and Applications", Bulletin No. 10(1), (1997), NUNC Brand Products, Nalge Nunc International, and modification of 5'-P to a reactive sulfur group with the 5' EndTag Nucleic Acid Labeling System by Vector Laboratories.

The hybridization step of box 44032, FIG. 44, can proceed directly on ssDNA molecules and when using RNA or PNA oligomers. In the case of dsDNA sample molecules with DNA oligomers, the dsDNA molecules can be denatured with alkali by submerging the substrate for approximately 5 minutes into an aqueous solution (0.02M Na2CO3, 0.005M Na2EDTA) with pH adjusted with 1M NaOH to approximately a pH of 12.0, then briefly rinsed with cold deionized water and quickly dried under blowing nitrogen.

Prior to use in step 44032, the oligomers are added to the hybridization solution and heated so as to denature any oligomer-to-oligomer hybrids that may have annealed during storage. Heating to 75 C in the SSC hybridization solution for 5 minutes is typically sufficient, but the optimum temperature will depend on the chemistry of the hybridization solution used, and length and G-C content of the oligomers. Many acceptable hybridization solution formulations are available in the literature, see for example Chapter 9, "Hybridization Analysis" in Molecular Biology Labfax (1990). The choice of an optimum solution depends on several variables, including the length of the oligomers, whether the oligomers or sample molecules are DNA, RNA, or PNA, and variation in G-C to A-T ratio of the various oligomers. For instance, three typical hybridization solution, any of which can be used, include SSC hybridization solution (sodium chloride/sodium citrate based solution of 0.45M NaCl, 0.045M trisodium citrate 2H2O, pH adjusted to 7.0 with 0.15M HCl, 0.05% sodium pyrophosphate), diluted AF-solution (10:1 SSC hybridization solution: AF-solution (1% p-phenylenediamine, 15 mM NaCl, 1 mM H2PO4, pH 8.0, 90% glycerol), and TMAC (Tetramethylammonium chloride) based hybridization solution. For example, see recipe in Short Protocols in Molecular Biology, 4th ed., F. M. Ausubel, et. al., John Wiley & Sons, Inc., 1999, page A1-40. Commercially available solutions are also acceptable, as are additives to speed hybridization and increase stringency, such as dextran sulfate (Mol. wt 500,000) and increased sodium-salts. Typically, solution pH is kept above 7.0 to limit binding of free DNA molecules, sample or oligomers, to the substrate. TMAC based solution is used primarily in cases where the difference in binding energy between G-C rich and poor oligomers causes issues with stringency. The SSC hybridization solution is typically used.

The hybridization step 44032 can be conducted in any suitable vessel, such as a polystyrene dish. With the substrate in the vessel, the hybridization solution with oligomers is added to cover at least that portion of the substrate with extended sample DNA molecules. Hybridization is allowed to continue until the desired percentage of hybridization interaction has completed or the process has saturated. Typically, the hybridization reaction is given 16 to 36 hours, and longer or shorter times are acceptable. Following hybridization, stringency rinses may be employed to remove any incorrectly hybridized oligomer. Many examples of stringency rinses and procedures are available in the literature.

Following hybridization, excess oligomers are removed, by for example gentle rinsing of the substrate, and the hybridized oligomers are then cross-linked to the substrate. Heterobifunctional (amine and sulfhydryl reactivity) cross-linking agents such as 4-(N-Maleimidomethyl)cyclohexane-1-carboxylic acid 3-sulfo-N-hydroxysuccinimide ester sodium salt (($C_{16}H_{17}N_2O_9SNa$) Sigma-Aldrich catalog number M 6035, Sigma-Aldrich Co. with protocol reference (Hashida, S., et. al., J. Applied Biochem., vol 6, p 56-63 (1984)) are used to link the oligomers by their terminal sulfhydryl group to the amine groups on the substrate surface. If an alternate oligomer binding-group modification is used, then the corresponding cross-linking agent is employed, such as a water-soluble carbodiimide in imidazole buffer when the oligomer terminal binding group is 5'-phosphorimidazolide.

Once the oligomers that are hybridized to the sample DNA have been cross-linked to the substrate, the sample DNA is no longer required, and the sample DNA can be removed (although this is not required). In cases where RNA and PNA oligomers are used, the sample DNA can be removed by consuming the DNA with RNase-free DNase enzymes. In cases where DNA oligomers are used, it is simplest and acceptable to skip this step and leave the sample DNA on the substrate.

In the next set of steps, box 44035 of FIG. 44, the substrate is elongated, deformed, along the same direction as the sample DNA molecules are extended. Elongating the substrate will separate adjacent substrate bound oligomers such that the labeled-probe-assemblies that hybridize to these oligomers can be resolved by the readout apparatus. The amount of elongation needed depends on the stains employed, the readout apparatus hardware, and the length of the oligomers. Typically, the substrate will be elongated between 10-3000 times its original length, and usually between 50-1000 times, and preferably between 70-300 times its original length. Any method for elongating the substrate can be used. One method for accomplishing this is detailed in FIG. 52, and this method employs multiple repeated stages, each of limited substrate deformation.

Box 52000 of FIG. 52 covers all the steps covered in FIG. 44 up to box 44035, the fabrication and preparation of the substrate with target material, in this case substrate bound oligomers, on the substrate.

Box 52010 of FIG. 52 covers the mounting of the substrate, face down, on a stretchable-substrate-support, and the mounting of the stretchable-substrate-support into a support-stretching fixture. The stretchable-substrate-support is typically a sheet or film of material, larger than the substrate, with significant ultimate elongation, and that is non-reacting with the substrate materials and oligomers. There are many candidate materials including, silicone rubber, silicone gel, Teflon skived tape, low Tg thermoplastics like polyethylacetate, various commercial plastic wraps, and various elastomeric materials. The stretchable-substrate-support may be coated with a thin layer of a non-reacting, non-stick material prior to use, such as silicone oil, petroleum jelly, or mineral oil. One suitable stretchable-substrate-support is ⅛ inch thick super-soft silicone rubber (durometer 10A, available from McMaster-Carr Supply Company in 6 inch wide×36 inches long strips, catalog number 5963K16 at www.mcmaster-carr.com). The dimensions of the stretchable-substrate-support are not critical, so long as it is large enough to fit the substrate. One set of dimension that is acceptable has the substrate-support 100 mm longer and wider than the substrate. Prior to use, the stretchable-substrate-support can be cleaned with soap and water, followed by IPA, then dried. The substrate is mounted centered onto the stretchable-substrate-support, oligomer side against the stretchable-substrate-support, by manually pressing and working out any bubbles between the substrate and stretchable-substrate-support. Mild heating of the stretchable-substrate-support to just soften the substrate can facilitate this operation.

FIG. 14a illustrates the support-stretching fixture 1400, in the relaxed position, with the stretchable-substrate-support 1402 mounted. The stretchable-substrate-support 1402 is mounted into the support-stretching fixture 1400 by wrapping the ends of the stretchable-substrate-support 1402 around each of end-rods 1404 several times. Substrate 1302 is mounted onto stretchable-substrate-support 1402. One of the end-rods 1404 is attached to frame 1412, and the other end-rod 1404 is attached to actuator strut 1408, which is the actuator strut for pneumatic cylinder 1410. Pneumatic cylinder 1410 is connected to frame 1412. Pressurized air in pressure tank 1418 is coupled to pneumatic cylinder 1410 through control valve 1416 and flexible hose 1414. When control valve 1416 is opened, pressurized air is supplied to pneumatic cylinder 1410, which causes actuator strut 1408 to be forced into the pneumatic cylinder 1410. The motion is limited by adjustable stop 1406.

Box 52020 of FIG. 52 covers the heating of the substrate 1302 and stretchable-substrate-support 1402 until substrate 1302 is softened sufficiently to allow plastic deformation or liquid flow when the stretchable-substrate-support 1402 is stretched. As illustrated in FIG. 14b, while mounted in the support-stretching fixture 1400, the substrate 1302 and stretchable-substrate-support 1402 are heated by placing the stretchable-substrate-support 1402 over temperature-controlled electric hotplate 1420. Prior to use, the hotplate 1420 is heated to the desired temperature, typically around the melting point of the substrate. Temperature-controlled electric hotplate 1420 can be a commercially available model, such as a standard laboratory hotplate.

Box 52030 of FIG. 52 covers the stretching of the stretchable-substrate-support 1402 by energizing pneumatic cylinder 1410 on the support-stretching fixture 1400, as illustrated in FIG. 14c. Referring to FIG. 14c, cylinder 1410 is energized as soon as substrate 1302 has reached the desired temperature and stretchable-substrate-support 1402 has been lifted off hotplate 1420. To energize cylinder 1410, valve 1416 is opened to allow pressurized air from tank 1418 to flow through hose 1414 into cylinder 1410. The stretchable-substrate-support 1402 is then stretched by a pre-determined amount, set by the location of adjustable stop 1406 along actuator strut 1408. The amount of stretching depends on the ultimate elongation capacity of the stretchable-substrate-support material and the desired total substrate elongation. With the referenced silicone stretchable-substrate-support, the stretchable-substrate-support can be stretched up to approximately 700% its relaxed length before risking failure, typically a maximum stretch of 500% is used. When stretching is complete, the stretchable-substrate-support 1402, still mounted to the support-stretching fixture 1400, is quickly lowered into a tank of cold water to rapidly solidify the substrate. This step is highlighted in box 52040 of FIG. 52. The valve 1416 remains open and the stretchable-substrate-support 1402 remains elongated until substrate 1302 is removed during process steps outlined in box 52050 of FIG. 52.

It is beneficial that the entire heating, stretching, and cooling cycle be short, hence the cylinder 1410 is provided with compressed gas of sufficient pressure and volume to allow rapid movement, typically >1 mm/sec, and preferably >10 mm/sec.

Box 52050 of FIG. 52 covers the removal of the elongated substrate from the stretched stretchable-substrate-support. This is accomplished by pressing on the backside of the stretchable-substrate-support to lift the edges of the substrate from the stretchable-substrate-support and then peeling off the substrate.

Box 52060 of FIG. 52 covers the adding of additional substrate material to the substrate in order to recover a more optimal thickness. Typically, optimal substrate thickness is in the range of 1 mm to 4 mm. Prior to adding substrate material, the substrate is mounted on a new stretchable-substrate-support, using the same method as presented above, and as before, with the oligomer side against the stretchable-substrate-support. Note that as the substrate has been stretched, the new stretchable-substrate-support will necessarily be longer that the used one. Once mounted, material is added to the backside of the substrate by slowly spraying, dripping, or brushing on melted substrate material. The stretchable-substrate-support should remain cool enough to prevent the front portion of the substrate, immediately adjacent to the oligomers, from melting. This can be done by adding material slowly, by periodically pouring cold water over the substrate, or by placing the stretchable-substrate-support on a cooled surface. Alternately, substrate material can be dissolved in a suitable high vapor pressure solvent and sprayed or brushed onto the substrate in thin layers, while allowing the solvent to evaporate between thin coats. Again, this should be done such that the oligomers remain fixed in place.

Box 52070 of FIG. 52 covers the repeated application of the process steps covered in boxes 52010 to 52060. Each time those steps are repeated, the substrate is elongated further, hence, the steps covered in boxes 52010 to 52060 are repeated, in order, until the substrate has been elongated by the desired total amount. For example, if the total desired elongation is 125 times, and the substrate is stretched 500%, or 5 times, in each cycle, then three cycles through 52010 to 52060 are all that is required (5*5*5=125). Four cycles would elongate the substrate by 625 times its original length, and intermediate values can be achieved by varying the per-cycle stretch to amplitudes other than 500%. This completes the description of FIG. 52.

Returning to FIG. 44, box 44040 covers the hybridization of labeled-probe-assemblies to the substrate bound oligomers. This is conducted in a vessel such as that illustrated in side-view cut-away in FIG. 7a and in front-view cut-away in FIG. 15. Vessel 1500 of FIG. 15 is equipped with the same connections, valves, and reservoirs as illustrated for vessel 700 of FIG. 7a, the only significant difference between vessels 1500 and 700 being the overall tank length. The other difference between FIGS. 7a and 15 is the substrate type, where FIG. 7a shows the two layer type 602, while FIG. 15 shows the single layer type 1302, but this is of little consequence as either type of substrate could be used in alternate embodiments of either of the process flows of FIGS. 43 and 44. The hybridization process is conducted in the same vessel that will be used to extend the hybridized labeled-probe-assemblies. This vessel is similar to the vessel used in 44030 to extend the sample DNA molecules, only widened to fit the elongated substrate. The substrate is placed in the vessel such that the axis of the extended sample DNA molecules, the axis of substrate elongation, is approximately perpendicular to the direction of gravity, parallel to the surface of the hybridization solution, as illustrated in FIG. 15. Hence, the orientation of the substrate within the vessel is rotated 90 degrees to that of the substrate during step 44030. Referring to FIG. 15, elongated substrate 1302 is held is vessel 1500 by clips 710 and sample DNA molecule binding strip 630 (typically a narrow strip of avidin molecules) is shown approximately perpendicular to the horizontal.

Prior to use in step 44040, the labeled-probe-assemblies are added to the hybridization solution and heated so as to denature any probe-to-probe hybrids that may have annealed during storage, however, the temperature and duration should not be so great as to denature entire labeled-probe-assemblies. The temperature should just exceed the calculated melting temperature for the most stable probe-to-probe hybrid, for example, for a probe length of 10 bases in SSC-based hybridization solution, the labeled-probe-assemblies should be heated to 45 C for one minute, then rapidly cooled to the desired hybridization temperature. The temperature used depends on the chemistry of the hybridization solution used. Many acceptable hybridization solution formulations are available in the literature. See for example Chapter 9 "Hybridization Analysis" in Molecular Biology Labfax (1990). The choice of an optimum solution depends on several variables, including the length of the probes, whether the probes or sample molecules are DNA, RNA, or PNA, and variation in G-C to A-T ratio of the various probes. For instance, three typical hybridization solution, any of which can be used, include SSC hybridization solution (sodium chloride/sodium citrate based solution of 0.45M NaCl, 0.045M trisodium citrate 2H2O, pH adjusted to 7.0 with 0.15M HCl, 0.05% sodium pyrophosphate), diluted AF-solution (10:1 SSC hybridization solution: AF-solution (1% p-phenylenediamine, 15 mM NaCl, 1 mM H2PO4, pH 8.0, 90% glycerol), and TMAC (Tetramethylammonium chloride) based hybridization solution. For example, see recipe in Short Protocols in Molecular Biology, 4th ed., F. M. Ausubel, et. al., John Wiley & Sons, Inc., 1999, page A1-40. Commercially available solutions are also acceptable, as are additives to speed hybridization and increase stringency, such as dextran sulfate (Mol. Wt 500,000) and increased sodium-salts. Typically, solution pH is kept above 7.0 to limit binding of free DNA molecules, sample or labeled-probe-assemblies, to the substrate. TMAC based solution is used primarily in cases where the difference in binding energy between G-C rich and poor probes causes issues with stringency. The SSC hybridization solution is typically used.

The hybridization solution with labeled-probe-assemblies is then added to the vessel to cover at least that portion of the substrate with bound oligomers. Hybridization is allowed to continue until the desired percentage of hybridization interaction has completed or the process has saturated. Typically, the hybridization reaction is given 18 to 48 hours, and longer or shorter times are acceptable. Following hybridization, stringency rinses may be employed to remove any incorrectly hybridized probe. Many examples of stringency rinses and procedures are available in the literature, however, it is important to limit physical agitation and fluid flows to minimize the probability of shearing the labeled-probe-assemblies. If used, stringency rinse solutions are slowly added at the top of the vessel by syringe while simultaneously draining fluid at approximately the same rate from the bottom drain tube 720 through valve 730 as illustrated in FIG. 7a.

In an alternate embodiment where RNA or DNA oligomers are used, Ligases are added to the vessel to ligate, covalently join, the hybridized labeled-probe-assemblies to the oligomers. The ligation step is readily conducted with commercially available ligation enzymes, solutions, and protocols. This can be done during the hybridization step, and allows hybridization to be conducted at higher temperature, and stringency, and also allows short temperature excursions to denature any labeled-probe-assembly to labeled-probe-assembly hybrids, and thus maintain a high hybridization rate to oligomers. This alternate embodiment is best combined with oligomers bound by their 3' ends, and with dephosphorylated labeled-probe-assemblies.

Box 44050 of FIG. 44 covers the extension of the oligomer-bound labeled-probe-assemblies onto the substrate, in a direction approximately perpendicular to the axis along which the substrate was elongated. For this process the substrate is kept in the same vessel as used in box 44040, and as illustrated in FIG. 15 and FIG. 7a. The hybridized labeled-probe-assemblies are extended over the substrate using a process similar to that detailed in step 44030. Valve 730 of illustration 7a is adjusted to allow the solution within the vessel to drain such that the meniscus within the vessel lowers at a rate of approximately 1 mm per hour, although this rate is not critical. Referring to FIG. 15, labeled-probe-assemblies that are bound at one end to substrate-bound oligomers are extended over the substrate surface as the level of the solution 1502 recedes, forming extended labeled-probe-assemblies 1504. The extended labeled-probe-assemblies 1504 are extended in a direction approximately perpendicular to the surface of the solution 1502. Once the vessel has been drained, the substrate is dried thoroughly in order to fix the extended labeled-probe-assemblies 1504 to the substrate 1302. The resulting configuration of substrate bound oligomers 1506 and hybridized and extended labeled-probe-assemblies 1504 is illustrated in FIG. 15 which also illustrates a close-up top-view of one portion of substrate 1302.

It can be beneficial to repeat boxes 44040 and 44050, in that order, using different subsets of labeled-probe-assemblies, and/or different hybridization conditions and solutions, and/or different stringency washes. Different subsets of labeled-probe-assemblies, with each subset having different probe sequences, can be hybridized to the sample on each cycle through 44040-44050. When multiple hybridization-extension cycles are used, typically two cycle are used, such that the labeled-probe-assemblies used in the first cycle plus those used in the second cycle constitute a complete, spanning, set of labeled-probe-assemblies. Breaking the complete set into two subsets can be beneficial, especially when the two subsets contain complementary probe sequences. This eliminates competition due to probe-to-probe hybridization. The optional repetition of boxes 44040-44050 is illustrated in FIG. 44 as the dashed line extending from the output of 44050 to the input of 44040.

Box 44055 of FIG. 44 covers the denaturing of the labeled-probe-assemblies, the hybridization of secondary labeled probes to the labeled-probes-assemblies, and the labeling of the secondary probes with fluorescent stains. These steps can be conducted in the same vessel as used for 44040 and 44050, or other suitable container, such as a polystyrene container. The labeled-probe-assemblies can be denatured with alkali by submerging the substrate for approximately 5 minutes into an aqueous solution (0.02M Na2CO3, 0.005M Na2EDTA)

with pH adjusted with 1M NaOH to approximately pH 12.0, then briefly rinsed with cold deionized water and dried. Note that the steps covered in box 44055 are specific to the type of staining method used, hybridization of secondary labeled probes, and box 44055 is not required when other staining methods are used. Other staining methods include use of stained proteins and directly stained labeled-probe-assemblies; both methods are discussed in this document.

Prior to hybridization, secondary labeled probes are added at a concentration of roughly 2 ng per micro-liter of a hybridization solution of 55% formamide, 10% dextran sulfate, and 1×SSC. The secondary probes are denatured by heating to roughly 70 C for 5 minutes, then the solution is cooled rapidly, on ice, until near the desire hybridization temperature, approximately 37 C or less than the melting temperature of the substrate. Once cool, the secondary probes in hybridization solution are added to the vessel containing the substrate to cover the substrate. Hybridization is continued for approximately 18 hours. Following hybridization, the substrate is washed twice in 50% formamide/2×SSC for 3 minutes, followed by two washes in 2×SSC for 2 minutes each, all at 45 C or less than the softening and melting temperature of the substrate. For low melting point substrates, hybridization and wash solutions can be adapted to lower temperature use by reducing salt and increasing formamide, as detailed in the literature on hybridization techniques.

Labeling of the secondary probes with fluorescent stains uses standard procedures for fluorescent labeling of biotin and digoxigenin. Many suitable procedures are available in the literature for which necessary chemicals and materials are commercially available. One suitable protocol for fluorescent detection is contained in the previously cited Parra, I., Windle, B., Nature Genetics (5): 17 21 (1993), which also provides a suitable hybridization procedure for joining the secondary probes to the labeled-probe-assemblies. The previously cited Weier, et al., Human Molecular Genetics (4)10: 1903 1910 (1995) also provides a suitable fluorescent detection procedure.

Box 44060 of FIG. 44 covers the steps of reading-out the information encoded along the labeled-probe-assemblies. In this embodiment, the readout apparatus is a fluorescent microscope, and the processes of sample preparation and imaging follow standard protocols available in the literature, such as those cited in the proceeding paragraph. A suitable readout apparatus is shown in FIG. 16, which illustrates fluorescent microscope and image capture assembly 1600. The substrate 1302, or a portion of it, with hybridized and extended labeled-probe-assemblies 1504, is loaded onto stage 1602, which is equipped with indicating micrometers 1604 that provide X-axis and Y-axis position information. Images through objective lens 1612 are captured with color digital image recording device 1606 that feeds its data to image processing, data analysis, and data storage programs in computer 1608. The image is focused using focus knob 1616, and an auto-focus mechanism can be implemented. The microscope is equipped with a suitable light source 1610, powered by power supply 1611, and excitation band-base and emission band-base filters located inside the microscope body 1614. Note 1606 can be a CCD or other type of digital camera, a video camera, and may include an image intensifier. Alternately, 1606 can be a film camera, in which case assembly 1600 is equipped with a digital image scanner for digitizing the film images and providing those data to computer 1608. Furthermore, an alternate data readout assembly can include a computer controlled automated stage assembly to automatically collect image and image-location data over selected areas of the substrate, and an automated substrate retrieval and loading system can be added.

The image in FIG. 17 shows an illustration of a portion of a typical image captured by the color digital image recording device 1606 of FIG. 16. More exactly, FIG. 17 illustrates the fluorescent signals from the secondary labeled probes that are hybridized to the extended labeled-probe-assemblies that are themselves hybridized to the oligomers associated with a portion of one sample DNA molecule. During the data acquisition steps of box 44060, in FIG. 44, multiple images are recorded, each at a different location on the substrate, and the X-Y coordinates are recorded from the indicating micrometers 1604, as illustrated in FIG. 16, for each image. Additional information on relative displacement between images is provided by spacing the images such that there is overlap between adjacent images and aligning identical features in each image, either manually with printed images or using software and digitized images. In addition to the location of the image on the substrate, the information extracted from each image, as illustrated in FIG. 17, are the distances 1702 along the substrate 1302 between extended labeled-probe-assemblies 1504 and the locations, length, and order of the green 1706, yellow 1708, and red 1710 fluorescent signals and the non-fluorescing (black) regions 1712 along each extended labeled-probe-assembly 1504. Referring to FIG. 17, as an example of the data collected by 1606 of FIG. 16, the right most extended labeled-probe-assembly 1504 is labeled with a color sequence that could be observed. From the information encoding protocol described above, the start indicator (3'-end) is labeled green 1706 and the end indicator is labeled red 1710, and otherwise, green 1706 encodes (A), red 1710 encodes (T), yellow 1708 encodes (C), and blank spaces 1712 encode (G). Hence the labeled sequence in FIG. 17 reads from top to bottom 3'-G-T-A-C-G-C-5'. Referring to FIG. 17, for clarity of the figure, not all extended labeled-probe-assemblies are labeled 1504, nor are all distances between extended labeled-probe-assemblies labeled 1702. Further, FIG. 17 is a black and white line drawing, whereas the actual images recorded by 1606 provide color (green, yellow, red, and black) information. For each labeled-probe-assembly, the length and order of the green, yellow, and red fluorescent signals along the assembly are analyzed to determine the base sequence information encoded. Hence, the information obtained for each sample DNA molecule includes multiple probe-length base sequences, the map of the order of these probe-length sequences along the sample DNA molecule, and the physical map of approximate distances between them. This information is collected from multiple copies of each type of sample DNA molecule, a process referred to as oversampling, thus insuring sufficient overlap of sequence information to reconstruct the entire sequence of each of the different types of sample DNA molecules.

Box 44070 of FIG. 44 covers the analysis of the information recovered in step 44060 and reconstruction of the entire sequence of whole sample DNA molecules. Computer programs for reconstructing the entire sequence of whole sample DNA molecules by finding the highest probability alignment of multiple overlapping short sequences have been developed to support "Shotgun" sequencing protocols and "contig" mapping. These same programs can be applied to the information gathered in step 44060. Additionally, multiple alignment programs can be further optimized by using the order of and physical distance between labeled-probe-assemblies, part of the data collected in step 44060, and translating these distances into approximate numbers of bases along the sample DNA molecule between lengths of sequence information. (Typically there are 2.4 kbp per micron of un-stretched substrate length, which is equal to 2.4 kbp per micron of stretched substrate, divided by the total substrate elongation.) Analysis of the data collected in step 44060 provides the base sequence of the whole sample DNA molecules. The raw and analyzed sequence data are stored to computer memory and can be made available for use on other computers and analysis programs and with other data sets, and can be transmitted by electronic and physical means and via the Internet to other computer systems.

Box 44080 of FIG. 44 covers an optional repeated cycle of the steps in boxes 44040 through 44070. Repeating these steps can allow additional sequence information to be collected from the sample. It can be useful if substrate bound oligomers remain that where not hybridized to labeled-probe-assemblies in the first cycle. Remaining un-hybridized oligomers can result from several causes including insufficient hybridization time and use of less than a complete set of labeled-probe-assemblies (probe sequences not spanning all oligomer sequences). Another possible variation is to use a different subset of labeled-probe-assemblies, with different probe sequences from those use during the first cycle, such that those used in the first cycle plus those used in the second cycle constitute a complete, spanning, set of labeled-probe-assemblies. Breaking a complete set into two subsets can be beneficial, especially when the two subsets contain complementary probe sequences. This eliminates competition due to probe-to-probe hybridization. In addition, box 43040 can be repeated using different sets of labeled-probe-assemblies, and/or different hybridization conditions and solutions, and/or different stringency washes.

In these cases, all steps covered in boxes 44040 through 44070 are conducted as in the first cycle, except in box 44040, the substrate is clipped into the hybridization/extension vessel upside-down, such that, in box 44050, any newly added labeled-probe-assemblies will be extended in the direction opposite to those of the first cycle. This allows the labeled-probe-assemblies added in the second cycle to be distinguished those from the first cycle, and hence, box 44080 could be placed between boxes 44050 and 44055 in FIG. 44 (i.e. the steps in boxes 44055 and 44060 need only be done once).

As an alternate, or addition, to extending the second set of labeled-probe-assemblies in the direction opposite from the first set, applicable in cases where box 44060 is included in the repetition cycle, is to remove or deactivate the stain in the first set of labeled-probe-assemblies. This can be done by bleaching the stain (chemically or UV), removing the stain (thermal or pH denaturing and washing), consuming the labeling proteins (protein kinase or chemical degradation), and/or removing any labeled-probe-assemblies on the substrate prior to adding new labeled-probe-assemblies.

Further Alternate Labeled-Probe-Assemblies and Information Encoding Protocols

In one embodiment of this invention, the general layout of the labeled-probe-assembly is as illustrated in FIG. 18. FIG. 18 illustrates the labeled-probe-assembly 1800 consisting of the label-assembly 1840 joined at the ends to linkers, the probe, and functional substrate binding groups. The labeled-probe-assembly 1800 is usually constructed of ssDNA and dsDNA. Starting from the left side of FIG. 18 is shown the probe-end substrate-binding functional-group 1802 and substrate-binding functional-group linker 1804, ssDNA probe 1810, probe-to-label linker 1812, and label-assembly 1840. Continuing in FIG. 18, the label-assembly 1840 is the information encoded region, and includes the start indicator 1820, separate information encoded structures 1830-1833, spacer regions 1824, and end indicator 1822. To the right of label-assembly 1840 are far-end substrate-binding functional-group 1806 and far-end substrate-binding functional-group linker 1808. This labeled-probe-assembly 1800 can also be ligated to the target ssDNA at the functional end group 1850, either a 3'-OH or 5'-P depending on the orientation of the probe ssDNA.

For the embodiment illustrated in FIG. 18, the information is encoded in the length of stained regions of dsDNA, and the stained regions are separated by unstained spacers of dsDNA, all of approximately the same length. For one embodiment, each "A" base is encoded as a 0.5 micron length of stained dsDNA (region 1830 is an example (A)), each "T" base is encoded as a 1.0 um length of stained dsDNA (region 1831 is an example (T)), each "C" base is encoded as a 1.5 um length of stained dsDNA (region 1832 is an example (C)), and each "G" base is encoded as a 2 um length of stained dsDNA (region 1833 is an example (G)). Unstained dsDNA spacers 1824 are each 0.5 um in length. The start indicator 1820 is 0.5 um of stained dsDNA followed by two lengths of unstained dsDNA spacer 1824, and end indicator 1822 is 2 um of stained dsDNA located adjacent to the last encoded base without an intervening spacer. The lengths listed are approximate and some variation along a label-assembly is acceptable.

Alternate embodiments include label-assemblies with the lengths of the base encoding regions and spacers scaled. All the lengths may be scaled over a range of approximately 0.2 to 5 or longer for optical readout. For example, if a scale factor of 0.5 is used, then "A" and spacer would be 0.25 um in length and "G" would be 1 um in length, etc. The main limits to scaling the lengths down is the limits of resolution of the particular readout hardware used. The order and identity of the encoded information must be discernable. When optical microscopy based readout hardware is used, this is determined by the spatial resolution of the optics and camera of the readout hardware and the excitation and emission spectra of the stain. Scaling up to significantly longer lengths, beyond those needed to ensure acceptable resolution of the encoded information, is generally not desirable, as it increases the probability of label-assembly breakage and can slow hybridization of probe to target. With SEM, TEM, AFM, multi-probe AFM, other SPM technology, or other high resolution readout hardware, lengths of information encoding structures along the label assembly can be scaled down from the micron range to the nanometer range, with a minimum dimension, spacer and "A", in the range of 0.5 nm to 300 nm.

As illustrated in FIG. 18, the start indicator 1820 and end indicator 1822 also convey information. They specify the orientation of the encoded base sequence data. For the embodiment illustrated, the start indicator specifies the 3'-end of the sequence, hence the sequence of bases encoded along label assembly 1840 is 3'-A-T-C-G-5'. In an alternate embodiment, the start indicator specifies the 5'-end. Note, as stated elsewhere in this document, the sequence 3'-A-T-C-G-5' is provided as a convenient example, and in fact, any sequence of any length less than the order of 1000 bases could be encoded between the start indicator 1820 and end indicator 1822, and this is true for all of the types of labeled-probe-assemblies presented.

The base sequence of the ssDNA probe 1810 will correspond to the information encoded along the label-assembly 1840. Two obvious choices for this correspondence are for the probe sequence to either match or be complementary to the base sequence information encoded along label-assembly 1840. Hence, for the choice where there is a one-to-one correspondence, the base sequence of the probe 1810 will be 3'-A-T-C-G-5'. Note that other choices are also valid and useful. For example, the probe 1810 may be longer than four bases in length but contain the encoded sequence, for example 3'-N-N-A-T-C-G-N-N-5', where, per standard notation, each base N can be chosen from any of A, T, C, and G. In one embodiment, the sequence of the probe 1810 is the complement of the sequence encoded along the label-assembly 1840, and hence in this particular example is 5'-T-A-G-C-3'. Hence, the encoded sequence matches the sequence along the sample DNA molecule where the probe hybridizes.

Note for the encoding protocol used in FIG. 18, the start indicator and end indicator provide the same information (3' to 5' orientation of encoded bases) and hence only one of these is required. Furthermore, depending on the labeling process used, some of the other components shown in FIG. 18 may not be required. In alternate embodiments some or all of the components 1802, 1804, 1812, 1808, 1806, 1820, 1822, and 1850 may be absent or may exist in multiple copies. In addition, the order of some of the components can be interchanged, placed in different locations along the assembly, and be present in multiple copies. The key components are the probe 1810 and label assembly 1840.

In an alternate embodiment, the layout of the label assembly is similar to that illustrated in FIG. 18, with the addition of two spacer regions 1824, one before start indicator 1820 and one after end indicator 1822. In this alternate embodiment, all spacer 1824 regions are stained, and all other regions are unstained. Hence the information is encoded in the distance between stained spacers 1824.

FIG. 19 shows the layout of the alternate labeled-probe-assembly 1900 that has similar probes 1910 and 1911 on both ends of the assembly. In this alternate embodiment, the labeled-probe-assembly 1900 is designed to hybridize to ssDNA target and both probes, 1910 and 1911, are ssDNA with identical base sequences. The labeled-probe-assembly 1900 is constructed of dsDNA with overhanging ssDNA ends that make-up the probes 1910 and 1911. Each of the non-overhanging strand-ends terminate with the functional end group 1950 and 1951, which is either a 3'-OH or 5'-P, depending on the orientation of the probe. In one embodiment, functional end-groups 1910 and 1911 are exposed 5'-P. Following hybridization of probe to target, the labeled-probe-assembly 1900 can be ligated to the target using the adjacent functional end group, either 1950 or 1951. The probes 1910 and 1911 may be separated from the information encoding label-assembly 1940 by dsDNA probe-to-tag linkers 1912 and 1913.

The information encoding protocol used in the embodiment shown in FIG. 19 uses a start indicator 1920, followed by encoded base data. The start indicator 1920 highlights the orientation of the encoded information, which can be either 3' to 5', or 5' to 3', depending on the choice of the protocol. For one embodiment, the start indicator will indicated the 3' end of the encoded sequence. The base information encoded in the example shown in FIG. 19 is, from left to right in the figure "A" 1930, "T" 1931, "C" 1932, "G" 1933. Hence the probe sequence encoded in FIG. 19 is 3'-A-T-C-G-5'. In this protocol, each "A" 1930 is encoded as a short unstained length of dsDNA 1960 followed by a short stained length of dsDNA 1962, each "T" 1931 is encoded as a short unstained length 1960 followed by a long stained length 1966, each "C" 1932 is encoded as a long unstained length 1968 followed by a short stained length 1962, and each "G" 1933 is encoded as a long unstained length 1968 followed by a long stained length 1966.

The relative dimensions of stained start indicator 1920 and the short and long stained sections (1962 and 1966) must be such that they can be differentiated by the data readout hardware. Also, the relative lengths of the short and long unstained sections (1960 and 1968) must be such that they can be differentiated by the data readout hardware, when each length is bounded by stained sections. In one embodiment, all of the short sections, stained and unstained, are approximately the same length, and all of the long sections, stained and unstained, are approximately the same length and approximately twice the length of the short sections. The start indicator 1920 is approximately three times the length of any of the short stained sections 1960. Furthermore the average length of the short sections are in the range of 0.1 um to 5 um, beneficially in the range of 0.25 um to 3 um, and preferably in the range of 0.5 to 1.0 um in length. For a given average length of short section, the variation between short sections within a label assembly is usually less than 25% of the average length, and typically less than 5% of the average length. These percentages also apply to the variation in the length of long sections within the label assembly.

The embodiment detailed in FIG. 19 has several benefits over that shown in FIG. 18. First, the information encoding protocol is typically more space efficient, more bits per length. Second, with two probes and reduced total length for a given amount of information, the embodiment of FIG. 19 will have the higher interaction rate with target molecules (higher target-probe hybridization rate in the case of ssDNA target and probe). Note in both FIGS. 18 and 19, the density of stain is not exploited as an information encoding parameter, and for the protocols detailed, an approximately constant density of stain is preferred. Encoding of information in variations in density of stain is also presented in this document.

Labeled Multi-Probe Assembly

FIG. 20 shows an alternate labeled multi-probe assembly 2000. Each of the probes 2002 will typically be identical and be connected to the rest of the assembly by its own long linker 2004. One or both ends of the label-assembly 2040 may be capped with multi-probe assemblies. The long linkers 2004 can be dsDNA or another long chain polymer, such as ssDNA, dsPNA, ssPNA, dsRNA, ssRNA, DNA-RNA heteroduplexes, polyethyleneoxide (PEO), polyethyleneglycol (PEG), Microtubule (Tubulin dimer), Actin filament, and fibrous proteins such as proteins of the keratin family, and Cilia and Flagella structures. By incorporating multiple probes, the effective concentration of probe is increased for a fixed concentration of label assembly, and hence the probe-to-target binding rate is increased. The process benefits include reduced numbers of label-assemblies required and reduced reaction times relative to single and double probe labeled-probe-assemblies. The probe assemblies shown in FIG. 20 can be coupled to any of the label-assemblies described or implied by this document.

Another alternate information encoding protocol uses distinguishable differences in stain density to more efficiently pack data. FIG. 21 shows an example label-assembly 2140, which can be combined with any of the probe assemblies described or implied to form the labeled-probe-assembly. For example, label-assembly 2140 can be substituted for label-assembly 1840 or 1940 in FIGS. 18 and 19, respectively. As depicted in FIG. 21, label-assembly 2140 includes a start indicator 2120 that is followed by base encoding regions 2130, 2131, 2132, and 2133. The base encoding regions are all of approximately the same length, and each region contains a single base identity datum encoded in the density of stain in that region. The base sequence encoded in FIG. 21 is 3'-A-T-C-G-5'. In this embodiment each encoded "A" is represented by a length of dsDNA stained at the 100% level, each "T" is represented by a similar length of dsDNA stained at the 75% level, each "C" is represented by a similar length of dsDNA stained at the 50% level, and each "G" is represented by a similar length of dsDNA stained at the 25% level. Hence in FIG. 21, section 2130 has the highest density of stain, section 2131 has 75% of the density of stain as section 2130, section 2132 has 50% of the density of stain as section 2130, and section 2133 has 25% of the density of stain as section 2130, and all these sections are of approximately equal length. In FIG. 21, the density of stain is illustrated by the height of the box shown in each region. The percentages listed are relative to the maximum stain density employed and are approximate numbers. The main factor used to derive specific percentages for a given type of stain is that the four levels of staining must be mutually distinguishable by the label readout hardware and data analysis algorithm. Recommended densities for several commonly used stains are presented below.

The start indicator 2120 specifies the 3'-end of the encoded sequence of bases. To minimize the length of the start indicator 2120, the following cyclic algorithm can be used to select the correct density of stain for the start indicator 2120. If the last encoded base is T, then the density of stain used in the start indicator 2120 is the same as for "A", 100%. If the last encoded base is C, then the density of stain used in the start indicator 2120 is the same as for "T", 75%. If the last encoded base is G, then the density of stain used in the start indicator 2120 is the same as for "C", 50%. And, if the last encoded base is "A", then the density of stain used in the start indicator 2120 is the same as for "G", 25%. For the example shown in FIG. 21, the start indicator 2120 has a density of stain of 50%, same as an encoded "C". Using this algorithm, the length of the start indicator 2120 can be the same as that of the individual base encoding sections, and hence the start indicator 2120 of FIG. 21 is another encoded "C". Note that this start indicator density selection algorithm also provides a means of error detection.

The average length of the individual base encoding sections shown in FIG. 21 is in the range of 0.1 um to 5 um, beneficially in the range of 0.25 um to 3 um, and preferably in the range of 0.5 to 1.0 um in length. For a given average length of section, the variation between sections within a label assembly is usually less than 25% of the average length, and typically less than 5% of the average length. The maximum allowable variation in region length is determined by the possible number of repeated bases that must be resolved.

A variation on the information encoding protocol presented above for FIG. 21 would include unstained lengths of label assembly as one of the base encoding densities of stain (i.e. 0%). An example label assembly 2240 is illustrated in FIG. 22 for the encoded base sequence 3'-A-T-C-G-G-5'. This protocol requires an alternate start indicator 2220 protocol, and the end indicator 2222, while not required, would be beneficial. As an example, a workable protocol using three densities of stain and unstained would use 100% stain density to represent each "A" (region 2230 in FIG. 22), 67% stain density to represent each "T" (region 2231), 33% stain density to represent each "C" (region 2232), and unstained (0% stain density) to represent each "G" (regions 2233 and 2234). An efficient choice of density of stain for the start indicator and end indicator density is 100% for the start indicator 2220 and 33% for the end indicator 2222. In this embodiment, the start indicator specifies the 3'-end. Lengths, and variation in lengths, of the individual regions would be as stated above for FIG. 21. It is evident in FIG. 22 that the variation in length must be limited in order to resolve the two adjacent unstained regions 2233 and 2234.

A further variation of the protocols detailed in FIGS. 21 and 22, that has the benefit that the length of the individual base encoding regions can vary greatly without affecting the ability to resolve runs of repeated bases, is illustrated in FIG. 23 which shows example label-assembly 2340. This protocol uses five distinguishable densities of stain, for example 100%, 75%, 50%, 25% and 0%. The protocol progresses from the first base encoding datum, region 2330, through each consecutive datum until the end indicator 2322. For the first datum, the base encoding assignments are 100%="A", 75%="T", 50%="C", and 25%="G". Note that with the first base encoding assignments, 0% can not be assigned. For each consecutive datum, the density of stain for the last base encoded is changed to the density of stain that was not assigned. Hence for the second datum, the previously unassigned stain density, 0%, is substituted for the density of stain of whichever base was the first datum. In the example of FIG. 23, the encoded sequence is 3'-A-T-C-G-G-5', hence for the second datum, the base assignments are 0%="A", 75%="T", 50%="C", and 25%="G", with 100% not assigned. This cyclic replacement algorithm is applied anew for each subsequent base-encoding region. Hence for the third datum in this example, the base assignments are 0%="A", 100%="T", 50%="C", and 25%="G", with 75% not assigned. For the fourth datum in this example, the base assignments are 0%="A", 100%="T", 75%="C", and 25%="G". Finally, for the fifth datum in this example, the base assignments are 0%="A", 100%="T", 75%="C", and 50%="G". The density of stain along the base encoding regions of FIG. 23 is then 100% (region 2330)-75% (region 2331)-50% (region 2332)-25% (region 2333)-50% (region 2334). Using this protocol, no adjacent base encoding regions can have the same density of stain, and hence length need not be accurately resolved.

For the protocol detailed above and illustrated in FIG. 23, the start indicator is not required, as 0% density of stain can not be assigned to the first base encoding region 2330. Selection of density of stain for end indicator 2322 can be based on a cyclic permutation of the first base encoding region 2330. Hence, if the first base encoding region uses a 100% density of stain, then the density of stain for end indicator 2322 would be 75%. The complete region 2330 to region 2322 correspondence is (2330:2322) 100%:75%, 75%:50%, 50%:25%, and 25%:100%. This end indicator density of stain algorithm provides a redundant check on the identity of the first base as well as the directional orientation information for the label data. The length of the end indicator 2322 is typically approximately the same as the lengths of the individual base encoding regions.

In FIGS. 20, 21, 22, and 23, information is encoded in distinguishable differences in the density of a single stain type or fixed mixture of stains. Differences in density of stain result in differences in emission intensity that can be resolved by the readout hardware and software. In addition to varying density of stain, similar information encoding protocols and algorithms can be applied using distinguishably different types of stain. Typically, between different types of stain, there are distinguishable differences in their excitation and/or emission spectra. Of course, the readout hardware and software must be equipped to distinguish between the various excitation and/or emission spectra. In alternate label assembly embodiments, the four densities of stain discussed for FIGS. 20, 21, and 22, can be replaced by four different stain types, each with a distinguishably different excitation and/or emission spectra. For example, base sequence information can be encoded along the label assembly using stain type 1 to represent "A", stain type 2 to represent "T", stain type 3 to represent "C", and stain type 4 to represent "G". Alternately, stain Type-1 can be used to represent encoded "A" bases, the mixture of stain Type-1 and Type-2 to represent "T", the mixture of stain Type-1, Type-2, and Type-3 to represent "C", and the mixture of all four stain types, Type-1, Type-2, Type-3, and Type-4, to represent "G".

In one embodiment, four intercalating dimeric cyanine nucleic acid stains from Invitrogen Molecular Probes, YOYO-1, POPO-1, TOTO-1, and JOJO-1 are used. The general layout of the labeled-probe-assembly could be similar to that of FIG. 21. In this case, the entire length of each base-encoding region can be stained by one of these stain types. In this embodiment each encoded "A" is represented by a length of dsDNA stained with YOYO-1, each "T" is represented by a similar length of dsDNA stained with POPO-1, each "C" is represented by a similar length of dsDNA stained with TOTO-1, and each "G" is represented by a similar length of dsDNA stained with JOJO-1. Hence in FIG. 21, section 2130 has the highest density of stain, section 2131 has 75% of the density of stain as section 2130, section 2132 has 50% of the density of stain as section 2130, and section 2133 has 25% of the density of stain as section 2130, and all these sections are of approximately equal length. The encoded sequence of bases shown in FIG. 21 is 3'-A-T-C-G-5'. Hence, reinterpreting FIG. 21 for this four stain algorithm, the first base encoding region 2130 would by stained with YOYO-1, the second base encoding region 2131 would be stained with POPO-1, the third base encoding region would be stained with TOTO-1, and the forth base encoding region would be stained with JOJO-1. Applying the start indicator staining protocol previously described for FIG. 21, but substituting the four different stains for the four stain densities, the start indicator 2120 would be stained as an "C" with TOTO-1. In this embodiment the start indicator 2120 specifies the 3'-end of the encoded sequence. Each of the individual stained regions will typically have a length in the range of 0.1 um to 10.0 um, and more typically in the range of 0.25 um to 2.0 um. Note that to improve the ability to resolve the order and stain type of adjacent stained regions, unstained or counter stained spacers can be located between stained regions. Use of spacers, typically dsDNA 0.15 um to 2.0 um in length, is particularly beneficial when shorter stained regions are employed. Use of spacers could be applied to any of the label assembly embodiments.

Five types of stain could be used with the protocol discussed with FIG. 23. Different types of stain could also be mixed to form emission spectra distinguishably difference from those of the individual stain components. For example, four distinguishable stain combinations can be made using two pure stain types, a mixture of these two pure types, and unstained dsDNA. With three distinguishable pure stain types, at least seven distinguishable stains should be realizable; the three pure types plus the three pair-wise combinations plus the mixture of all three. Furthermore, variations in density of stain, of both pure stains and mixtures of stains, and distinguishable shades of mixtures, for example two-stain mixture ratios of 1:1, 2:1, 1:2, 1:3, etc., as well as unstained regions, can be used to encode information. In one embodiment, four distinguishable shades of stain are derived from the two stains YOYO-1 and POPO-3 such that each base "A" is represented by pure YOYO-1, each base "T" is represented by pure POPO-3, each base "C" is represented by the 2:1 mixture, (2 parts YOYO-1 and one part POPO-3), and each base "G" is represented by the 1:2 mixture of YOYO-1 and POPO-3.

For certain methods of generating the stained label-assemblies, the following four stain-type staining protocol has certain benefits. "A" bases are encoded as label-assembly regions stained with Type-1 stain, "T" bases are encoded with a mixture of Type-1 and Type-2 stains, "C" bases are encoded with a mixture of Type-1, Type-2, and Type-3 stains, and "G" bases are encoded with a mixture of all four stain types, Type-1, Type-2, Type-3, and Type-4. This staining protocol can be applied to many of the information encoding protocols presented. In particular, the information encoding protocol discussed in relation to FIG. 21 is compatible with this staining protocol. In one embodiment of this staining protocol, the Type-1 stain is YOYO-1, Type-2 stain is POPO-1, Type-3 stain is TOTO-1, and Type-4 stain is JOJO-1. Reinterpreting FIG. 21, with start indicator 2120 a "C" and encoded sequence 3'-A-T-C-G-5', with this staining protocol, region 2130 would be stained with YOYO-1, region 2131 stained with YOYO-1 and POPO-1, region 2132 stained with YOYO-1, POPO-1, and TOTO-1, region 2133 stained with YOYO-1, POPO-1, TOTO-1, and JOJO-1, and region 2120 would be stained as for "C" with YOYO-1, POPO-1, and TOTO-1. The optimum density of stain for each type of stain within the mixtures depends on the performance of each stain and the responsiveness of the readout hardware to each stain. Typically, approximately equal densities of each type of stain are used.

Using mixtures of stains and variations in stain density, wherein each successive mixture starts with the previous mixture and adds one previously unused stain type or a dilution, has certain manufacturing benefits that are described in the section on the staining of labeled-probe-assemblies, below, in "Controlled strand-separation staining method" and using related methods based on duplex stability. The single stain type and successive density of stain protocols illustrated in FIGS. 18-23 fit this method, as does the four-stain protocol detailed in the paragraph above. A similar five stain type protocol can utilize the following five distinguishable stain mixtures, Type-1, Type-1 mixed with Type-2, the mixture of types 1-3, the mixture of types 1-4, and the mixture of all five types, types 1-5. Alternately, mixtures of two, three, or four stains can be used to generate five distinguishable shades while adhering to the successive mixture method detailed in this paragraph. Alternately, the various stains can be applied as different secondary labeled probes as presented in the detailed description of FIG. 43.

Label-Assemblies with Cleavable-Linkers and Substrate Elongation Along the Direction of Extension of the Label-Assemblies In an alternate embodiment, the labeled-probe-assembly includes individual base encoding regions that are separated by cleavable linkers and each region may have a cross-linker binding group. The cleavable linkers allow the label assembly to be controllably broken into its constituent components, typically each containing one single bit of information, and the cross-linker binding groups allow each of these components to be affixed to the substrate. Such a labeled-probe-assembly with cleavable linkers is illustrated in FIG. 24. As shown in FIG. 24, the labeled-probe-assembly 2400 consists of at least the probe 2410 and label assembly 2440. The label assembly 2440 consists of at least one or more cleavable regions (2420 and 2430-2434 in the example illustrated in FIG. 24), each of which include typically one bit of encoded information (2430-2434), one or more functional groups 2480 that can form part of a cross-link between the cleavable region and substrate, and cleavable linkers 2460 typically between each cleavable region. Deformable substrates are generally used when cleavable linker labeled-probe-assemblies are used.

In use, the labeled-probe-assembly binds to a target molecule that is on a substrate. The target-bound labeled-probe-assembly is extended over the substrate and affixed to the substrate through the cross-linker binding groups. Cleavable linkers along the labeled-probe-assembly are then cleaved, and the substrate is stretched, flowed, expanded, and otherwise elongated, with a component of the elongation in the same direction in which the label assembly had been extended. As a result of this substrate elongation, the individual cleavable regions are spatially separated such that their order and identity can be resolved by the readout hardware. Two benefits of labeled-probe-assemblies with cleavable linkers and the spatial separation process are that the label assembly can be much shorter and, consequently, the probe-to-target reaction rate can be higher. FIG. 51 details the basic process flow for using labeled-probe-assemblies with cleavable linkers.

FIG. 24 illustrates a labeled-probe-assembly with cleavable linkers 2400. The embodiment in FIG. 24 uses four distinguishable dye types in a one-to-one correspondence to represent the four nucleotide bases, type 1 represents "A", type 2 represents "T", type 3 represents "C", and type 4 represents "G". As illustrated in FIG. 24, the labeled-probe-assembly 2400 is constructed of dsDNA with overhanging ssDNA ends, which are the probes 2410 and 2411. Each of the non-overhanging, recessed, strand ends terminate with the functional end group 2450 and 2451, which is either a 3'-OH or 5'-P, depending on the orientation of the probe. In one embodiment, functional end groups 2450 and 2451 are exposed 5'-P. Following hybridization of probe to target, the labeled-probe-assembly can be ligated to the target using the adjacent functional end group, either 2450 or 2451. In another embodiment, there is no ligation step. The probes 2410 and 2411 may be separated from the information encoding label-assembly 2440 by dsDNA probe-to-tag linkers 2412 and 2413.

The information encoding protocol used in the embodiment shown in FIG. 24 uses a start indicator 2420, followed by encoded base data. The start indicator 2420 highlights the orientation of the encoded information, which can be either 3' to 5', or 5' to 3', depending on the specifics of the protocol. For one embodiment, the start indicator will indicate the 3' end of the probe sequence. The base information encoded in the example shown in FIG. 24 is, from left to right in the figure "A" 2430, "T" 2431, "C" 2432, "G" 2433. Hence the probe sequence encoded in FIG. 24 is 3'-A-T-C-G-5'. For this sequence, region 2430 includes the type 1 dye, region 2431 includes the type 2 dye, region 2432 includes the type 3 dye, and region 2433 includes the type 4 dye. The stain type for the start indicator 2420 can be determined using the cyclic protocol described for FIG. 21, and hence stain type 3 is used for the sequence ending in "G".

Referring to FIG. 24, between each of the regions that must be spatially resolved (2420, 2430, 2431, 2432, 2433) there is a cleavable linker 2460, in one embodiment dsDNA that includes a restriction enzyme recognition site. Included in each information-encoding region is one or more cross-linker binding group 2480. In one embodiment, the nicking enzyme recognition sequences 2470 are associated with each cross-linker binding group 2480. Each of these nicking enzyme recognition sequences 2470 facilitate the formation of one cross-linker binding group 2480 by targeting the nicking enzyme to cut one strand and expose a 5'-P end group which is used as an intermediary in cross-linking the information encoded structure to the substrate. The cross-linking process detailed in Chu, B. C. F., Wahl, G. M., Orgel, L. E., Nucleic Acid Research (11)18: 6513 6529 (1983) and similar chemistries in "Covalent Binding of DNA to CovaLink NH Methods and Applications", Bulletin No. 10(1), (1997), NUNC Brand Products, Nalge Nunc International, and modification of 5'-P to a reactive sulfur group with the 5' EndTag Nucleic Acid Labeling System by Vector Laboratories can be used to cross-link the cross-linker binding groups 2480 to available amine-groups on the substrate.

In alternate embodiments, other cross-linker binding groups 2480 may be employed, such as branched backbone structures with the branches terminating on reactive functional end groups (—N—H2, —P—O3-H, —C═O, —S—H2, sulfhydryl, thiol, phosphoryl, phosphonate, amine, carboxyl, hydroxyl, etc.). Alternately, non-specific binding to the substrate may be used. Further alternate embodiments use random cross-linking at multiple locations between extended label assembly and substrate. This random cross-linking can include non-specific DNA-to-substrate binding and nicking, by any means such as UV, enzymatic, and chemical degradation, of the DNA followed by cross-linking between the nicks and substrate.

Alternately, the cross-linker binding groups 2480 may be dsDNA of specific sequence, which is the target sequence for a sequence specific dsDNA binding protein. In use, the "cross-link to substrate" process steps become: introduce protein molecules and allow to bind at the recognition sites, wash away non-specifically bound and excess protein, and cross-link the DNA-bound proteins to the substrate with a suitable protein-to-substrate cross-linker type and protocol.

Cleavable linkers can include unmodified dsDNA, cleaved by mechanical stress as the substrate is elongated.

It is important to note that the general method of including cleavable linkers and cross-linker binding groups and the process of spatially separating the individual base encoding regions by stretching, flowing, expanding, and otherwise elongating the substrate can be applied to any of the information encoding algorithms and protocols detailed in, and following from, this document. The method can also be applied to label-assemblies fabricated with backbones other than dsDNA, such as ssDNA, dsPNA, ssPNA, dsRNA, ssRNA, DNA-RNA heteroduplexes, polyethyleneoxide (PEO), polyethylene glycol (PEG), polyvinyl alcohol (PVOH), polyethylene (PE), polypropylene (PP), polystyrene (PS), other synthetic polymers, Microtubule (Tubulin dimer), Actin filament, and fibrous proteins such as proteins of the keratin family, and Cilia and Flagella structures. Backbones may be linear or branched, and may include cleavable linkages along the backbone such as disulfide groups (cleavable by mild reduction), ethylene glycol linkages (cleavable by hydroxylamine), and restriction enzyme recognition and cutting sites on dsDNA (cleavable by action of restriction enzymes using any standard protocol).

Alternate embodiments of labeled-probe-assemblies with cleavable linkers can employ any of the information encoding protocols presented and implied by this document. Furthermore, alternate embodiments can employ any of the probes and probe assemblies presented and implied by this document.

Labeled-Probe-Assemblies Fabricated of DNA and Containing Recognition and Binding Sequences for Sequence-Specific DNA-Binding Proteins and Sequence-Specific DNA-Binding Proteins Protein Labeling of Labeled-Probe-Assemblies as a Staining Method, as a Substrate Binding Method, and as a Means of Attaching a Protein Probe As presented above, the interaction between sequence specific DNA-binding proteins and label-assemblies fabricated with DNA containing the specific binding sequence can be used to facilitate label assembly-to-substrate binding. There are many other beneficial uses, and three additional general classes of use standout. First, the label-assembly bound protein can function as a probe or probe-to-label-assembly linker. Second, label-assembly bound proteins can be stained or otherwise labeled so as to facilitate readout of the information encoded along the label assembly. Third, proteins with beneficial enzymatic activity can be used to generate signals and hence display the information encoded along the label assembly or affect a change in the environment near the target. Note that for certain applications, DNA-binding proteins that do not have sequence specificity can be used, and proteins can be cross-linked to the DNA to covalently bond them together.

The labeled-probe-assembly illustrated in FIG. 25 illustrates one use of sequence-specific DNA-binding proteins for tagging, decorating, or labeling the label-assembly. In this application, the labeled-probe-assembly has a DNA backbone, and the information is encoded as specific base sequences located at specific, predetermined, locations or in defined concentrations along regions of the label assembly. These specific base sequences are by design the recognition sequences and binding site sequences, target sequences, of the sequence-specific DNA-binding proteins to be used for tagging the label-assembly.

FIG. 25 illustrates the labeled-probe-assembly 2500 fabricated of dsDNA that includes regions of dsDNA 2590 of specific sequence that is the target sequence for sequence-specific dsDNA binding proteins. The label assembly 2540 includes information encoded structures 2530, 2531, 2532, and 2533, and start indicator region 2520. The information encoding protocol illustrated in FIG. 25 is the same as that detailed for FIG. 21, except that, instead of varying the density of stain, it is the number of repeats, or concentration, of specific dsDNA sequence 2590 per length that is varied. Note, for clarity in FIG. 25, not all sequence regions 2590 are labeled. All regions 2590 are illustrated by two short vertical lines that illustrate the ends of each sequence region 2590.

In this paragraph, region 2530 of FIG. 25 is described in detail as an example of any of the information encoded structures. The concentration of regions 2590 is approximately constant along region 2530. In this particular case, there are bases separating each of the regions 2590, and the sequences of the bases between regions 2590 do not themselves constitute protein binding target sequences. The only protein binding target sequences are the regions 2590. Adjacent regions 2590 should be separated by sufficient bases such that protein binding is not sterically or electrostatically hindered. Typically, regions 2590 should be separated by a minimum of 5 to 50 bases, and the minimum number of separating bases is dependent on the type of proteins to be employed. The layout of the other information encoded structures, 2520, 2531-2534, is similar to that illustrated for region 2530, with approximately constant concentration of regions 2590 within each encoding region but varying from encoding region to encoding region, and with suitable spacing between regions 2590 for each encoding region.

In one embodiment the following base information encoding protocol is employed, each "A" is represented by a region with the maximum number of repeats of sequence 2590, each "T" is represented by a region with 75% the number of repeats of sequence 2590 as for an "A", each "C" is represented by a region with 50% the number of repeats of sequence 2590 as for an "A", and each "G" is represented by a region with 25% the number of repeats of sequence 2590 as for an "A". The number of sequence 2590 repeats in the start indicator 2520 is determined by the same algorithm as detailed for FIG. 21. In one embodiment, the maximum number of repeats of sequence 2590 is such that approximately 33% of all dsDNA within the region is repeats of sequence 2590. Hence the absolute percentage of dsDNA within each base encoding region that is repeats of sequence 2590 is approximately 33% for an encoded "A", approximately 24.75% for an encoded "T", approximately 16.5% for an encoded "C", and approximately 8.25% for an encoded "G". This encoding algorithm is illustrated in FIG. 25 which shows the encoding for the base sequence 3'-A-T-C-G-5' and start indicator "C" indicating the 3'-end. Hence, approximately 16.5% of start indicator 2520 is compose of specific sequence regions 2590, approximately 33% of the first base encoding region 2530 is composed of regions 2590, approximately 24.75% of the second base encoding region 2531 is composed of regions 2590, approximately 16.5% of the third base encoding region 2532 is composed of regions 2590, and approximately 8.25% of the forth base encoding region 2533 is composed of regions 2590. The total length of each of these regions is approximately equal and is determined by the spatial resolution capabilities of the readout hardware. Typically, for optical microscope based readout hardware, the length of each of the information encoded structures 2520 and 2530 through 2533 is in the range of 0.15 um to 10.0 um, and preferably in the range of 0.25 um to 2.0 um. For readout hardware based on SEM, TEM, AFM, other types of SPM (Scanning Probe Microscope) or other high resolution imaging methodology, the lengths of regions 2520, 2530-2533 can be in the range of approximately 5 nm and longer, and preferably in the range of 20 nm to 300 um. Independent of the magnitude of the length, the variation in length between information encoded structures of a particular label-assembly is less than 20% and preferentially less than 5%.

Detailed description of process flow: The process for using the labeled-probe-assembly depicted in FIG. 25 includes binding the probe to its target, washing away excess labeled-probe-assemblies, extending the remaining labeled-probe-assemblies over the substrate, immersing the substrate in a solution containing the sequence specific dsDNA binding proteins and binding the proteins according to their recognition sequences, washing away excess protein, staining the remaining protein, and visualizing and reading out the density of stained protein on the substrate. Finally, the readout data are analyzed to determine the identity of the target. This baseline process can be modified to include elongating the substrate in one or two directions to spatially separate the proteins as a means to overcome limits of resolution imposed by the data readout apparatus.

Note that the term "staining" here means to render readable by the readout hardware, and, depending on the type of readout hardware, may include treatment with a general protein stain, fluorescent protein stain, colloidal gold, staining fixative such as osmium tetroxide, use of radio-isotope labeled proteins, treatment with labeled anti-bodies to the protein used, and where the protein used has suitable enzymatic activity, treatment with the target substrate for the enzyme and readout of the reaction products or loss of target substrate. Alternately, exposed dsDNA along the labeled-probe assembly may be stained instead of, or in addition to, the proteins, by making use of the footprint of the DNA bound proteins to inhibit staining of those regions of the DNA. By this method, regions along the labeled-probe assemblies with the highest concentration of DNA bound protein will receive the lowest average density of DNA stain and will appear darker to the readout hardware.

Finally, note that other process flows would now be evident to skilled practitioners in the field. These alternate processes would include, but not be limited to, variations in the protocols presented, including rearrangement in the order of the process steps. For instance, proteins can be stained prior to their interaction with the labeled-probe-assemblies; proteins can be bound to the labeled-probe-assemblies prior to the binding of the probes to targets, etc.

A similar methodology can be applied to protocols employing multiple types of sequence specific dsDNA binding proteins, where each type of protein has a unique recognition sequence. Depending of the number of different types of protein used, all of the previously described information encoding protocols presented and implied can be adapted for use with stained proteins. This is accomplished by substituting for the staining of the DNA backbone of the label assembly, the insertion of DNA binding protein recognition sequences at specific locations or specified concentrations varying along the DNA backbone. Each different type of protein used can be labeled with a unique, distinguishable, stain prior to use in binding to the DNA label-assembly, and in this way each type of protein functions as a different type of DNA stain.

For example, protein type-1, with unique target recognition sequence 1, is substituted for stain type-1, protein type-2, with unique target recognition sequence 2, is substituted for stain type-2, and so on for Type-3, etc. Information protocols described above that use differing densities of stain can be implemented by varying the density or concentration, number per unit length of label-assembly, of specific recognition sequences. Protocols that call for different types of stain or mixtures of different types of stains can be implemented by fabricating the label assembly with multiple different, unique, recognition sequences and patterns of alternating recognition sequences.

Sequence specific DNA binding proteins can also be beneficially applied to cleavable label-assemblies. FIG. 26 illustrates the labeled-probe-assembly 2600 with label assembly 2640 that uses, in this illustration, the four color protocol detailed for FIG. 21 and including the start indicator algorithm. For this illustration, label assembly 2640 encodes the base sequence 3'-A-T-C-G-5'. Hence there are four types of sequence specific DNA binding proteins required, each with a unique target recognition sequence, protein type 1 binds to recognition sequence 2691, type 2 binds to recognition sequence 2692, type 3 binds to recognition sequence 2693, and protein type 4 binds to recognition sequence 2694. Note that some suitable proteins do not bind directly to their target recognition sequence but nearby binding is triggered by proximity to the recognition sequence. For this protocol, the encoded base-to-targeted protein correspondence is "A"=type-1, "T"=type-2, "C"=type-3, and "G"=type-4. ssDNA hybridization probe 2610 and probe-to-label linker 2612 are connected to the label assembly 2640. Label assembly 2640 includes start indicator region 2620 which includes recognition sequence 2693 (By the start indicator selection algorithm described for FIG. 21, start indicator region 2620 is encoded as for a "C", which is represented by the type-3 protein target sequence). The first base encoding region 2630 includes recognition sequence 2691, second base encoding region 2631 includes recognition sequence 2692, third base encoding region 2632 includes recognition sequence 2693, and forth base encoding region 2633 includes recognition sequence 2694. Hence, each base-encoding region can bind only one protein. The distance between adjacent protein binding sequences is made approximately equal, and the amount of substrate elongation required to resolve the individual proteins during data readout varies inversely with the magnitude of the as-fabricated distance between adjacent protein binding sequences.

Note that in other embodiments, each base-encoding region may include multiple copies, from two to thousands of copies, of the appropriate recognition sequence. Data analysis is simplified if the number of copies in each base-encoding region is approximately equal. Including multiple copies increases signal strength during data readout, adds redundancy to the information, can allow shorter protein to label-assembly binding times, and can reduce the amount of substrate elongation required to resolve the encoded data, even eliminating the need for substrate elongation altogether. Minimizing the number of copies gives the shortest, most material efficient label-assemblies. Selection of the number of copies of a particular recognition sequence within a base-encoding region is largely determined by the resolution and sensitivity of the readout hardware, quantum efficiency of the stain employed, the dynamics of the protein binding process, and the equilibrium constant pKa of the protein-DNA system.

Detailed description of process flow for use with labeled-probe-assemblies such as that illustrated in FIG. 26: In a further alternate embodiment, the DNA bound proteins serve three functions, stained bodies visible to the readout hardware, substrate cross-linker binding groups, and they define the cleavable links. The general process includes: 1) binding the probe to its target, 2) washing away excess labeled-probe-assembly, 3) extending the remaining labeled-probe-assemblies over the substrate and fixing to the substrate, 4) immersing the substrate in a solution containing the four types of sequence specific dsDNA binding proteins (where individual types have been pre-stained with distinguishable stain types) and binding the proteins according to their recognition sequences, 5) washing away excess protein, 6) cross-linking the remaining (labeled-probe-assembly-bound) proteins to the substrate, 7) consuming or degrading (cleaving) the exposed DNA (exposed labeled-probe-assembly backbone) or releasing the DNA from the proteins or doing nothing and allowing the DNA to break as the substrate is elongated, 8) elongating the substrate so as to spatially separate the proteins so that their order and type can be resolved, and 9) visualizing and reading out the identity and location of the stained proteins. Finally, the readout data are analyzed to determine the information encoded along the label assembly, such as the identity, base sequence, of the target.

Additional Alternate Labeled-Probe-Assemblies and Information Encoding Protocols In this invention, information can be encoded in both indicating and non-indicating tag regions. Indicating regions are those tag regions that can be differentiated from the background by means of attached or incorporated labels, such as dye molecules, stains, fluorescent labels, counter stains, radioisotope labels, functional enzyme labels, substrate-specific functional labels, metal cluster labels, stained sequence-specific DNA-binding proteins, and other labels. The means of visualizing or otherwise detecting the label is dependent on the specific labeling methodology associated with the specific label. For example detection of fluorescent label molecules can be accomplished by excitation of the molecules with a specific frequency range of light and detection of the fluorescent emission over another, non-overlapping, range of frequencies. More specifically, the techniques of fluorescent spectroscopy and time-resolved fluorescent spectroscopy can be applied to substrate scanning tag detection schemes. Alternately, substrate-specific functional labels, such as ssDNA or ssPNA of a specified base sequence, can be coupled with ssDNA or ssPNA substrate of complementary base sequence and which is itself labeled for subsequent detection by the same or alternate means. Another substrate-specific functional label is biotin connected by a linker along the label-assembly, and which can be detected by binding with tagged avidin or streptavidin as in ELISA methods.

In one embodiment, the non-indicating label-assembly regions are formed of unstained dsDNA and alternately unstained and strand-to-strand cross-linked dsDNA, and the indicating tag regions are formed of fluorescent stained dsDNA, such as dsDNA with intercalated dicyanic fluorescent stain. Appropriate dyes include YOYO-1 and other dicyanic dyes marketed by Invitrogen (formerly by Molecular Probes Inc.). Alternately, the dsDNA employed in the non-indicating and indicating tag regions can be strand-to-strand cross-linked to render it resistant to melting and strand displacement. Additionally, this dsDNA can be methylated or otherwise modified to render it more resistant to cleavage. Furthermore, the dsDNA can be substituted with molecules with sulfur containing backbones for resistance to cleavage. Alternately, long-chain polymers, other than dsDNA, can be employed, such as ssDNA, dsPNA, ssPNA, dsRNA, ssRNA, DNA-RNA heteroduplexes, polyethyleneoxide (PEO) with attached dye molecules, stained Microtubule (Tubulin dimer), stained Actin filament, and stained fibrous proteins such as proteins of the keratin family, and stained Cilia and Flagella structures.

Indicating label-assembly regions can be labeled with different pure dyes at various base per dye molecule loading, and mixtures of pure dyes in various proportions and at various bases per dye molecule loading, in other words, information can be encoded as color and intensity. In this way, information can be encoded into the indicating label-assembly regions as emission intensity versus excitation frequency, emission frequency or frequencies and relative intensity of emission lines for a range of excitation frequency, and intensity of emission versus excitation or emission frequency. Information can also be encoded into the length of specific label-assembly regions, including the length of non-indicating regions between indicating regions. Given the variables of color, intensity, and length, many information encoding algorithms are available. The following paragraphs detail the practical implementation of several algorithms for encoding base sequence data.

In this algorithm, information is encoded along a long molecule with one type of stain applied at approximately constant density over different length coding "bits" with unstained spacers between bits or incorporated into the bits. The length of the shortest indicating region is set by the minimum detectable signal strength and the signal per unit length. The minimum length of the non-indicating spacers and the length difference between the other bits is set by the spatial resolution of the data readout apparatus. By way of example, a label-assembly for encoding DNA sequence data and fabricated of dsDNA, using YOYO-1 stain at a loading of 20 bases per YOYO-1 molecule and unstained spacers, can be made using 0.5 micron spacers and base-4 "bits" where 0.5 microns of stained dsDNA="A", 1.0 microns="T", 1.5 microns="C", and 2 microns="G". The actual number of base-pairs (bp) that are included in each bit depends and the substrate and method of extending the label-assembly prior to readout, and is typically about 2400 bp per micron. Hence in this example, ~1200 bp of stained dsDNA surrounded by unstained regions and extended straight would be interpreted as an "A". More base sequence information can be encoded into a label-assembly by joining, ligating, together additional base-4 bits separated by unstained spacers. The order of the base information along the label-assembly can be made to match the order of bases in the DNA sequence encoded, and thus the base and ordering information recoverable from the extended, out-stretched, label-assembly is the entire base sequence data set.

A start-bit can be added to an ordered string of data, to indicate the orientation of the base sequence, i.e. by indicating the 3' or 5' end. In this example, a 5 micron length of stained dsDNA can be ligated to the 3' end of the sequence data to indicate the 3' end. Alternately, in cases where base sequences longer than two bases are encoded, a 2 micron spacer can be used between the first and second bits of the 3' end to indicate the 3' end. Of course, alternately, the protocol could be written such that either of these orientation indicators would show the 5' end of the sequence data, and an end-bit indicator could be used instead of, or in addition to a start-bit indicator.

An example of a more compact protocol uses a start-bit, and encodes the four bases as 0.5 micron unstained+0.5 micron stained="A", 0.5 micron unstained+1.0 micron stained="T", 1.0 micron unstained+0.5 micron stained="C", and 1.0 micron unstained+1.0 micron stained="G". (Here "+" can be read as "immediately followed by".) Spacers between bits are not used. A 3 micron length of stained dsDNA can be used as the start-bit to indicate the 3' end, or 5' end, of the sequence data and to indicate the start of the first unstained length. With this protocol, the average 10-mer can be encoded onto 16.5 microns of dsDNA, and the longest 10-mer (10×G) onto 21.5 microns of dsDNA. As in the other examples, the encoding protocol can specify that the ordering of base information along the label-assembly match the sequence of bases along the encoded DNA molecule, and hence, the data recovered from the extended label-assembly are the complete data set for the encoded DNA molecule. The complete data set being; all bases, in the correct order, with 3' end to 5' end orientation specified.

Alternate Probes and Probe Connection to Label-Assembly

The probe shown on most of the labeled-probe-assemblies illustrated in this document are short lengths of ssDNA (single-strand DNA), typically one to 30 bases in length, and are intended for hybridizing to ssDNA and ssRNA targets. Other types of probe with other targets can be readily incorporated into the labeled-probe-assembly by ligating or cross-linking the alternate probe to any of the label-assemblies presented in or derived from this invention. Suitable probe types include:

For sequencing of DNA, RNA, and PNA by hybridization, probes can be N-mers (oligomers of length N) of ssDNA, ssRNA, ssPNA (single-strand peptide-nucleic-acid), or combinations of these.

For sequencing of DNA, RNA, and PNA by hybridization, probes can be oligomers of ssDNA, ssRNA, ssPNA, or combinations of these, designed so that all have approximately equal stringency conditions, as described below.

For recognition of specific DNA, RNA, or heteroduplex RNA-DNA sequences, probe can be protein that will bind to specific single-strand or double-stranded DNA or RNA sequences, or RNA-DNA heteroduplex sequences.

For tagging specific proteins and other molecules, probe can be anti-body to target protein, protein or molecules that will specifically bind to the target protein or molecules (biotin to avidin, biotin to streptavidin, and vise versa, etc.), ss or dsDNA or RNA of specific sequence that is the recognition sequence for the target DNA or RNA binding protein, or ss or dsDNA or RNA of specified minimum length to target non-sequence-specific DNA or RNA binding proteins.

For tagging proteins in a non-specific manor, probe can be protein cross-linking molecule.

For targeting DNA or RNA in a non-specific manor, probe can be DNA or RNA cross-linking molecule or intercalator.

Equal Stringency Hybridization Probes

Sets of hybridization probes, oligomers of ssDNA, ssRNA, ssPNA, and heterostructures of these, can be design so that all members of the set have approximately the same stringency condition. The benefit of this design is that probes with many different sequences, including complete sets of probes, can be efficiently and accurately hybridized at one process temperature. Furthermore, excess probe and incorrectly bound probe can be rinsed away using a single stringency rinse process. The key is to construct the probes such that the melting temperatures for all the various probe sequences within the set of probes are approximately equal.

The melting temperature for short DNA oligomers, less than ~50 bases long, bound to DNA target in standard buffer solutions is approximated by 2*(the number of A and T bases along the oligomer)+4*(the number of G and C bases along the oligomer) in degrees Celsius. Hence, complete sets of DNA probes with approximately equal stringency can be assembled using the following protocol:

1) Assemble the complete set of probes of length N bases, where N is an even number, and where all bases are selected from A and T.

2) Assemble the complete set of probes of length (N−1) bases where one base must be selected from either a C or G, and the remaining (N−2) bases are selected from A and T.

3) Assemble the complete set of probes of length (N−2) bases where two base must be selected from C and G, and the remaining (N−4) bases are selected from A and T.

4) Assemble the complete set of probes of length (N−3) bases where three base must be selected from C and G, and the remaining (N−6) bases are selected from A and T.

5) Continue assembling complete sets of probes according to subsequent steps in the series defined by steps 1-4 until reaching the shortest probes of length N/2 as specified in step 6.

6) Assemble the complete set of probes of length (N/2) bases where all bases must be selected from C and G.

7) Combine all sets of probes assembled in steps 1-6 to form a complete set of hybridization probes, capable of hybridizing to all possible target DNA sequences.

Per the usual definition, a complete set of probes of length N includes probes with all possible combinations of the allowable bases. All members of the set of probes generated by the above protocol will have approximately the same melting temperature in standard aqueous buffer solutions of 2*N degrees C., where N is an even number of length less than approximately 50 bases. The protocol can be applied where N is an odd number by continuing the series of procedures defined in steps 1-4 until completing the protocol after probes of exclusively C and G are formed. The maximum probe length, N, is usually in the range of 4 to 50 bases, and preferably in the range of 8 to 20 bases. Longer and shorter probes are also acceptable.

Alternately, the sets of probes formed are not required to be complete sets. For instance, when existing information about the target sequence is sufficient to exclude certain sequences, then probes complementary to these excluded sequences are not needed and would only dilute the useful probes. In other circumstances, it can be beneficial to form several separate subsets of probes, which taken together form a complete set. The subsets can be beneficially designed such that there are no complementary pairs within a given subset, thus avoiding probe to probe hybridization. Additionally, different subsets can have different optimal stringency conditions.

Alternate Methods for the Manufacture of Labeled-Probe-Assemblies

Labeled-probe-assemblies can be fabricated as complete units or can be made by linking together independently fabricated probes and label-assemblies. Furthermore, these assemblies can be built-up from multiple independently formed pieces or replicated as complete units. Both synthetic and biologic methods can be applied to form separate pieces and complete units. All of the necessary fabrication processes, materials, and equipment are existing and are commonly used in the Biotech, recombinant DNA, and DNA synthesis fields. Hence, many methods for fabricating labeled-probe-assemblies can be envision by the knowledgeable practitioner. In presenting various manufacturing methods, more emphasis will be directed to the high-level process flow than to dwelling on details of standard and existing processes. However, several processes unique to this invention are presented. These processes are critical to the cost-effective and efficient production of labeled-probe-assemblies, and are presented in detail.

Fabrication of Master Labeled-Probe-Assemblies and Labeled-Probe-Assemblies with Staining Prior to Assembly Listed immediately below is a process flow that describes one method for the fabrication of labeled-probe-assemblies from DNA using solid-phase synthesis and biologic processes. All possible N-mer probes are fabricated (for N-mer length probes there are N raised to the fourth power possible unique probe sequences). In the process, components may be stained prior to the final assembly steps. The process illustrated is specific to the information encoding protocol detailed in FIG. 21. Alternately, this process can be used without staining step 8 to fabricate a master set of labeled-probe-assemblies, suitable for subsequent replication (amplification).

1. Generate and keep separate five different types of components. The five different components are the probe-to-label assembly linker and each of the four possible encoded bases A, T, C, and G. Generate multiple copies of each type of component.

2. Ligate each of the different types of components into a separate population of plasmids, one population of plasmids for each different type of component.

3. Amplify the number of each of these isolated populations of plasmids by insertion into vectors and cloning of the vectors.

4. Extract and keep separate the components from the different cloning vectors and plasmid populations. The plasmids and components are designed so that the two ends of each of the extracted components have different overhang sequences. (For each component, its two ends have different overhang sequences, and all of the five different types of components have the same two overhang sequences.)

5. Synthesize multiple copies of 2N+2 unique component to component linkers.

6. For each of the four different encoded base components, divide each into N+1 separate vessels. Place the probe to label assembly linkers into their own vessel.

7. To each of the vessels, add the associated component to component linkers and ligate the component to component linkers to the components 8. Stain per stain-Manufacturer's standard protocol the contents of each vessel.

9. Into $N^4$ different vessels, add two parts probe-to-label assembly linker, one part of each of N different base encoding components, and one part of the correct base encoding component that will be the start indicator, and hybridize and ligate the components together.

10. Synthesize multiple copies of the $N^4$ unique probe sequences with appended base sequence that is complementary to the overhang sequence of the probe-end of the probe to label assembly linker component. Place each of the $N^4$ different types of probe in its own vessel.

11. Add the associated probe type to the vessel with the corresponding label-assembly, hybridize and ligate together.

12. Use or store (minimize exposure to oxidizers and use free-radical getters to reduce strand breakage)

Replicating DNA Label-Assemblies and Labeled-Probe-Assemblies

Listed below are processes for replicating labeled hybridization-probe assemblies. This process starts with an existing set of cloneable-labeled-probe-assemblies, derived from Master labeled-probe-assemblies, which are not stained, and from these, generates multiple copies of all the different labeled-probe-assemblies. Cloneable-labeled-probe-assemblies are labeled-probe-assemblies with any added features required for cloning of the assemblies and for recovery of the labeled-probe-assemblies after cloning, including uncovering of the single-strand probe sequences. In addition, the cloneable-labeled-probe-assemblies do not include any DNA sequence regions that can not be cloned or that would lead to failure of the cloning vectors, for example, by such means as generating proteins or RNA molecules that are toxic to the cloning vectors.

The process presented above can be used to generate the needed set of clonable-labeled-probe-assemblies, with the exception that the staining step, step 8, is omitted. In general, any method for generating the complete set of clonable-labeled-probe-assemblies is acceptable.

In the processes illustrated below, multiple different labeled-probe-assemblies can be fabricated simultaneously in a single vessel, and all are simultaneously stained in a single vessel. By this process, some or all of the different types of labeled-probe-assemblies can be replicated together in a single vessel and stained together in a single vessel. The process illustrated is thus a highly efficient and cost effective method of generating multiple copies of a large number of different labeled-probe-assemblies.

Process Flow for Amplification of Labeled-Probe-Assemblies (Staining with Modified Nucleotides)

1. Acquire or generate a complete set of cloneable-labeled-probe-assemblies, including multiple copies of each of the different types of cloneable-labeled-probe-assemblies. Each clonable-labeled-probe-assembly is supplied as dsDNA, with the possible exception of single strand overhanging ends designed to facilitate insertion into cloning vectors. Multiple different types of labeled-probe-assemblies can be linked together into single clonable-labeled-probe-assemblies with dsDNA of specific sequences between each labeled-probe-assembly to facilitate subsequent separation of the different labeled-probe-assemblies, including uncovering of the single-strand probe sequences. The specific sequences are typically recognition sequences for nicking and/or restriction enzymes, and they are used as in the process detailed for FIGS. 4 and 5. (In alternate embodiment, acquire a complete set of labeled-probe-assemblies with primer ends, all optimized for PCR.)

2. Insert labeled-probe-assemblies into cloning vector by ligation. Any suitable cloning vector is acceptable, including plasmid, M13 linear DNA, cosmid, BAC (Bacterial Artificial Chromosome), and YAC (Yeast Artificial Chromosome). Infect suitable cloning host, such as bacterium, virus, and yeast cell, and allow cloning host to reproduce and replicate cloning vectors. (In alternate embodiment, amplify with PCR instead of or in addition to cloning.)

3. For stain-types that are initially fabricated as modified nucleotides, such as radio-nucleotides and fluorescence labeled nucleotides, divide the growing colonies and move a portion into storage for future use, and to the other portion, add the modified nucleotides prior to the last round or last several rounds of replication.

4. Recover labeled-probe-assemblies from cloning vectors, typically by steps of extraction of DNA and treatment of DNA with restriction enzymes and nicking enzymes. Heat inactivate or remove enzymes. Purify labeled-probe-assemblies.

5. Use or store (minimize exposure to oxidizers and use free-radical getters to reduce strand breakage)

Process Flow for Amplification of Labeled-Probe-Assemblies (Staining with Intercalating Stain Types)

1. Acquire or generate a complete set of cloneable-labeled-probe-assemblies, including multiple copies of each of the different types of cloneable-labeled-probe-assemblies. Each clonable-labeled-probe-assembly is supplied as dsDNA, with the possible exception of single strand overhanging ends designed to facilitate insertion into cloning vectors. Multiple different types of labeled-probe-assemblies can be linked together into single clonable-labeled-probe-assemblies with dsDNA of specific sequences between each labeled-probe-assembly to facilitate subsequent separation of the different labeled-probe-assemblies, including uncovering of the single-strand probe sequences. The specific sequences are typically recognition sequences for nicking and/or restriction enzymes, and they are used as in the process detailed for FIGS. 4 and 5. (In alternate embodiment, acquire a complete set of labeled-probe-assemblies with primer ends, all optimized for PCR.)

2. Insert labeled-probe-assemblies into cloning vector by ligation. Any suitable cloning vector is acceptable, including plasmid, M13 linear DNA, cosmid, BAC (Bacterial Artificial Chromosome), and YAC (Yeast Artificial Chromosome). Infect suitable cloning host, such as bacterium, virus, and yeast cell, and allow cloning host to reproduce and replicate cloning vectors. (In alternate embodiment, amplify with PCR instead of or in addition to cloning.)

3. Recover labeled-probe-assemblies from cloning vectors, typically by steps of extraction of DNA and treatment of DNA with restriction enzymes and nicking enzymes. Heat inactivate or remove enzymes. Purify labeled-probe-assemblies.

4. For intercalating stain-types or other stains and staining methods that bind stain to either dsDNA preferentially or ssDNA preferentially, stain labeled-probe-assemblies using one of the controlled strand-separation staining methods.

5. Use or store (minimize exposure to oxidizers and use free-radical getters to reduce strand breakage)

Process Flow for Amplification of Labeled-Probe-Assemblies (Inverse Staining with Intercalating Stain Types)

1. Acquire or generate a complete set of cloneable-labeled-probe-assemblies, including multiple copies of each of the different types of cloneable-labeled-probe-assemblies. Each clonable-labeled-probe-assembly is supplied as dsDNA, with the possible exception of single strand overhanging ends designed to facilitate insertion into cloning vectors. Multiple different types of labeled-probe-assemblies can be linked together into single clonable-labeled-probe-assemblies with dsDNA of specific sequences between each labeled-probe-assembly to facilitate subsequent separation of the different labeled-probe-assemblies, including uncovering of the single-strand probe sequences. The specific sequences are typically recognition sequences for nicking and/or restriction enzymes, and they are used as in the process detailed for FIGS. 4 and 5. (In alternate embodiment, acquire a complete set of labeled-probe-assemblies with primer ends, all optimized for PCR.)

2. Insert labeled-probe-assemblies into cloning vector by ligation. Any suitable cloning vector is acceptable, including plasmid, M13 linear DNA, cosmid, BAC (Bacterial Artificial Chromosome), and YAC (Yeast Artificial Chromosome). Infect suitable cloning host, such as bacterium, virus, and yeast cell, and allow cloning host to reproduce and replicate cloning vectors. (In alternate embodiment, amplify with PCR instead of or in addition to cloning.)

3. Recover labeled-probe-assemblies from cloning vectors, typically by steps of extraction of DNA and treatment of DNA with restriction enzymes and nicking enzymes. Heat inactivate or remove enzymes. Purify labeled-probe-assemblies.

4. Bind sequence specific DNA binding proteins to labeled-probe-assemblies to protect footprint areas from stain.

5. Stain DNA that is not protected by bound protein with suitable stain type, such as intercalating stain-types or other stains and staining methods that bind stain to DNA. (Optionally, cross-link stain to labeled-probe-assembly.)

6. Remove or consume bound proteins from labeled-probe-assemblies.

7. Repeat steps 4 and 5 and/or 4 through 6, using different types of proteins and stains (DNA binding proteins with different binding sequences, and fluorescent stains with different excitation and/or emission spectra or the same type of stain but at different density).

8. Use or store (minimize exposure to oxidizers and use free-radical getters to reduce strand breakage)

Process Flow for Amplification of Labeled-Probe-Assemblies (Stain after Binding to Target)

1. Acquire or generate a complete set of cloneable-labeled-probe-assemblies, including multiple copies of each of the different types of cloneable-labeled-probe-assemblies. Each clonable-labeled-probe-assembly is supplied as dsDNA, with the possible exception of single strand overhanging ends designed to facilitate insertion into cloning vectors. Multiple different types of labeled-probe-assemblies can be linked together into single clonable-labeled-probe-assemblies with dsDNA of specific sequences between each labeled-probe-assembly to facilitate subsequent separation of the different labeled-probe-assemblies, including uncovering of the single-strand probe sequences. The specific sequences are typically recognition sequences for nicking and/or restriction enzymes, and they are used as in the process detailed for FIGS. 4 and 5. (In alternate embodiment, acquire a complete set of labeled-probe-assemblies with primer ends, all optimized for PCR.)

2. Insert labeled-probe-assemblies into cloning vector by ligation. Any suitable cloning vector is acceptable, including plasmid, M13 linear DNA, cosmid, BAC (Bacterial Artificial Chromosome), and YAC (Yeast Artificial Chromosome). Infect suitable cloning host, such as bacterium, virus, and yeast cell, and allow cloning host to reproduce and replicate cloning vectors. (In alternate embodiment, amplify with PCR instead of or in addition to cloning.)

3. Recover labeled-probe-assemblies from cloning vectors, typically by steps of extraction of DNA and treatment of DNA with restriction enzymes and nicking enzymes. Heat inactivate or remove enzymes. Purify labeled-probe-assemblies.

4. Use or store (minimize exposure to oxidizers and use free-radical getters to reduce strand breakage)

Methods of Staining Label-Assemblies and Labeled-Probe-Assemblies

Controlled Strand-Separation Staining Methods

Controlled strand-separation staining methods are outlined below. In the controlled strand-separation staining methods the label-assembly is constructed such that the thermal stability, melting temperature, is specified, predetermined, along the length of the dsDNA label-assembly and can vary along the length. The thermal stability of the double helix is largely determined by the ratio of G-C content to A-T content and hence by the base sequence. For the dsDNA label-assembly, regions with higher percentage of G-C bases will have higher thermal stability than regions with lower percentage of G-C bases, and in this way, the thermal stability, melting temperature, can be varied along the length of the label-assembly.

G-C content also increases duplex stability to high pH. Hence, low G-C content regions of labeled-probe assemblies may be selectively denatured by controlled increases in solution pH and/or increases in temperature. Selective melting of dsDNA by temperature or pH excursions is presented here as a means of selectively staining certain regions of labeled-probe-assemblies. Temperature and pH excursions have been used previously to study G-C content variations along dsDNA samples, as described in Inman, R. B., Schnos, M., J. Mol. Biol. (49): 93 98 (1970), Inman, R. B., J. Mol. Biol. (18): 464 (1966), and Inman, R. B., J. Mol. Biol. (28): 103 (1967).

Variations in melting temperature along the label assembly can be used to stain specific regions with higher melting temperature while leaving lower melting temperature regions unstained. This is accomplished by heating the solution containing the label-assemblies to a temperature sufficient to melt the lower melting temperature regions without melting the higher melting temperature regions. This yields label-assemblies with regions of single-strand DNA, pairs of ssDNA, and other regions of dsDNA. At this point a stain type, or types, is added that preferentially stains annealed double-stranded DNA (such as dsDNA intercalating stains). Staining of the lower melting temperature regions is prevented by removing free stain from the solution before cooling below the annealing temperature of the lower melting temperature regions.

Similarly, an alternate process can be used to stain the lower melting temperature regions while not staining the higher melting temperature regions. This is accomplished by melting just the lower melting temperature regions, as above, and staining the single strand DNA prior to cooling the solution to anneal all regions. Suitable methods for exclusively, or primarily, staining the ssDNA include cross-linking stain molecules to exposed bases, such as to exposed terminal amines, and removal of some exposed bases and cross-linking of stain molecules to the single-stranded backbone.

Note that the key steps are to melt selected regions of the label assembly and keep these regions melted, single strand, during the staining process. Stability of the double helix within a given region of label-assembly is designed-in by using specific percentages of G-C content and specific base sequences. Melting of selected regions can be accomplished by varying and controlling the temperature of the solution and also by varying and controlling the solution salt concentration, the monovalent ion (Na+) concentration, the divalent ion concentration, the solution pH, and by varying other parameters of the solution. The references given above (Inman) give representative solution temperature for one solution chemistry. Single-strand binding (SSB) proteins can also be added to the solution to stabilize the melted, single-strand, regions, and double-strand binding proteins can be added to stabilize the annealed, double-strand DNA. Regions that are to remain double-strand during staining can be fabricated with specific base sequences at various points, preferentially at and near the ends of the double-strand regions, that are recognition sequences for sequence-specific dsDNA-binding proteins. These sequence-specific dsDNA-binding proteins can be added, and even cross-linked to, the label-assemblies prior to melting of regions of the label-assembly. After staining, any proteins can be removed, if desired, by standard DNA extraction and purification processes that are compatible with stained dsDNA, such as protein digestion with protein kinase K.

To more clearly illustrate the controlled strand-separation staining method, several specific cases will be detailed. The first case is that of a single stain type and density of stain. This method can be applied to stain label-assemblies as needed for information encoding protocols that only use stained and unstained regions, such as those described for FIGS. 18 and 19. For this case, the label-assemblies consist of only stained and unstained regions, and hence for the controlled strand-separation staining method, regions to be stained are fabricated to have a minimum melting temperature and regions that are not to be stained are fabricated to have a maximum melting temperature, and the difference between this minimum high temperature and maximum low temperature is made sufficiently different such that a solution of the label-assemblies (or labeled-probe-assemblies) can be held at a temperature such that the low melting temperature regions are melted, and hence ssDNA, while the high melting temperature regions remain annealed, and hence dsDNA.

Controlled Strand-Separation Staining Process Flow—Dilution Protocol, No Removal of Stain Between Steps—Case with Single Stain Type and Four Densities of Stain, and Case with Four Stain Types.

1. Place solution of labeled-probe-assemblies in vessel

2. Heat vessel such that solution temperature is between melting temperature of first stained regions and second stained regions 3. Add pre-heated stain solution to labeled-probe-assembly solution and hold at temperature for sufficient time to achieve desired density of stain.

4. Dilute solution to reduce density of stain and/or add second type of stain

5. Cool solution temperature to between melting temperature of second stained regions and third stained regions 6. Hold at temperature for sufficient time to achieve desired density of stain.

7. Repeat steps 4-6 as need to process all regions to be stained.

8. Dilute and remove stain from solution

9. Cool solution of newly stained labeled-probe-assemblies for use and/or storage Stain all with dsDNA Specific Stain and Heat and/or Increase pH to Melt Selected Regions of Label-Assembly and Remove Stain from Melted Regions An alternate version of the controlled strand-separation staining method uses label-assemblies with information encoded as variations in melting temperature along the label-assemblies, as described above. However in this alternate method, the entire length of the label assembly is stained using dsDNA intercalating stain, such as Ethidium Bromide, intercalating dimeric cyanine nucleic acid stains including those from Invitrogen (YOYO-1, etc., and using standard Invitrogen staining procedures), and other intercalating stains. Following staining the solution containing the stained label-assemblies is heated, and/or the solution chemistry changed (such as increasing the pH), to melt the low melting temperature regions of the label-assemblies, thus liberating the intercalated stain from the melted regions while the un-melted regions remain stained. Free stain in the solution is diluted, dialyzed, or removed prior to cooling and annealing of the low melting temperature regions. This staining protocol can be applied to stain labeled-probe-assemblies prior to their use, after binding to their target, just prior to and as the labeled-probe-assemblies are being extended onto the substrate, after the labeled-probe-assemblies have been extended and fixed to the substrate, or at any time prior to visualization for information readout.

Denaturing selected regions of DNA, lower G-C concentration regions, can be done by elevating solution temperature, by elevated solution pH, or a combination of the two. In one embodiment, the solution temperature is held at room temperature and the solution pH is increased by adding 1M NaOH or other base to a maximum pH in the range of roughly 11.5 to 12.2, depending on the salt concentration of the solution and the G-C content of the regions that are to be denatured. For staining protocols that employ only stained and unstained regions, the regions to remain stained may have G-C content of approximately 55% and greater, and the regions that are to be unstained may have G-C content of approximately 45% and less. Other ranges of G-C content can also be acceptable, as the method is affected by the difference in G-C content between regions and not the absolute G-C content.

In one embodiment, the information encoding protocol detailed for FIG. 19 is produced by staining all labeled-probe-assemblies with YOYO-1, following standard procedures supplied by Invitrogen. All regions to remain stained, regions 1920, 1962 and 1966 as illustrated in FIG. 19, are fabricated of dsDNA with running mean G-C composition between approximately 55 and 65% or greater. The running mean is calculated over a span of 21 bases, hence for every base along the regions, the G-C content of the 21 bases centered on any given base is between approximately 55 and 65%. Similarly, the running mean G-C content along the regions to become unstained, regions 1960 and 1968 as illustrated in FIG. 19, is fabricated to be less than approximately 45%. After the labeled-probe-assemblies have been fabricated, stained, used up to the point of having been extended and fixed by drying to the substrate, the substrate is placed in a vessel and rinsed with high-pH solution. The pH of the high-pH solution is typically in the range of 11.5 to 12.2 pH, and usually approximately 11.8 pH. Suitable high-pH solution has 0.02M Na2CO3 and 0.005M Na2EDTA with pH adjusted by addition of 1M NaOH. Rinse the substrate with the high-pH solution for approximately 1 to 10 minutes, then rinse with cold deionized water for about 1 minute or longer, then dry under a nitrogen stream. The substrate bound labeled-probe-assemblies are now ready for data readout.

A further alternate embodiment of information visualization method can be described as the controlled strand-separation information visualization method. In this embodiment of staining and visualization of information encoded along labeled-probe-assemblies, the entire length of the label-assemblies is stained, and the information is encoded region-by-region as variations in thermal stability, melting temperature, and/or stability at elevated pH of the regions. In practice, the stability of a given region is determined by the average G-C content in that region, and hence by the base sequence of the labeled-probe-assembly. As given above, for staining protocols that employ only stained (dsDNA) and unstained (ssDNA) regions, the regions to remain double-stranded may have G-C content of approximately 55% and greater, and the regions that are to be single-stranded may have G-C content of approximately 45% and less. Other ranges of G-C content can also be acceptable, as the method is affected by the difference in G-C content between regions and not the absolute G-C content.

In use, after labeled-probe-assemblies become attached to their targets and prior to extension of the labeled-probe-assemblies over the surface of the substrate, the temperature of the solution is increased, and possibly the composition of the solution modified, such that all regions with low melting temperature are melted and none of the other regions are melted. This can alternately be accomplished in a room temperature solution by increasing the solution pH to the range of roughly 11.5 to 12.2. These conditions are maintained as the labeled-probe-assemblies are extended over the surface of the substrate. The encoded information is then readout by viewing the extended labeled-probe-assemblies and recording the order, and, depending on the specific information encoding protocol employed, the length, of the various melted and annealed regions.

Staining the labeled-probe-assembly allows it to be more easily viewed. Suitable stains include radioisotope labeled bases, fluorescent modified bases, fluorescent tagged branches along regions, as well as other stains. Variations in thermal stability of regions along the label-assemblies are measured as variations in the local melting temperature of the regions.

Staining Method Using Sequence-Specific DNA-Modifying Enzymes

Generate labeled-probe-assemblies, for example by processes outlined above, and stain using sequence-specific DNA-modifying enzymes either in vivo during cloning, or in vitro after extraction from the cloning vector. Suitable sequence-specific DNA-modifying enzymes include DNA Methylases, which can be used to add radioisotopes, tritium labeled methyl groups, along the label assembly. Alternately, nicking and other restriction enzymes can be used to generate damage along the label assembly with sequence specific targeting. DNA Repair enzymes and/or polymerases can then be used to add radioisotope or fluorescent labeled nucleotides or oligomers at, and adjacent to, the damage points.

Staining Methods Using Sequence-Specific DNA-Binding Proteins

In one embodiment, the label-assemblies are decorated with stained proteins, hence the label-assembly serves as a backbone along which the stained proteins affix. The label-assembly also carries the information that determines where the stained proteins can affix. Stain label-assemblies by sequence directed binding of stained proteins and proteins to be stained after binding to the label-assemblies. In the label-assemblies, include sequences that are recognition sequences for sequence-specific DNA-binding proteins. Stain by adding protein and allowing binding to label-assembly. Protein may be pre-stained or stained later. The protein to label-assembly binding step can be placed after hybridization and extension or earlier in the process. Any bound proteins may be cross-linked to the label-assemblies.

In an alternate embodiment of the method, label-assemblies are stained by inverse foot-printing. In label assembly, include sequences that are recognition sequences for sequence-specific DNA-binding proteins. Add protein and allow binding to label-assembly. Add DNA stain (such as YOYO-1) to solution and allow binding to exposed DNA. DNA that is covered by protein is isolated from the stain and is not stained. Remove free stain from solution. Remove protein from DNA, if desired. Use and/or store labeled-probe-assemblies. Regions of the label assembly that have the highest density of DNA binding protein recognition sequences will receive the lowest density of stain and regions with zero DNA binding protein recognition sequences will receive the maximum density of stain. Hence the base sequence along the label assembly determines the variation in the density of stain along the label assembly.

This method can be extended to staining with multiple, unique, stain types by fabricating label-assemblies with the recognition sequences for multiple types of sequence specific DNA binding proteins, where the recognition sequence for each different type is unique. Staining is then done by repeated process steps of binding to the label-assemblies a first set of proteins followed by staining with a first set of stains. These steps are followed by removal from the solution free stain and then bound protein before proceeding with these same steps again with a second set of proteins and a second set of stains. Additional sets of stains and proteins can be used in subsequent cycles of the process until the desire number of stain and protein sets are utilized.

Alternate Embodiments of Method of Use of Labeled-Probe-Assemblies in Sequencing FIG. 45 presents an alternate process flow for sequencing of ssDNA and dsDNA samples. The method employs substrate elongation and fluorescent detection by use of secondary labeled probes. The method differs from that presented in FIG. 44, in that manufactured oligomers are not used, rather the sample DNA is fragmented into separately sequenced sections during substrate elongation.

In FIG. 45, boxes 44010, 44020, 44030, 44035, 44040, 44050, 44055, 44060, 44070, and 44080 can be functionally identical to the boxes of the same number in FIG. 44, and the detailed descriptions have already been presented above. What is different is that oligomers are not hybridized to the sample DNA, as in box 44032 of FIG. 44. In the process of FIG. 45, the sample DNA molecules are stretched to their breaking points and fragmented during the process of substrate elongation, deformation, box 44035. Continued substrate elongation during the process of box 44035 then spatially separates the substrate-bound sample DNA fragments. The benefits of this process flow include reduced number of process steps and reduced materials requirements. FIG. 27 illustrates the top view of substrate 1302 and a portion of one sample DNA molecule. The individual fragments 2702 of the sample DNA molecule are spatially separated during step 44035 of FIG. 45. As illustrated in FIG. 27, labeled-probe-assemblies 2704 are extended over the surface of substrate 1302, and are hybridized to fragments 2702 by probes 2706. As indicated, the sample DNA molecule was extended in the Y-direction, and the substrate was elongated in the Y-direction. The labeled-probe-assemblies were extended in the X-direction.

FIG. 46 presents a method for sequencing ssDNA and dsDNA that uses substrate elongation, and like most other methods detailed in this document, is compatible with, and in fact benefits from, long sample DNA molecules. The method is generic in that it can be used with many different methods for sequencing the short fragments of sample DNA that are formed during substrate elongation. Specifically, the sequencing method is not limited to application of labeled-probe-assemblies. Other sequencing methods useful for sequencing short fragments of DNA, and that are suitable for use here, include pyro-sequencing and other sequencing-by-synthesis techniques, hybridization with labeled probes, in addition to labeled-probe-assemblies, and other techniques.

The overall method detailed in FIG. 46 provides significant benefits over existing sequencing methods. First, the order and approximate location of the sequence fragments along the sample DNA molecule are determined during data collection. Hence, the fragments of sequence information collected can immediately be placed in the correct order in which they exist within the original sample DNA molecules. Furthermore, the approximate distance, in bases, between sequence fragments is also determined during data collection. Finally, long sample DNA molecules can be used, which allows many sequence fragments to be ordered and increases the probability of correctly overlapping sequence fragments during data analysis. These benefits stem from the use of long sample DNA molecules, extending them over the substrate, and elongating the substrate to spatially separate short section of the original sample DNA molecules. These benefits can be realized by any method for sequencing the short sections of DNA, including labeled-probe-assemblies. Any of the other process flows presented in this document could be similarly modified to use sequence detection by means other than labeled-probe-assemblies. For example, process flows illustrated in FIG. 44 or 47, which result in the sample DNA being replaced with substrate bound oligomers, can be adapted by replacing boxes 44040-60 of FIG. 44, or 47040-60 of FIG. 47, with box 44065 of FIG. 46.

Referring to FIG. 46, the process steps contained in boxes 44010, 44020, 44030, 44035, 44070, and 44080 can be functionally identical to the boxes of the same number in FIG. 44, and the detailed descriptions have already been presented above. Unique to the process flow illustrated in FIG. 46 is box 44065 that covers the detection and readout of sequence data from the sample DNA fragments. Any suitable method for sequencing of the short sample DNA fragments, or determining one or more bases of the fragments, can be applied. The readout apparatus employed is selected to complement the sequencing method, and often, the fluorescent microscopy setup with computer linked digital camera illustrated in FIG. 16 can be used.

The method illustrated in FIG. 47 is another alternate method for sequencing ssDNA and dsDNA samples, and uses substrate elongation. The figure illustrates a flow that does not use secondary labeled probes, but rather directly stained labeled-probe-assemblies or stained proteins bound to the labeled-probe-assemblies in predetermined patterns. The method allows sequencing of one strand, even when applied to dsDNA samples. This provides advantages during data analysis, as there is certainty as to which strand a given labeled-probe-assembly has hybridized, and hence less data need be collected and the data are more easily analyzed.

Referring to FIG. 47, the process steps contained in boxes 47010, 47020, 47035, 47040, 47050, 47060, 47070, and 47080 can be functionally identical to the corresponding boxes 44010, 44020, 44035, 44040, 44050, 44060, 44070, and 44080, respectively, in FIG. 44, and the detailed descriptions have already been presented above. Box 47014 of FIG. 47 covers the hybridization of oligomers to single strands of sample DNA. Typically, the oligomers are the same length, number of bases, as the probes on the labeled-probe-assemblies, but longer and shorter oligomers can be used. If the sample DNA is double-stranded, then the sample DNA is denature prior to the oligomer hybridization step. The oligomers may be DNA, RNA, PNA, or heterostructures, and often one end of each oligomer is modified to facilitate cross-linking of the hybridized oligomers to the substrate. One suitable end-group modification results in 3'-S—H termination on each oligomer. After hybridizing oligomers to the sample DNA, excess oligomers are removed by standard techniques, such as gel purification.

Box 47030 of FIG. 47 covers extending the sample DNA onto the substrate and cross-linking the oligomers to the substrate. FIG. 28 illustrates the top view of the single-stranded sample DNA 2802 with hybridized oligomers 2804 extended over substrate 1302. The sample DNA molecule 2802 is shown extended in the X-direction. To produce this geometry, the processes of box 44030 of FIG. 44 can be employed. A more optimal process uses the same apparatus, materials, and technique, except that the rate at which the meniscus is lowered is increased such that the exposed portion of the substrate does not become thoroughly dried, and the substrate is not dried immediately following the extension step. Immediately after the meniscus is completely lowered, to the point where the extension vessel is empty, the extension vessel is filled with cross-linking solution. For example, the substrate is fabricated so that it has amine-terminated surface molecules, and the oligomers have terminal 3'-S—H, then a cross-linking solution containing 4-(N-Maleimidomethyl) cyclohexane-1-carboxylic acid 3-sulfo-N-hydroxysuccinimide ester sodium salt (($C_{16}H_{17}N_2O_9SNa$) Sigma-Aldrich catalog number M 6035, Sigma-Aldrich Co., with protocol reference Hashida, et al., J. Applied Biochem. (6): 56 63 (1984), can be used to cross-link the oligomers to the substrate. Once the oligomers that are hybridized to the sample DNA have been cross-linked to the substrate, the sample DNA is no longer required, and the sample DNA can be removed, although this is not required. This process is covered in box 47034 of FIG. 47. In cases where RNA and PNA oligomers are used, the sample DNA can be removed by consuming the DNA with RNase-free DNase enzymes. In cases where DNA oligomers are used, it is simplest and acceptable to skip this step and leave the sample DNA on the substrate. After box 47034, the remainder of the process flow follows the standard flow first detailed in FIG. 44, except that box 44055 of FIG. 44 has been excluded, as in this illustration, visualization methods other than secondary labeled probes are assumed.

The geometry of the sample DNA and labeled-probe-assemblies at several stages during the process flow detailed in FIG. 47 is illustrated in FIGS. 28-31. FIG. 28 is described above. FIGS. 29-31 illustrate the geometry of oligomers and labeled-probe-assemblies over a portion of substrate 1302, in top-view. FIG. 29 illustrates substrate-anchored oligomers 2804 and anchors 2908 after substrate 1302 has been elongated. The substrate 1302 is elongated by typically 100 to 1000 times its original length. FIG. 30 illustrates the substrate 1302 with oligomers 2804, anchors 2908, and hybridized labeled-probe-assemblies 3006, prior to extension of the labeled-probe-assemblies. FIG. 31 illustrates substrate 1302 with oligomers 2804, anchors 2908, and hybridized labeled-probe-assemblies 3006 extended over substrate 1302 in the Y-direction. FIG. 31 illustrates the final geometry of the labeled-probe-assemblies 3006 as ready for data readout.

FIG. 48 illustrates a process flow for sequencing dsDNA samples with use of DNA-binding proteins. The process steps contained in boxes 48010, 48020, 48035, 48040, 48050, 48060, 48070, and 48080 can be functionally identical to the corresponding boxes 44010, 44020, 44035, 44040, 44050, 44060, 44070, and 44080, respectively, in FIG. 44, and the detailed descriptions have already been presented above. Box 48028 covers the binding of DNA-binding proteins to the sample DNA. Suitable DNA-binding proteins include histones, such as Histone from calf thymus, Type II-A, catalog number H 9250, 2002-2003 Biochemicals and Reagents catalog, Sigma-Aldrich Co., St. Louis, Mo., and other largely non-sequence-specific DNA-binding proteins, such as protamines and protamine sulfate. Histones are useful because their binding is non-sequence-specific, each histone generally binds to a fixed number of base-pairs, which is useful information during data analysis, 48070, and DNA bound to the core of the histone particle is protected from nucleases. In one embodiment, the DNA is cross-linked to the DNA-binding proteins, and in another embodiment, it is not.

Box 48030 of FIG. 48 covers the extension and fixing of the sample DNA to the substrate. This process can use the same apparatus, material, and techniques as detailed for box 44030 of FIG. 44 or as modified for box 47030 of FIG. 47. Fixing to the substrate can be accomplished by drying, or by limited drying followed by immersion in a protein-to-substrate cross-linking solution, such as solutions containing gluteraldehyde or formaldehyde, per standard protocols, in combination with amine containing substrates, such as mixtures of paraffin wax and 1-octadecylamine. FIG. 32 illustrates a top-view of a portion of substrate 1302 at one sample DNA molecule 3202 with bound DNA-binding proteins 3204. Sample DNA molecule 3202 was anchored to substrate 1302 prior to extension by substrate bound avidin molecule 3206.

Box 48031 of FIG. 48 illustrates the modification of the sample DNA to prepare it for hybridization with labeled-probe-assemblies. The exposed DNA, that DNA not protected within the DNA-binding proteins, is double-strand cleaved, by for example limited exposure to DNase I with Mn++, and not Mg++, ions in the solution. The dangling ends of the exposed dsDNA are then treated to form overhanging single-strand ends. This can be accomplished by treatment with double-stranded 5' to 3' exonucleases, such as Lambda exonuclease and T7 Gene 6 exonuclease, or double-stranded 3' to 5' exonucleases, such as Exonuclease III (Exo III). These enzymes are commercially available, as are the necessary reagents and protocols for their use. The reaction is limited by the footprint of the DNA-binding proteins. These single-stranded regions are now available for hybridization with labeled-probe-assemblies. After box 48031, the remainder of the process flow follows the flow detailed in FIG. 47. Finally, note that box 48031 could be placed between boxes 48035 and 48040, in which case the sample DNA will have been cleaved during the elongation step of box 48035, the overhanging ends are then formed as described above in this paragraph.

Referring to the process flow of FIG. 48, FIGS. 33-35 illustrate the top-view layout of a portion of substrate 1302 at one section of fragmented DNA molecule after the steps of substrate elongation, hybridization and extension of labeled-probe-assemblies in one direction, and in the opposite direction, respectively. Illustrated in FIGS. 33-35 are substrate bound avidin molecule 3206, DNA-binding proteins 3204, and single-stranded lengths of fragmented sample DNA molecule 3302. The substrate is elongated along the same direction in which the sample DNA molecule is extended, the Y-direction as illustrated in FIGS. 32-35. FIGS. 34 and 35 illustrate the first set of labeled-probe-assemblies 3402 to be hybridized to 3302 and extended in the +X-direction, and the second set of labeled-probe-assemblies 3502, hybridized to available 3302 and extended in the −X-direction (minus X-direction).

The alternate sequencing method illustrated in FIG. 49 is suitable for dsDNA samples, and using nicking of the sample DNA and cross-linking between the substrate and the DNA at the nicks. Boxes 49010, 49020, 49030, 49035, 49040, 49050, 49060, 49070, and 49080 can be functionally identical to the corresponding boxes 44010, 44020, 44030, 44035, 44040, 44050, 44060, 44070, and 44080, respectively, in FIG. 44, and the detailed descriptions have already been presented above. Box 49032 covers the optional nicking of the extended sample DNA, by for example limited exposure to DNase I with Mg++, and not Mn++, ions in the solution, UV exposure, or exposure to mutagenic chemicals. The number of nicks determines the mean length of the resulting sample DNA fragments, and optimum amount of nicking, determined by the concentration of enzyme, the solution temperature and chemistry, and the reaction time, must be determined experimentally. Following nicking, the exposed 3'-ends (or alternately the exposed 5'-ends) are modified to facilitate cross-linking to the substrate, such as modifying the 3'-OH into 3'-S—H groups (by means outlined for FIG. 44). Box 49033 covers the formation of cross-links between the substrate and the modified end-groups at the nicks along the sample DNA molecules. When the substrate includes amine-terminated molecules, such as phosphatidylethylamine, and the modified DNA end-groups are sulfhydryl groups, then any suitable heterobifunctional (amine-sulfhydryl) cross-linking agent can be used, such as those presented previously. Following box 49033, the remainder of the process flow of FIG. 49 is the same as detailed for the process illustrated in FIG. 47.

The alternate sequencing method illustrated in FIG. 50 is suitable for dsDNA samples, and uses nicking of the sample DNA and cross-linking between the substrate and the DNA at the nicks. Illustrated in this process flow is the method of hybridizing the labeled-probe-assemblies prior to elongating the substrate. Hybridizing before elongating has cost benefits as the necessary quantity of labeled-probe-assemblies in minimized. Boxes 50010, 50020, 50040, 50050, 50060, and 50070 can be functionally identical to the corresponding boxes 44010, 44020, 44040, 44050, 44060, and 44070, respectively, in FIG. 44, and the detailed descriptions have already been presented above. Box 50015 of FIG. 50 can employ the same nicking and end-group modification procedures described for box 49032 of FIG. 49.

Box 50030 of FIG. 50 can employ the same sample DNA extension and cross-linking procedures described for box 47030 of FIG. 47.

Box 50033 of FIG. 50 covers the digestion of double-stranded regions of sample DNA by consuming dsDNA along strands in the 5' to 3' direction by double-stranded 5' to 3' exonucleases, such as Lambda exonuclease and T7 Gene 6 exonuclease. This is for the case where strands are anchored to the substrate by modified 3'-ends. In the alternate case, where strands are bound to the substrate by their 5'-ends, then double-stranded 3' to 5' exonucleases, such as Exonuclease III (Exo III) are used. These enzymes are commercially available, as are the necessary reagents and protocols for their use. The reaction is continued until all or most of the double-stranded regions have been consumed or converted to single-stranded regions, leaving single-stranded fragments of sample DNA bound to the substrate.

Box 50040 covers the hybridization of labeled-probe-assemblies to the substrate-bound sections of sample DNA. Following or during hybridization, the hybridized labeled-probe-assemblies are cross-linked to the substrate. One method for making this attachment is to ligate the hybridized labeled-probe-assemblies to the substrate-bound sections of sample DNA using commercially available ligases, reagents, and protocols. These reactions can be carried out in a vessel made of polystyrene, or other non-reactive material.

Box 50045 of FIG. 50 covers the elongation of the substrate, after labeled-probe-assemblies have been hybridized to the substrate-bound sample DNA fragments. This is in the reverse order of other process flows presented, and the other process flows can be modified to this order as further alternate embodiments. The substrate elongation procedure can follow that detailed for box 44035 of FIG. 44, or an alternate procedure can be employed. One alternate substrate elongation procedure is detailed here. The process flow is as illustrated in FIG. 53, and the detailed description differs from that previously detailed for box 44035 of FIG. 44. In this alternate procedure, the sample DNA remains in contact with an aqueous solution during the substrate elongation.

Referring to FIG. 53, box 53000 covers the work that has already been done in steps 50010 through 50040. Box 53015 covers loading of the stretchable-substrate-support into the support-stretching fixture, preparing a water trough, and floating the substrate, sample side down, on the surface of an aqueous solution in the water trough. Suitable stretchable-substrate-support materials include those covered in reference to box 52010, above, with low durometer silicone rubber sheet one good choice. The support-stretching fixture 1412 is illustrated in FIG. 14a, and loading the stretchable-substrate-support 1402 into the fixture is accomplished by wrapping the ends of the stretchable-substrate-support 1402 around the bars 1404 so that the inner wraps are held in place by the stretchable-substrate-support. Unlike FIG. 14a, in this elongation process substrate 1302 is not initially mounted to the stretchable-substrate-support 1402, otherwise illustration 14a and the description of its operation are valid. The water trough 3602, illustrated in FIG. 36, is constructed of a non-reactive material, such as polystyrene or Teflon. Water trough 3602 is filled with aqueous solution 3604 to a level at or above the fixture standoffs 3606. Suitable aqueous solutions 3604 include water and solutions that promote duplex stability, such as 1M sodium salt solutions. The temperature of the solution 3604 is initially prepared at approximately 5 C to 20 C below the melting point of the substrate 1302 material, but not more than the melting temperature of the sample and labeled-probe-assemblies. The substrate 1302 is floated from the hybridization vessel onto the surface 3605 of the aqueous solution 3604 such that the side with the sample DNA is in the solution.

Box 53025 of FIG. 53 covers the heating of the stretchable-substrate-support, the lowering of the support-stretching fixture so that the stretchable-substrate-support contacts the substrate, and the melting or softening of the substrate. FIG. 36 illustrates hotplate 3608 heating the stretchable-substrate-support 1402 in support stretching fixture 1412. The temperature of hotplate 3608 is adjusted so that the temperature of stretchable-substrate-support 1402 reaches approximately 5 C to 20C above the melting point, or softening point, of the substrate 1302. Once heated, the support-stretching fixture 1412, as illustrated in FIG. 37, is lowered into water trough 3602 such that the stretchable-substrate-support 1402 contacts the substrate 1302. The initial heat of the stretchable-substrate-support 1402 melts or softens the substrate 1302, allowing it to be elongated by flowing or plastically deforming as the stretchable-substrate-support 1402 is stretched. Stretching of the stretchable-substrate-support 1402 is covered in box 53035 of FIG. 53 and illustrated in FIG. 38 in which both stretchable-substrate-support 1402 and substrate 1302 are elongated. Stretchable-substrate-support 1402 is stretched when valve 1416 is opened allowing high-pressure air from tank 1418 to pass through hose 1414 and into pneumatic cylinder 1410, as illustrated in FIGS. 36-38. FIGS. 14a-14c and their accompanying description illustrate how the pneumatic cylinder is coupled to the stretchable-substrate-support 1402.

The rate at which the stretchable-substrate-support 1402 is stretched is controlled to optimize the quality of information yielded during the data readout step. This rate is determined experimentally for a given substrate material and thickness, labeled-probe-assembly length, stretchable-substrate-support material and thickness, and the initial temperatures of the stretchable-substrate-support and water trough solution. The stretching rate is controlled by the pressure in tank 1418 and the degree to which valve 1416 is opened. Once stretching is complete, the stretchable-substrate-support is held fixed until the substrate solidifies, as covered in box 53045. Removal of the substrate from the stretchable-substrate-support, box 53050, and the addition of extra substrate material to the back of the substrate, box 53060, are preferably conducted while the sample side of the substrate remains in contact with the solution in the water trough. After the desired number of stretching cycles, box 53070, the substrate is slowly rotated 90 degrees around its long axis until it is vertical, and then the solution in the water trough is slowly removed through a siphon tube. As the level of the solution lowers, the substrate-bound labeled-probe-assemblies are extended over the surface of the substrate in a direction approximately perpendicular to the long axis of the substrate, box 50050 of FIG. 50. Boxes 50060 and 50070 of FIG. 50 cover the previously detailed steps of reading out the data from the extended labeled-probe-assemblies and analyzing that data to determine the base sequence of the sample molecules.

The alternate sequencing method illustrated in FIG. 51 has a number of optional steps that allow for processes with no substrate elongation, elongation along one axis, and elongation along two perpendicular axes. The process flows of FIG. 51 are suitable for use with labeled-probe-assemblies with bound DNA-binding proteins. In alternate embodiments, these DNA-binding proteins can be used to stain the labeled-probe-assemblies, as cleavable-linkers on labeled-probe-assemblies, as anchors for cleavable-linkers, and for combinations of these functions. The optional steps are indicated in FIG. 51 by dashed boxes 51035, 51056, and 51058. Boxes

51010, 51020, 51030, 51035, 51040, 51050, 51060, 51070, and 51080 can be functionally identical to the corresponding boxes 44010, 44020, 44030, 44035, 44040, 44050, 44060, 44070, and 44080, respectively, in FIG. 44, and the detailed descriptions have already been presented above. Modification of these processes is presented below.

In box 51030 of FIG. 51, the sample is spread and fixed to the substrate. In the case where the sample is DNA or RNA, the act of spreading the sample may include extending the sample along one direction as detailed for box 44030 of FIG. 44. For other types of samples, proteins for example, and DNA and RNA samples, a drop of solution containing the sample molecules can be dripped onto the substrate and allowed to dry, or the substrate can be tilted to allow the droplet to flow over the substrate. The solution is allowed to dry in order to fix the sample to the substrate.

Box 51035 of FIG. 51, is optional and is used to spatially separate sections of the sample molecules to allow increased resolution of the sample molecules. Box 51035 covers the elongation of the substrate to spatially separate target regions of the sample, and in alternate embodiments, can be conducted at any point before box 51060 of the process flow of FIG. 51. Elongation of the substrate can be performed by any method, including those detailed in FIGS. 52 and 53, and detailed in this document. If the sample molecules have been extended, then the substrate is most beneficially elongated along this same direction.

Box 51040 of FIG. 51 covers the binding of labeled-probe-assemblies to the target regions of the sample molecules. For DNA and RNA samples, the method detailed for box 44040 of FIG. 44 can be used.

Box 51048 of FIG. 51 covers the binding of DNA-binding proteins to target locations on the labeled-probe-assemblies. This is accomplished by adding the DNA-binding proteins to the reaction (hybridization) vessel (the same vessel used to extend the labeled-probe-assemblies over the substrate, such as that illustrated in FIG. 7). Appropriate conditions and solution chemistry for binding the DNA-binding proteins to the labeled-probe-assemblies depends on the type of DNA-binding protein used, and can be found in the literature. The DNA-binding proteins may also be cross-linked to the labeled-probe-assemblies. The DNA-binding proteins may be stained, and if stained, the staining can be done either before or after adding them to the reaction vessel. Standard, commercially available, protein stains and protocols are suitable, particularly fluorescent stains. The pattern of proteins along each labeled-probe-assembly is determined by the information encoding protocol employed, and any of the protocols presented, and protocols following from those presented, can be used.

Box 51050 of FIG. 51 covers the extension of the sample-bound labeled-probe-assemblies over the surface of the substrate and fixing of the attached DNA-binding proteins to the substrate. These steps can be conducted in two separate steps by first extending the sample-bound labeled-probe-assemblies over the surface of the substrate using the method detailed of box 44050 of FIG. 44, including drying the substrate. When box 51035 has been used, the extension of the labeled-probe-assemblies should be in a direction perpendicular to that of the direction of sample extension of box 51035. Then the DNA-binding proteins are fixed to the substrate by cross-linking. To cross-link the proteins to the substrate, the substrate is lowered into a vessel containing a solution with cross-linking molecules. As detailed elsewhere in this patent, the type of cross-linking agent will depend on the substrate material and DNA-binding proteins, and typical protein cross-linking agent are often useful, such as glutaraldehyde, formaldehyde, and others. After reacting with the cross-linking agent, the substrate is removed from the vessel, rinsed, and dried.

Box 51056 of FIG. 51 covers the cleaving or consumption of the labeled-probe-assemblies in regions between the bound DNA-binding proteins. This can be done enzymatically using DNases or by chemical exposure. The processes of box 51056 are optional.

Box 51058 of FIG. 51 covers the elongation of the substrate to spatially separate the DNA-binding proteins that are cross-linked to the substrate. The processes of box 51058 are optional. This allows the pattern of DNA-binding proteins on the substrate to be better resolved. For maximum benefit, the substrate is elongated along approximately the same direction as the labeled-probe-assemblies were extended, hence elongate substrate parallel to the direction of extension used in box 51050. Elongation of the substrate can be performed by any method, including those detailed in FIGS. 52 and 53, and detailed in this document.

The remaining process steps of boxes 51060, 51070, and 51080 are detailed above and are the readout and analysis of the data, and the optional repeating of the steps in boxes 51040 through 51070 as is beneficial.

Supporting the process flow outlined in FIG. 51, FIGS. 39-42 illustrate top-views of a portion of substrate 1302 and a portion of one sample DNA molecule 3902 with hybridized labeled-probe-assemblies 3904. The labeled-probe-assemblies 3904 illustrated use cleavable-linkers and substrate stretching perpendicular to the direction in which the sample DNA was extended. By stretching the substrate in this direction, the fragments of labeled-probe-assembly between cleavable-linkers 4002 are spatially separated so that the bits of information encoded into these fragments can be resolved by the readout apparatus. FIGS. 39 and 40 illustrate layouts with generic cleavable-linker containing labeled-probe-assemblies, and FIGS. 41 and 42 illustrate one embodiment using DNA-binding proteins. The labeled-probe-assemblies illustrated in FIGS. 39 and 40 have five cleavable-linkers, whereas FIGS. 41 and 42 illustrate one case with six cleavable-linkers. FIGS. 39 and 40 show the case in which optional box 51035, of FIG. 51, is not utilized, whereas box 51058 is used.

FIGS. 41 and 42 explicitly illustrate one embodiment that uses DNA-binding proteins 4102 bound to labeled-probe-assemblies 3904. The process flow illustrated in FIGS. 41 and 42 use substrate elongation in both the X and Y directions (parallel and perpendicular to the axis of the extended sample DNA molecule, box 51035 and 51058). FIGS. 39 and 41 illustrate the layout after box 51050 of FIG. 51, and FIGS. 40 and 42 illustrate the layout after box 51058. Hence FIGS. 41 and 42 show ordered fragments 4104 of the sample DNA molecule, and FIGS. 39 and 40 show the continuous sample DNA molecule 3902.

Alternate Methods for Extending and Fixing of Sample DNA and Labeled-Probe-Assemblies to Substrate Extension:
　No extension
　　The sample DNA molecules need not be extended and can be simply deposited onto the substrate by any means. Likewise, the labeled-probe-assemblies need not be extended. Alternate embodiments of method of use can be specified in which the sample DNA or labeled-probe-assemblies, or both, are not extended.

The amount of sequence data that can be recovered from a given sample DNA molecule will not be maximal when either the sample DNA or labeled-probe-assemblies are not extended.

DNA combing, passing substrate from liquid into air, nitrogen, or other gaseous atmosphere (non-oxidizing atmosphere)

Passing from aqueous solution into non-polar liquid
  Particularly where substrate surface is hydrophilic
    Float non-polar liquid on aqueous liquid and pull substrate from aqueous liquid into non-polar solvent and from non-polar solvent into air (or dry or moist nitrogen atmosphere).
    Where non-polar liquid is more dense than aqueous solution, pull substrate from aqueous solution down into non-polar liquid, once substrate is completely in non-polar liquid remove aqueous solution from on top, then pull substrate from non-polar liquid into air (or dry or moist nitrogen atmosphere).

Passing through lipid bilayer or other thin solute barrier such as oil or fluorinert (3M Corp.) from a first aqueous solution into a second aqueous solution where DNA is not extended on substrate in first solution and is extended on substrate in second solution, and with pH of first solution such that substrate has a negative or neutral charge and DNA has a negative charge, and with pH of second solution such that substrate has a positive charge and DNA has a negative charge.
  Use bead of non-polar liquid between substrate and barrier wall. Structure of substrate, non-polar liquid, and barrier wall separate the first aqueous solution and the second aqueous solution. Substrate and barrier wall move relative to each other such that a portion of substrate is initially exposed to first solution and later exposed to the second solution.

Directed propagation of a freeze front, directed propagation of a solidification front, directed propagation of a gel-front, directed propagation of a liquid to solid reaction front (2-D and 3-D (i.e. extension in z-direction))

Fluid flow, thin-layer fluid flow

LB film encapsulation (Langmuir-Blodgett)
  Entrain DNA under LB film during pulling of LB film onto substrate
  Particularly where LB film and/or substrate is hygroscopic (such as lipid and other ambipolar molecules)
  Where substrate surface is hydrophilic, such as a thick layer of ambipolar molecules (such as a lipid or mixture of lipids) with the surface layer of molecules self-aligned such that the hydrophilic headgroups face the aqueous solution, and the LB film is also ambipolar molecules, such that the final pulled structure includes two sheets of hydrophilic headgroups separated by a thin layer of aqueous solution and extended DNA.
  Where substrate surface is hydrophilic, such as a monolayer of ambipolar molecules over the substrate with the surface layer of ambipolar molecules self-aligned such that the hydrophilic headgroups face the aqueous solution, and the LB film is also ambipolar molecules, such that the final pulled structure includes two sheets of hydrophilic headgroups separated by a thin layer of aqueous solution and DNA. The ambipolar molecules may be single type of lipid, such as phosphatidylethanolamine 16:0 or phosphatidylethanolamine 18:1, or mixture of lipids Electric field extension followed by relatively rapid removal from solution, or Electric-field extension followed by change in pH so that substrate and labeled-assembly attract.

Droplet spreading and rapid extraction of substrate from aqueous fluid filled container.

Substrate and solution pH combination so that label-assembly is repelled from contact with substrate Solution pH, salt concentration, temperature, surfactant, etc., such that adjacent label-assemblies do not attract with each other, and pulling from the solution to extend the DNA.

Fixing:
  Non-specific surface binding
  Film forming additives in solution (PVOH, PEO, sugar, surfactant, etc.) allowed to dry on substrate
  Hydrophilic/hydrophobic surface forces (hydrophilic substrate surface and pulling substrate into non-polar solvent, followed by evaporation of solvent or curing or cooling below softening point of thermoplastic of non-polar polymer solution)
  Label-assembly-to-substrate-surface cross-linking agent added to thin-film flow after have given sufficient flow time to have already substantially straightened DNA
  Encapsulation in solid or cross-link to gel
  Encapsulation under LB film
  Cross-link labeled-probe-assembly to substrate
  Cross-link proteins on labeled-probe-assembly to substrate
  Cross-linking of individual portions of cleavable labeled-probe-assembly to substrate while maintaining original order of portions in cleavable labeled-probe-assembly.
  Drying (80 C for 15 minutes) leading to hydrophobic/hydrophobic interactions upon re-hydration
  UV cross-linking
  Bind DNA to proteins (histones and other DNA binding proteins) and fix proteins to substrate by cross-linking (formaldehyde, glutaraldehyde, of other protein cross-linkers) or surface forces
    Can covalently bind DNA to proteins by UV, visible light+Methylene Blue, formaldehyde, and other cross-linkers Alternate Substrates and Methods for their Elongation Flowable Substrates: (Flow Expansion as Far as to a Monolayer)
  Substrate of lipid
  Substrate of mixed lipids (different fatty acid chains, different head groups (charged and uncharged, etc))
  Ambipolar molecules in addition to lipids, both pure and mixtures of such. (cholesterol, immiscible non-polar molecules with amine, hydroxyl, and carboxyl end groups, dodecosanylamine)
  Substrate of lipid mixed with non-polar (hydrophobic) molecules, preferably with surface layer of lipid
  Substrate of lipid mixed with cholesterol
  Substrate of lipid mixed with other ambipolar molecular species.
  Substrate of immiscible, hydrophobic material (wax, octododecane, 1-octodcyldecane, high viscosity silicone oil, silicone gel, etc.) with a monolayer (LB film or otherwise formed) or thicker lipid or other ambipolar molecule surface layer
  Substrate of immiscible, hydrophobic material (wax, octododecane, 1-octodcyldecane, high viscosity silicone oil, silicone gel, etc.), which are especially good for hydrophobic surface binding of proteins As above where one or more of the species of molecules is UV cross-linkable or thermally cross-linkable or can be easily bound to a support surface, such as biotin or avidin labeled molecules and support surface functionalized with complementary component, such as avidin or streptavidin and biotin Methods for Deforming Substrate:
  Flow, Surface Spreading, Surface Expansion as for the preparation of a LB film (either float and expand on surface of aqueous solution, or for higher density substrate material, flow along bottom of aqueous solution filled tank)
    Surface spreading of thin substrate fabricated of immiscible material (such as phosphatidylethanolamine or 1-octadecylamine) over surface of water, where water temperature is sufficient to melt substrate, and recovery of surface film (spread substrate) onto chilled plate.
  Deformation of thin substrate on blow-moldable carrier substrate
    Suitable blow-moldable carrier materials include polymer mixtures based on polyethylene acetate
    Affix thin substrate to carrier, then elongate by blow-molding carrier to form a long cylinder.
  Plastic deformation of substrate
  Grow surface by adsorption of molecules and vesicles from aqueous solution (either super saturate solution or change temp, etc of solution to create saturation conditions, thus driving molecules from the solution onto the substrate. And for hydrophobic and ambipolar molecule, molecules adsorbed onto the substrate surface will move into the surface, thus expanding the surface.)
  Flow melted substrate by moving one or more walls of substrate container, with aqueous solution in contact with substrate when molten to keep hydrophilic DNA from being lost into bulk of substrate.
  Elastic stretching of substrate.
  One or more stages of elastic stretching (For case of two stages, start on a silicone based substrate, stretch silicone then transfer to a relaxed or compressed latex substrate with DNA and/or protein cross-linking to final substrate (latex))
  Accordion-folded thin-film substrate. Extend sample DNA perpendicular to compressed accordion folds, and fragment sample DNA and spatially separate by straightening accordion folds.

Alternate Methods and Apparatus for Readout of Information
  Optical microscope
  Fluorescent microscopy with CCD camera, image-intensified video camera, over types of digital cameras, digital line scanner, etc.
  View photographic plate from radioisotope stained labeled-probe-assemblies using digital camera equipped microscope.
  Film camera image of stained labeled-probe-assemblies, then digitize image with digital camera or scanner
  Scan focused laser beam, or crossed beams, over substrate and record fluorescent emission response with photo-detector, micro-channel plate detector, or other detectors, photo-diode detector, or photon counting detector. Construct image of substrate by correlating laser beam location information with detector response. Can also use pulsed laser excitation source and use time-domain fluorescence spectroscopy based detection.
  SEM and TEM
    Digitally record image of pattern of proteins along label-assemblies
  AFM and other types of SPM
    Visualize pattern of proteins or other suitable labels along label-assemblies Alternate Uses of Labeled-Probe-Assemblies Labeled-probe assemblies may be beneficially used to label target molecules in many applications. It is particularly useful where many distinguishable target species exist in a mixture, and where a sample may consist of one or more of many possible target species. Suitable targets for labeling applications include:
  Antigens, Antibodies, receptors, proteins
  dsDNA, ssDNA, mitochondrial DNA, cDNA, SNP's, Alleles
  RNA, mRNA, siRNA
  Virus particles, Bacteria, Fungi, Parasites
  Mixtures of any of these targets
  Chemical analysis
  Environmental chemical analysis (environmental testing)

CONCLUSIONS, RAMIFICATIONS, AND SCOPE OF INVENTION

The labeled-probe-assembly structures, manufacturing methods, information encoding protocols, and methods of use detail above and in FIGS. 1 through 53 are provided as exemplary embodiments of beneficial assemblies, methods, and processes and are not intended to limit the scope of the invention. Accordingly, the scope of the invention should be determined not by the embodiments illustrated, but by the appended claims and their legal equivalents.

I claim:

1. A method for determining base sequence data from a sample molecule of nucleic acid, comprising:
   (a) providing said sample molecule,
   (b) providing a substrate having a top surface,
   (c) providing a readout device,
   (d) extending said sample molecule in a first direction along said top surface,
   (e) attaching said sample molecule to said top surface at a plurality of locations along said sample molecule, (f) processing said sample molecule to form fragments attached to said top surface, said fragments comprising portions of said sample molecule and/or oligomers complementary to portions of said sample molecule, and said fragments having an original ordering along said first direction, (g) elongating said substrate substantially along said first direction such that said fragments are spatially separated and said ordering is maintained, (h) processing said fragments to produce signals correlated with the sequence of bases along each of said fragments, (i) using said readout device to detect and make a record of said signals and spatial ordering of said signals along said first direction, (j) analyzing said record to determine said base sequence data for said sample molecule, whereby said fragments are processed in parallel and said base sequence data of said sample molecule is constructed from a plurality of shorter sequences.

2. The method of claim 1 wherein a plurality of said sample molecules are provided and the method of claim 1 is applied substantially simultaneously to said plurality of said sample molecules.

3. The method of claim 1 wherein the elongating of said substrate comprises:

(k) providing said substrate having said top surface and a melting or softening temperature below approximately 100 C, (l) providing a second substrate having a second top surface and an original length and width and having elastic properties, (m) heating said second substrate to a temperature approximately equal to or greater than said melting or softening temperature, (n) immediately contacting said substrate to said second top surface such that said top surface is approximately parallel to said second top surface, (o) waiting for heat to flow from said second substrate into said substrate and said substrate to soften or melt, (p) stretching said second substrate such that said second substrate remains whole and said substrate is elongated in approximately said first direction, (q) holding said second substrate in the stretched shape, and cooling said substrate until solid, (r) peeling said substrate from said second top surface, (s) relaxing said second substrate to approximately said original length and width, (t) repeating steps (m) through (s) for a predetermined number of cycles.

4. The method of claim 1 wherein the processing of said fragments to produce signals comprises at least one of the methods selected from the group consisting of pyrosequencing, sequencing by synthesis, sequencing by incorporation, and sequencing by hybridization.

5. The method of claim 1 further including in step (i) using said readout device for measuring and recording absolute or relative distances between said signals along said first direction, and including the distance data in said record.

6. A method for determining base sequence data from a sample molecule of nucleic acid using labeled probe assemblies, comprising:

(a) providing said sample molecule comprising a plurality of target sequences, (b) providing a substrate having a top surface, (c) providing a readout device, (d) providing a multitude of said labeled probe assemblies, each of said labeled probe assemblies comprising a probe means and a label assembly, said probe means having a predetermined structure selected to preferentially bind to a predetermined member of said target sequences, and said label assembly having an elongated linear structure with two ends, and wherein a plurality of information encoded structures are located along said elongated linear structure, said information encoded structures being either visible to said readout device or made visible to said readout device by a further process, adjacent members of said information encoded structures having a minimum separation distance approximately equal to or greater than a minimum spatial resolution of said readout device, wherein said separation distance is measured between centers of said adjacent members, and wherein said plurality of information encoded structures form a predetermined pattern, said predetermined pattern being correlated with the identity of said predetermined member of said target sequences, and said probe element is attached to one of said ends, (e) providing a correlation table that lists the correlation between each of said predetermined patterns and each of said predetermined member of said target sequences, (f) extending said sample molecule in a first direction along said top surface, (g) fixing said sample molecule to said top surface at a plurality of locations along said sample molecule, (h) applying a solution containing said labeled probe assemblies to said top surface and binding said probe elements to said target sequences to produce a plurality of target bound labeled probe assemblies, (i) extending said target bound labeled probe assemblies in a second direction along said top surface, and fixing said target bound labeled probe assemblies to said top surface, (j) processing, if required, of said information encoded structures on said target bound labeled probe assemblies to make said information encoded structures visible to said readout device, (k) collecting a first data set by placing said substrate into said readout device and reading out and recording said predetermined pattern from each of said target bound labeled probe assemblies and reading out and recording a list of the order of said target bound labeled probe assemblies along said first direction, (l) translating said first data set into a second data set by using said correlation table, (m) generating a third data set by arranging the data in said second data set in the order of said list, whereby base sequence information for said sample molecule is acquired from information contained on said target bound labeled probe assemblies and the order of said target bound labeled probe assemblies along said sample molecule.

7. The method of claim 6 further including cleaving said sample molecule into a plurality of fragments, said fragments comprising said target sequences, and spatially separating said fragments, such that the order of said fragments on said substrate is maintained, prior to one of the steps selected from the group consisting of step (h), (i), (j), and (k).

8. The method of claim 7 wherein the method of cleaving said sample molecule and spatially separating said fragments comprises:

(n) providing said substrate having said top surface and a melting or softening temperature below approximately 100 C, (o) providing a second substrate having a second top surface and an original length and width and having elastic properties, (p) cleaving said sample molecule at a plurality of locations thereby producing a plurality of said fragments of said sample molecule attached to said top surface,
(q) heating said second substrate to a temperature approximately equal to or greater than said melting or softening temperature,
(r) immediately contacting said substrate to said second top surface such that said top surface is approximately parallel to said second top surface,
(s) waiting for heat to flow from said second substrate into said substrate and said substrate to soften or melt,
(t) stretching said second substrate in one direction or in two perpendicular directions in approximately the plane of said top surface such that said second substrate remains whole and said substrate is elongated,
(u) holding said second substrate in the stretched shape, and cooling said substrate until solid,
(v) peeling said substrate from said second top surface,
(w) relaxing said second substrate to approximately said original length and width,
(x) repeating steps (q) through (w) for a predetermined number of cycles.

9. The method of claim 6 wherein a plurality of said sample molecules are provided and the method of claim 6 is applied substantially simultaneously to said plurality of said sample molecules.

10. The method of claim 6 wherein the processing of step (j) includes indirect labeling of said information encoded structures.

11. The method of claim 6 further including in step (k) using said readout device for measuring and recording absolute or relative distances between said target bound labeled probe assemblies along said first direction, and including the distance data in said third data set.

12. The method of claim 6 wherein the process of reading out is carried out by procedures selected from the group consisting of electron microscopy, scanning electron microscopy, transmission electron microscopy, optical microscopy, fluorescent microscopy, time-resolved fluorescent microscopy, scanning probe microscopy, and atomic force microscopy.

13. A method for spatially separating fragments of nucleic acid molecules bound to a substrate, comprising:
(a) providing at least one of said nucleic acid molecules,
(b) providing said substrate having a top surface and a melting or softening temperature below approximately 100 C,
(c) providing a second substrate having a second top surface and an original length and width and having elastic properties,
(d) spreading said nucleic acid molecules onto said top surface,
(e) attaching said nucleic acid molecules to said top surface at a plurality of locations along said nucleic acid molecules,
(f) cleaving said nucleic acid molecules at a plurality of locations along said nucleic acid molecules thereby producing a plurality of said fragments of said nucleic acid molecules attached to said top surface,
(g) heating said second substrate to a temperature approximately equal to or greater than said melting or softening temperature,
(h) immediately contacting said substrate to said second top surface such that said top surface is approximately parallel to said second top surface,
(i) waiting for heat to flow from said second substrate into said substrate and said substrate to soften or melt,
(j) stretching said second substrate in one direction or in two perpendicular directions in approximately the plane of said top surface such that said second substrate remains whole and said substrate is elongated,
(k) holding said second substrate in the stretched shape, and cooling said substrate until solid,
(l) peeling said substrate from said second top surface,
(m) relaxing said second substrate to approximately said original length and width,
(n) repeating steps (g) through (m) for a predetermined number of cycles,
whereby said nucleic acid molecules are divided into said fragments and said fragments are spatially separated while the original order and relative spacing of said fragments are maintained and said fragments are bound to said substrate in preparation for further processing.

14. The method of claim 13 wherein said nucleic acid molecules are selected from the group consisting of double stranded DNA, single strand DNA, complementary DNA, double stranded RNA, single strand RNA, heteroduplex of DNA and RNA.

15. The method of claim 13 wherein said substrate is composed of two layers, each of said layers disposed approximately parallel to said top surface and said top surface is the uppermost surface of a top layer, and wherein said top layer is composed of materials selected from the group consisting of 1-octadecylamine, 1-octadecanethiol, 1-eicosanol, 1-decosene, eicosanoic acid, phosphatidylethanolamine, phosphatidylthiolethanol, and cholesterol, and the layer below said top layer is composed of materials selected from the group consisting of paraffin wax, synthetic and natural waxes having a melting temperature below 70 C, eicosane, docosane, octadecane, and silicone gel.

16. The method of claim 13 wherein said substrate is composed of materials selected from the group consisting of paraffin wax, synthetic and natural waxes having a melting temperature below 70 C, eicosane, docosane, octadecane, phosphatidylethanolamine, phosphatidylthiolethanol, 1-octadecylamine, 1-octadecanethiol, and cholesterol.

17. The method of claim 13 wherein said second substrate comprises a material selected from the group consisting of polydimethylsiloxane elastomer, silicone rubber, fluorosilicone elastomer, Dow Corning Sylgard 186 silicone elastomer, Teflon skive tape, polyethylacetate, polyurethane rubber, neoprene rubber, latex rubber, and nitrile rubber.

* * * * *